United States Patent
Nakamura et al.

(10) Patent No.: US 9,359,324 B2
(45) Date of Patent: Jun. 7, 2016

(54) PROCESS FOR PREPARING EPISULFIDE COMPOUNDS

(71) Applicant: Asahi Kasei Chemicals Corporation, Tokyo (JP)

(72) Inventors: Akitake Nakamura, Tokyo (JP); Takeshi Endo, Fukuoka (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/656,764

(22) Filed: Mar. 13, 2015

(65) Prior Publication Data

US 2015/0197501 A1 Jul. 16, 2015

Related U.S. Application Data

(62) Division of application No. 14/112,795, filed as application No. PCT/JP2012/060705 on Apr. 20, 2012, now Pat. No. 9,051,293.

(30) Foreign Application Priority Data

Apr. 21, 2011 (JP) ................................ 2011-095015

(51) Int. Cl.
C07D 331/02 (2006.01)
(52) U.S. Cl.
CPC ..................... C07D 331/02 (2013.01)
(58) Field of Classification Search
CPC .................................................. C07D 331/02
USPC .......................................................... 549/90
See application file for complete search history.

(56) References Cited

U.S. PATENT DOCUMENTS

| 3,560,524 | A | 2/1971 | Clason et al. |
| 7,183,441 | B2 | 2/2007 | Kondo et al. |
| 7,309,794 | B1 | 12/2007 | Amagai et al. |
| 9,051,293 | B2 * | 6/2015 | Nakamura ............ C07D 331/02 |
| 2003/0149231 | A1 | 8/2003 | Amagai et al. |

FOREIGN PATENT DOCUMENTS

| CN | 101602702 A | 12/2009 |
| JP | H11-012273 A | 1/1999 |
| JP | H11-183702 A | 7/1999 |
| JP | 2000-186086 A | 7/2000 |
| JP | 2000-186087 A | 7/2000 |
| JP | 2001-163872 A | 6/2001 |
| JP | 2003-342274 A | 12/2003 |
| JP | 3883272 B2 | 2/2007 |

OTHER PUBLICATIONS

Calo et al., "A Simple Method for Converting Oxirans into Thiirans Stereospecifically," Journal of the Chemical Society, Chemical Communications, 621-622 (1975).
Yadollahi et al., "Titanium Dioxide as a Mild and Efficient Catalyst for Conversion of Epoxides to Thiiranes," Synthetic Communications, 34: 2823-2827 (2004).
Bandgar et al., "An efficient synthesis of thiiranes from oxiranes using fluoroboric acid adsorbed on silica gel (HBF4-SiO2) as a catalyst under mild conditions in the absence of solvent," Journal of Molecular Catalysis A: Chemical, 273: 114-117 (2007).
Valette et al., "Efficient and solvent-free microwave-accelerated synthesis of isothiocyanates using Lawesson's reagent," Journal of Sulfur Chemistry, 26: 155-161 (2005).
Xin et al., "New Process for Producing Thiourea from Urea," Chemical Industry and Engineering, 23: 407-410 (2006) (see English abstract).
Cava et al., "Tetrahedron Report No. 192: Thionation Reactions of Lawesson's Reagents," Tetrahedron, 41: 5061-5087 (1985).
Foreman et al., "Organo-P-S and P-Se heterocycles," J. Chem. Soc., Dalton Trans., 1533-1543 (2000).
Jesberger et al., "Applications of Lawesson's Reagent in Organic and organometallic Syntheses," Synthesis, 1929-1958 (2003).
Das et al., "An efficient catalyst-free synthesis of thiiranes from oxiranes using polyethylene glycol as the reaction medium," Tetrahedron Letters, 47: 8471-8473 (2006).
International Search Report issued in corresponding International Patent Application No. PCT/JP2012/060705 dated May 29, 2012.
International Preliminary Report on Patentability issued in corresponding International Patent Application No. PCT/JP2012/060705 dated Oct. 31, 2013.
Office Action issued in counterpart Taiwanese Patent Application No. 101114089 dated Nov. 11, 2013.
European Search Report issued in counterpart European Patent Application No. 12774788.9 dated Dec. 20, 2013.
Hauptman et al., "Synthesis of Novel (P,S) Ligands Based on Chiral Nonracemic Episulfides. Use in Asymmetric Hydrogenation," Organometallics, 18: 2061-2073 (1999).
Zeynizadeh et al., "Solvent-Free Conversion of Epoxides to Thiiranes by Thiourea/NH4Cl system," Phosphorus, Sulfur, and Silicon, 183: 2280-2286 (2008).
Surendra et al., "A new and efficient method for the synthesis of thiiranes from oxirane-beta-cyclodextrin complexes and thiourea in water," Tetrahedron Letters, 45: 6523-6526 (2004).

* cited by examiner

*Primary Examiner* — Golam M M Shameem
(74) *Attorney, Agent, or Firm* — Morgan, Lewis & Bockius LLP

(57) ABSTRACT

Provided is a method for producing an episulfide compound, the method including a step of thiating epoxy groups of (B) an epoxy compound by a reaction with (C) a thiating agent in the presence of (A) a polyhydric hydroxyl compound having two or more hydroxyl groups.

8 Claims, No Drawings

PROCESS FOR PREPARING EPISULFIDE COMPOUNDS

TECHNICAL FIELD

The present invention relates to a method for producing an episulfide compound.

BACKGROUND ART

Episulfide compounds are used in a wide variety of fields such as raw material compounds for plastics, adhesives, medicaments, insecticides, and herbicides.

Particularly, in recent years, plastics formed by polymerizing episulfide compounds have characteristics such as a high refractive index, a high Abbe number, high heat resistance and high strength. Therefore, those plastics have been traditionally used as materials having excellent performance in the field of optical materials.

In general, an example of the method for producing an episulfide compound is a method of allowing an epoxy compound to react with a thiating agent.

However, when an episulfide compound is produced by this method, there has been a problem that since there occurs the formation of a polymerization product caused by the high reactivity of the episulfide compound, and a reaction between the episulfide compound and the thiating agent, it is difficult to obtain the episulfide compound with a high yield. Furthermore, since the reaction between an epoxy compound and a thiating agent is slow, the reaction time is long, and there has been a demand for an improvement in terms of productivity.

In order to solve these problems, several methods have been suggested. For example, Non-Patent Literature 1 suggests a method of using a novel thiating agent. Non-Patent Literature 2 suggests a method of using a metal catalyst. Non-Patent Literature 3 suggests a method of using an acid catalyst supported on silica. Patent Literature 1 suggests a method of using only a polar solvent as a reaction solvent.

CITATION LIST

Patent Literature

Patent Literature 1: JP 2001-163872 A

Non Patent Literature

Non-Patent Literature 1: J. Chem. Soc., Chem. Comm 1975, 621-622
Non-Patent Literature 2: Synth. Commun. 2004, 34, 2823-2827
Non-Patent Literature 3: J. Mol. Cat. A: Chem. 2007, 273, 114-117

SUMMARY OF INVENTION

Technical Problem

However, the novel thiating agent described in Non-Patent Literature 1 is not generally popularized but is an expensive thiating agent that is not easily available. Therefore, the thiating agent tends to increase the cost needed for the production of episulfide compounds.

In the production method using a metal catalyst described in Non-Patent Literature 2, there are occasions in which the metal catalyst reacts with the episulfide compound, and decreases the yield. Furthermore, depending on the use of the episulfide compound thus produced, it is necessary to remove the metal catalyst. Therefore, the cost needed for the production of episulfide compounds tends to increase. Furthermore, since a metal catalyst is used, the method is a method which is relatively disadvantageous in terms of a reduction of environmental load.

When the acid catalyst supported on silica as described in Non-Patent Document 3 is used, there is a possibility that after completion of the reaction between the epoxy compound and the thiating agent, the catalyst can be easily removed and reutilized, it is contemplated that the environmental load is small. However, the catalyst used in this method is generally not in widespread use and is a highly expensive catalyst that is not easily available. Therefore, according to this method, the cost needed for the production of episulfide compounds tends to increase.

In regard to the method of using only polar solvents as the reaction solvent as described in Patent Literature 1, it is disclosed that the net production yield is 59% to 66.6%, but there is still room for an improvement in the yield.

The present invention was achieved in view of such circumstances, and an object of the invention is to provide a method for producing an episulfide compound, which method takes a short reaction time, gives a high yield, exhibits excellent economic efficiency, and imposes less environmental load.

Solution to Problem

The inventors of the present invention found that a method for producing an episulfide compound, which includes a process of thiating epoxy groups of (B) an epoxy compound through a reaction with (C) a thiating agent in the presence of (A) a polyhydric hydroxyl compound having two or more hydroxyl groups, takes a short reaction time, gives a high yield, exhibits excellent economic efficiency, and imposes less environmental load, thus completing the present invention.

That is, the present invention is as follows:

[1] A method for producing an episulfide compound, the method including a step of thiating epoxy groups of (B) an epoxy compound through a reaction with (C) a thiating agent in the presence of (A) a polyhydric hydroxyl compound having two or more hydroxyl groups.

[2] The method as described in item [1], in which the hydroxyl value of the (A) polyhydric hydroxyl compound is 300 mg/g to 1870 mg/g.

[3] The method as described in item [1], in which the hydroxyl value of the (A) polyhydric hydroxyl group is greater than 1870 mg/g and less than or equal to 3000 mg/g.

[4] The method as described in item [1], in which the (A) polyhydric hydroxyl compound is a compound having two hydroxyl groups.

[5] The method as described in item [1], in which the (A) polyhydric hydroxyl compound is a compound having three or more hydroxyl groups.

[6] The method as described in item [1], in which the (A) polyhydric hydroxyl compound has 3 to 20 carbon atoms.

[7] The method as described in item [1], in which the (A) polyhydric hydroxyl compound is a compound having two hydroxyl groups and 3 to 20 carbon atoms, and having a hydroxyl value of 300 mg/g to 1870 mg/g.

[8] The method as described in item [1], in which the (A) polyhydric hydroxyl compound is a compound having three hydroxyl groups and 4 to 20 carbon atoms, and having a hydroxyl value of 300 mg/g to 1870 mg/g.

[9] The method as described in item [1], in which the (A) polyhydric hydroxyl compound is a compound having four or more hydroxyl groups and having a hydroxyl value of 300 mg/g to 1870 mg/g.

[10] The method as described in item [1], in which the (A) polyhydric hydroxyl compound is a compound having a chain-like, branched or cyclic aliphatic hydrocarbon group, and the two or more hydroxyl groups contained in the (A) polyhydric hydroxyl compound are each respectively bonded to different carbon atoms in the aliphatic hydrocarbon group.

[11] The method as described in item [1], in which the (C) thiating agent includes at least one compound selected from the group consisting of thiocyanates and thioureas.

[12] The method as described in item [1], in which the mixing index α of the (B) epoxy compound and the (C) thiating agent, which is represented by the following formula (1), is 1 to 10:

$$\text{Mixing index } \alpha = \alpha t/\alpha e \quad (1)$$

in the formula, αt: amount of substance (mol) of sulfur atoms contained in the thiating agent, which atoms can be used in the production of episulfide groups; and αe: amount of substance (mol) of epoxy groups contained in the epoxy compound.

[13] The method as described in item [1], in which the mixing index β of the (A) polyhydric hydroxyl compound and the (C) thiating agent, which is represented by the following formula (2), is 0.010 to 0.500:

$$\text{Mixing index } \beta = \beta t/\beta o \quad (2)$$

in the formula, βt: mass (g) of the thiating agent; and

βo: mass (g) of the polyhydric hydroxyl compound

[14] The method as described in item [1], in which the (B) epoxy compound has an epoxy equivalent of 55 g/eq. to 700 g/eq.

[15] The method as described in item [1], in which the (B) epoxy compound has a partial structure represented by the following formula (3), (4), (5) or (6):

[Chemical Formula 1]

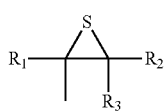

(3)

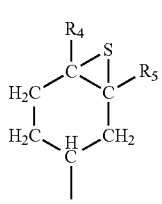

(4)

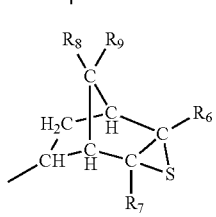

(5)

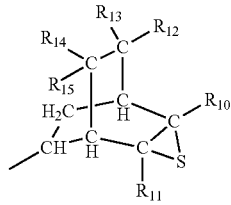

(6)

in the formula, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ each independently represent a hydrogen atom or an organic group having 1 to 10 carbon atoms.

[16] The method as described in item [1], further including:

a step of collecting unreacted epoxy compound from the reaction liquid of the step of thiating epoxy groups of the (B) epoxy compound; and a step of thiating epoxy groups of the (B) epoxy compound that includes the collected epoxy compound, through a reaction with the (C) thiating agent.

[17] The method as described in item [1], further including:

a step of collecting the polyhydric hydroxyl compound from the reaction liquid of the step of thiating epoxy groups of the (B) epoxy compound; and a step of thiating epoxy groups of the (B) epoxy compound through a reaction with the (C) thiating agent in the presence of the (A) polyhydric hydroxyl compound that includes the collected polyhydric hydroxyl compound.

[18] The method as described in item [1], further including a step of regenerating the thiating agent from a compound produced as a result of substitution of sulfur atoms of the (C) thiating agent with oxygen atoms in the step of thiating epoxy groups of the (B) epoxy compound.

[19] The method as described in item [1], further including a step of thiating epoxy groups of the (B) epoxy compound through a reaction with the (C) thiating agent that includes the unreacted thiating agent collected from the reaction liquid of the step of thiating epoxy groups of the (B) epoxy compound.

[20] The method as described in item [18], further including a step of thiating epoxy groups of the (B) epoxy compound through a reaction with the (C) thiating agent that includes the regenerated thiating agent.

Advantageous Effects of Invention

According to the present invention, there is provided a method for producing an episulfide compound, which method takes a short reaction time, gives a high yield, exhibits excellent economic efficiency, and imposes less environmental load.

DESCRIPTION OF EMBODIMENTS

Hereinafter, an embodiment for carrying out the present invention (hereinafter, referred to as "present exemplary embodiment") will be described in detail. However, the present invention is not intended to be limited to the following present exemplary embodiment, and various modifications can be made within the scope of the gist.

The production method related to the present exemplary embodiment includes a step of thiating epoxy groups of (B) an epoxy compound through a reaction with (C) a thiating agent in the presence of (A) a polyhydric hydroxyl compound having two or more hydroxyl groups. Hereinafter, the details of the (A) polyhydric hydroxyl compound, (B) epoxy compound, (C) thiating agent, and other components will be described.

((A) Polyhydric Hydroxyl Compound)

The (A) polyhydric hydroxyl compound of the present exemplary embodiment is a compound having two or more hydroxyl groups. A single kind of polyhydric hydroxyl compound may be used alone, or plural kinds of polyhydric hydroxyl compounds may also be used in combination.

The hydroxyl value of the (A) polyhydric hydroxyl compound is preferably 300 mg/g or greater, more preferably 500 mg/g or greater, and even more preferably 700 mg/g or greater. When the hydroxyl value is 300 mg/g or greater, the production of a polymerization product between the molecules of the episulfide compound and the production of a reaction product between the episulfide compound and the thiating agent can be suppressed, and the yield tends to further increase. When the hydroxyl value is 500 mg/g or greater, the reaction time is further shortened, and economic efficiency tends to be excellent. From the same viewpoint, the hydroxyl value is even more preferably 700 mg/g or greater.

The hydroxyl value of the polyhydric hydroxyl compound is preferably 1870 mg/g or less, more preferably 1830 mg/g or less, and even more preferably 1810 mg/g or less. When the hydroxyl value is 1870 mg/g or less, the concentration of the thiating agent in the reaction system can be increased, the production process can be simplified, and economic efficiency tends to be excellent. When the hydroxyl value is 1830 mg/g or less, the production of a polymerization product between the molecules of the episulfide compound and the production of a reaction product between the episulfide compound and the thiating agent can be suppressed, and the yield tends to further increase. When the hydroxyl value is 1810 mg/g or less, the reaction time is further shortened, and economic efficiency tends to be excellent. When the hydroxyl value is greater than 1870 mg/g, even if the amount of use of the (A) polyhydric hydroxyl compound is small, the yield is higher, or the reaction time is further shortened, and economic efficiency tends to be excellent, which is preferable. Furthermore, from the viewpoint that the polyhydric hydroxyl compound is easily available, and economic efficiency tends to be excellent, the hydroxyl value is preferably 3000 mg/g or less.

The (A) polyhydric hydroxyl compound has two or more hydroxyl groups. When a polyhydric hydroxyl compound having two or more hydroxyl groups is used, the reaction time is shortened, the production of a polymerization product between the molecules of the episulfide compound and the production of a reaction product between the episulfide compound and the thiating agent can be suppressed, and the yield can be increased. When there are two hydroxyl groups, a large number of compounds tend to be easily available. Therefore, from the viewpoint of yield or reaction time, the possibility in which an optimal combination with the (B) epoxy compound can be found increases, and this is particularly preferable. When the polyhydric hydroxyl compound has three or more hydroxyl groups, even if the amount of use of the (A) polyhydric hydroxyl compound is small, the yield further increases, or the reaction time is shortened, and economic efficiency tends to be excellent, which is preferable. The polyhydric hydroxyl compound more preferably has four or more hydroxyl groups.

The number of carbon atoms of the (A) polyhydric hydroxyl compound is preferably 3 or greater. When the number of carbon atoms is 3 or greater, the reaction time becomes particularly short, and economic efficiency tends to be excellent. The number of carbon atoms of the polyhydric hydroxyl compound is preferably 20 or less, more preferably 8 or less, and even more preferably 6 or less. When the number of carbon atoms is 20 or less, the polyhydric hydroxyl compound is easily available and economic efficiency tends to be excellent. When the number of carbon atoms is 8 or less, the reaction time is shortened, the production of a polymerization product between the molecules of the episulfide compound and the production of a reaction product between the episulfide compound and the thiating agent can be suppressed, and the yield can be increased. When the number of carbon atoms is 6 or less, the polyhydric hydroxyl compound tends to be liquid in the standard state, and is easy to handle.

When the combination of the hydroxyl value, the number of hydroxyl groups, and the number of carbon atoms of the (A) polyhydric hydroxyl compound includes:

two hydroxyl groups, 3 to 20 carbon atoms, and a hydroxyl value of 300 mg/g to 1870 mg/g, three hydroxyl groups, 4 to 20 carbon atoms, and a hydroxyl value of 300 mg/g to 1870 mg/g, or four or more hydroxyl groups and a hydroxyl value of 300 mg/g to 1870 mg/g, it is preferable from the viewpoint that the reaction time is particularly shortened, the production of a polymerization product between the molecules of the episulfide compound and the production of a reaction between the episulfide compound and the thiating agent can be suppressed, and the yield can be especially increased.

The (A) polyhydric hydroxyl compound is preferably a compound having a chain-like, branched or cyclic aliphatic hydrocarbon group. In view of being easily available and having a tendency to exhibit excellent economic efficiency, the polyhydric hydroxyl compound is more preferably a compound having a chain-like or cyclic aliphatic hydrocarbon group, and even more preferably a compound having a chain-like aliphatic hydrocarbon group. Furthermore, the hydroxyl group contained in the (A) polyhydric hydroxyl compound is preferably bonded to a carbon atom of the aliphatic hydrocarbon group.

The (A) polyhydric hydroxyl compound is preferably that two or more hydroxyl groups be each respectively bonded to different carbon atoms. When two or more hydroxyl groups are each respectively bonded to different carbon atoms, the stability of the compound tends to increase.

The (A) polyhydric hydroxyl compound is, for example, at least one compound selected from the group consisting of methanediol, ethylene glycol, 1,2-propanediol, 1,3-propanediol, 1,2-cyclopropanediol, glycerin, 1,2-butanediol, 1,3-butanediol, 1,4-butanediol, 2,3-butanediol, 2-methyl-1,3-propanediol, 1,2-cyclobutanediol, 1,3-cyclobutanediol, 1,2,3-butanetriol, 1,2,4-butanetriol, 1,2,3,4-butanetetraol, 1,2,3-cyclobutanetriol, 1,2,3,4-cyclobutanetetraol, 1,2-pentanediol, 1,3-pentanediol, 1,4-pentanediol, 1,5-pentanediol, 2,3-pentanediol, 2,4-pentanediol, 1,2,3-pentanetriol, 1,2,4-pentanetriol, 1,2,5-pentanetriol, 1,3,4-pentanetriol, 1,3,5-pentanetriol, 1,2,3,4-pentanetetraol, 1,2,3,5-pentanetetraol, 1,2,4,5-pentanetetraol, 1,2,3,4,5-pentanepentaol, 1,2,3-cyclopentanetriol, 1,2,4-cyclopentanetriol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 3,4-hexanediol, 1,2-cyclohexanediol, 1,3-cyclohexanediol, 1,4-cyclohexanediol, 1,2,3-hexanetriol, 1,2,4-hexanetriol, 1,2,5-hexanetriol, 1,2,6-hexanetriol, 1,3,4-hexanetriol, 1,3,5-hexanetriol, 1,3,6-hexanetriol, 1,4,5-hexanetriol, 1,4,6-hexanetriol, 2,3,4-hexanetriol, 2,3,5-hexanetriol, 1,2,3,4-hexanetetraol, 1,2,3,5-hexanetetraol, 1,2,3,6-hexanetetraol, 1,3,4,5-hexanetetraol, 1,3,4,6-hexanetetraol, 1,2,3,4,5-hexanepentaol, 1,2,3,4,6-hexanepentaol, 1,2,3,4,5,6-hexanehexaol, 1,2,3-cyclohexanetriol, 1,2,4-cyclohexanetriol, 1,3,6-cyclohexanetriol, 1,2,3,4-cyclohexanetetraol, 1,2,3,5-cyclohexanetetraol, 1,2,3,4,5-cyclohexanepentaol, 1,2,3,4,5,6-cyclohexanehexaol, 1,2-heptanediol, 1,3-heptanediol, 1,4-heptanediol, 1,5-heptanediol, 1,6-heptanediol, 1,7-heptanediol, 2,3-heptanediol, 2,4-heptanediol, 2,5-heptanediol, 2,6-heptanediol, 3,4-heptanediol, 3,5-heptanediol, bicyclo[2,2,1]heptanediol, 1,2,3-heptanetriol, 1,2,4-heptanetriol, 1,2,5-heptanetriol, 1,2,6-heptanetriol, 1,2,7-heptanetriol, 1,3,4-heptanetriol, 1,3,5-heptanetriol, 1,3,6-heptanetriol, 1,3,7-heptanetriol, 1,3,8-heptanetriol, 1,4,5-heptanetriol, 1,4,6-heptanetriol, 1,4,7-heptanetriol, 1,5,6-heptanetriol, 2,3,4-heptanetriol, 2,3,5-heptanetriol, 2,3,6-heptanetriol, 3,4,5-heptanetriol, 1,2,3,4-heptanetetraol, 1,2,3,5-heptanetetraol, 1,2,3,6-heptanetetraol, 1,2,3,7-heptanetetraol, 1,3,4,5-heptanetetraol, 1,3,4,6-heptanetetraol, 1,3,4,7-heptanetetraol, 1,4,5,6-heptanetetraol, 1,4,5,7-heptanetetraol, 1,5,6,7-heptanetetraol, 1,2,3,4,5-heptanepentaol, 1,2,3,4,6-heptanepentaol, 1,2,3,4,7-heptanepentaol, 1,3,4,5,6-heptanepentaol, 1,3,4,5,7-heptanepentaol, 1,4,5,6,7-heptanepentaol, 1,2,3,4,5,6-heptanehexaol, 1,2,3,4,5,7-heptanehexaol, 1,2,3,4,5,6,7-heptaneheptanol, 1,2,3-cycloheptanetriol, 1,2,4-cycloheptanetriol, 1,2,5-cycloheptanetriol, 1,3,4-cycloheptanetriol, 1,3,5-cycloheptanetriol, 1,2,3,4-cycloheptanetetraol, 1,2,3,5-cycloheptanetetraol, 1,3,4,5-cycloheptanetetraol, 1,3,4,6-cycloheptanetetraol, 1,2,3,4,5-cycloheptanepentaol, 1,2,3,4,6-cycloheptanepentaol, 1,2,3,4,5,6-cycloheptanehexaol, 1,2,3,4,5,6,7-cycloheptaneheptaol, bicyclo[2,2,1]heptanetriol, bicyclo[2,2,1]heptanetetraol, bicyclo[2,2,1]heptanepentaol, bicyclo[2,2,1]heptanehexaol, bicyclo[2,2,1]heptaneheptaol, 1,2-octanediol, 1,3-octanediol, 1,4-octanediol, 1,5-octanediol, 1,6-octanediol, 1,7-octanediol, 1,8-octanediol, 2,3-octanediol, 2,4-octanediol, 2,5-octanediol, 2,6-octanediol, 2,7-octanediol, 3,4-octanediol, 3,5-octanediol, 3,6-octanediol, 4,5-octanediol, bicyclo[2,2,2]octanediol, 1,2,3-cyclooctanetriol, 1,2,4-cyclooctanetriol, 1,2,5-cyclooctanetriol, 1,3,4-cyclooctanetriol, 1,3,5-cyclooctanetriol, 1,3,6-cyclooctanetriol, 1,4,5-cyclooctanetriol, 1,4,6-cyclooctanetriol, 1,2,3,4-cyclooctanetetraol, 1,2,3,5-cyclooctanetetraol, 1,2,3,6-cyclooctanetetraol, 1,3,4,5-cyclooctanetetraol, 1,3,4,6-cyclooctanetetraol, 1,3,4,7-cyclooctanetetraol, 1,4,5,6-cyclooctanetetraol, 1,2,3,4,5-cyclooctanepentaol, 1,2,3,4,6-cyclooctanepentaol, 1,2,3,4,7-cyclooctanepentaol, 1,3,4,5,6-cyclooctanepentaol, 1,3,4,5,7-cyclooctanepentaol, 1,4,5,6,7-cyclooctanepentaol, 1,2,3,4,5,6-cyclooctanehexaol, 1,2,3,4,5,7-cyclooctanehexaol, 1,2,3,4,5,6,7-cyclooctaneheptaol, 1,2,3,4,5,6,7,8-cyclooctaneoctaol, bicyclo[2,2,2]octanetriol, bicyclo[2,2,2]octanetetraol, bicyclo[2,2,2]octanepentaol, bicyclo[2,2,2]octanehexaol, bicyclo[2,2,2]octaneheptaol, bicyclo[2,2,2]octaneoctaol, 1,2-nonanediol, 1,3-nonanediol, 1,4-nonanediol, 1,5-nonanediol, 1,6-nonanediol, 1,7-nonanediol, 1,8-nonanediol, 1,9-nonanediol, 2,3-nonanediol, 2,4-nonanediol, 2,5-nonanediol, 2,6-nonanediol, 2,7-nonanediol, 2,8-nonanediol, 3,4-nonanediol, 3,5-nonanediol, 3,6-nonanediol, 3,7-nonanediol, 4,5-nonanediol, 4,6-nonanediol, 1,2-cyclononanediol, 1,3-cyclononanediol, 1,4-cyclononanediol, 1,5-cyclononanediol, 1,2-decanediol, 1,3-decanediol, 1,4-decanediol, 1,5-decanediol, 1,6-decanediol, 1,7-decanediol, 1,8-decanediol, 1,9-decanediol, 1,10-decanediol, 2,3-decanediol, 2,4-decanediol, 2,5-decanediol, 2,6-decanediol, 2,7-decanediol, 2,8-decanediol, 2,9-decanediol, 3,4-decanediol, 3,5-decanediol, 3,6-decanediol, 3,7-decanediol, 3,8-decanediol, 4,5-decanediol, 4,6-decanediol, 4,7-decanediol, 5,6-decanediol, 1,2-cyclodecanediol, 1,3-cyclodecanediol, 1,4-cyclodecanediol, 1,5-cyclodecanediol, 1,6-cyclodecanediol, undecanediol, dodecanediol, tridecanediol, tetradecanediol, pentadecanediol, hexadecanediol, heptadecanediol, octadecanediol, nonadecanediol, icosanediol, diethylene glycol, triethylene glycol, tetraethylene glycol, pentaethylene glycol, hexaethylene glycol, heptaethylene glycol, octaethylene glycol, nonaethylene glycol, decaethylene glycol, undecaethylene glycol, dodecaethylene glycol, polyethylene glycol 28, polyethylene glycol 200, polyethylene glycol 300, polyethylene glycol 400, glyceraldehyde, erythrose, treose, ribose, lyxose, xylose, arabinose, apiose, allose, talose, gulose, glucose, altrose, mannose, galactose, idose, dihydroxyacetone, erythrulose, ribulose, xylulose, psicose, fructose, sorbose, tagatose, sedoheptulose, coriose, sucrose, lactulose, lactose, maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, and primeverose.

The (A) polyhydric hydroxyl compound may also be at least one compound selected from the group consisting of ethylene glycol, propanediol, cyclopropanediol, butanediol, cyclobutanediol, pentanediol, cyclopentanediol, hexanediol, cyclohexanediol, heptanediol, cycloheptanediol, octanediol, cyclooctanediol, nonanediol, cyclononanediol, decanediol, cyclodecanediol, undecanediol, dodecanediol, tridecanediol, tetradecanediol, pentadecanediol, hexadecanediol, heptadecanediol, octadecanediol, nonadecanediol and icosanediol, each having at least one substituent selected from the group consisting of a methyl group, an ethyl group, a hydroxymethyl group and a hydroxylethyl group.

Among those described above, from the viewpoint of shortening the reaction time, suppressing the production of a polymerization product between the molecules of the episulfide compound and a reaction product between the episulfide compound and the thiating agent, and achieving a higher yield, it is preferable to use at least one compound selected from the following group as the polyhydric hydroxyl compound:

ethylene glycol, 1,2-propanediol, 1,3-propanediol, 1,2-cyclopropanediol, 1,2-butanediol, 1,3-butanediol, 1,4-butanediol, 2,3-butanediol, 2-methyl-1,3-propanediol, 1,2-pentanediol, 1,3-pentanediol, 1,4-pentanediol, 1,5-pentanediol, 2,3-pentanediol, 2,4-pentanediol, 2-methyl-1,3-butanediol, 2-methyl-1,4-butanediol, 2,2-dimethyl-1,3-propanediol, 1,2-cyclopentanediol, 1,3-cyclopentanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 3,4-hexanediol, 1,2-cyclohexanediol, 1,3-cyclohexanediol, 1,4-cyclohexanediol, 1,2-heptanediol, 1,3-heptanediol, 1,4-heptanediol, 1,5-heptanediol, 1,6-heptanediol, 1,7-heptanediol, 2,3-heptanediol, 2,4-heptanediol, 2,5-heptanediol, 2,6-heptanediol, 3,4-heptanediol, 3,5-heptanediol, 1,2-cycloheptanediol, 1,3-cycloheptanediol, 1,4-cycloheptanediol, bicyclo[2,2,1]heptanediol, 1,2-octanediol, 1,3-octanediol, 1,4-octanediol, 1,5-octanediol, 1,6-octanediol, 1,7-octanediol, 1,8-octanediol, 2,3-octanediol, 2,4-octanediol, 2,5-octanediol, 2,6-octanediol, 2,7-octanediol, 3,4-octanediol, 3,5-octanediol, 3,6-octanediol, 4,5-octanediol, 1,2-cyclooctanediol, 1,3-cyclooctanediol, 1,4-cyclooctanediol, 1,5-cyclooctanediol, bicyclo[2,2,2]octanediol, 1,2-nonanediol, 1,3-nonanediol, 1,4-nonanediol, 1,5-nonanediol, 1,6-nonanediol, 1,7-nonanediol, 1,8-nonanediol, 1,9-nonanediol, 2,3-nonanediol, 2,4- nonanediol, 2,5-nonanediol, 2,6-nonanediol, 2,7-nonanediol, 2,8-nonanediol, 3,4-nonanediol, 3,5-nonanediol, 3,6-nonanediol, 3,7-nonanediol, 4,5-nonanediol, 4,6-nonanediol, 1,2-cyclononanediol, 1,3-cyclononanediol, 1,4-cyclononanediol, 1,5-cyclononanediol, 1,2-decanediol, 1,3-decanediol, 1,4-decanediol, 1,5-decanediol, 1,6-decanediol, 1,7-decanediol, 1,8-decanediol, 1,9-decanediol, 1,10-decanediol, 2,3-decanediol, 2,4-decanediol, 2,5-decanediol, 2,6-decanediol, 2,7-decanediol, 2,8-decanediol, 2,9-decanediol, 3,4-decanediol, 3,5-decanediol, 3,6-decanediol, 3,7-decanediol, 3,8-decanediol, 4,5-decanediol, 4,6-decanediol, 4,7-decanediol, 5,6-decanediol, 1,2-cyclodecanediol, 1,3-cyclodecanediol, 1,4-cyclodecanediol, 1,5-cyclodecanediol, 1,6-cyclodecanediol, diethylene glycol, and triethylene glycol.

The polyhydric hydroxyl compound is even more preferably at least one compound selected from the following group:

1,2-propanediol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol and 3,4-hexanediol.

When there is a smaller amount of impurities (for example, acidic compounds, sulfates, chlorides, and heavy metals) that are contained in the (A) polyhydric hydroxyl compound, the effects of the present invention are further enhanced, and/or after completion of the reaction, at the time of separating and/or purifying the episulfide compound, unreacted epoxy compound, a compound produced as a result of substitution of a sulfur atom of the thiating agent with an oxygen atom, the thiating agent and the polyhydric hydroxyl compound, separation of impurities is not needed. Therefore, it is a beneficial effective method for obtaining the aforementioned compound with high purity. The content of the impurities is preferably 5000 ppm or less, more preferably 2000 ppm or less, and even more preferably 500 ppm or less.

The (B) epoxy compound of the present exemplary embodiment is a compound having an epoxy group. A single epoxy compound may be used alone, or plural kinds of epoxy compounds may be used in combination.

The epoxy equivalent (WPE, g/wq.) of the (B) epoxy compound is preferably 55 or greater, more preferably 70 or greater, and even more preferably 90 or greater. When the epoxy equivalent is 55 or greater, the vapor pressure of the epoxy compound in the standard state is high, and handling tends to become easier. When the epoxy equivalent is 70 or greater, there is a tendency that the production of a polymerization product of the episulfide compound can be suppressed, and from the same viewpoint, the epoxy equivalent is even more preferably 90 or greater. Since there is a tendency that heat resistance of a cured product formed from the episulfide compound thus produced is enhanced, the epoxy equivalent (WPE) is preferably 700 or less, more preferably 600 or less, and even more preferably 500 or less.

The (B) epoxy compound is not particularly limited as long as it is a compound having a three-membered ring ether skeleton, but since the time of reaction between the epoxy group and the thiating agent is further shortened, and productivity tends to increase, it is preferable that the epoxy compound have a monovalent group represented by the following formula (3), (4), (5) or (6) as a partial structure. Furthermore, since there is a tendency that the production of a polymerization product of the episulfide compound and the reaction between the thiating agent and the episulfide compound can be suppressed, it is more preferable that the epoxy compound have a partial structure represented by the following formula (3) or (4). From the same viewpoint, it is even more preferable that the (B) epoxy compound have a partial structure represented by formula (3). In the formulae, $R_1, R_2, R_3, R_4, R_5, R_6, R_7, R_8, R_9, R_{10}, R_{11}, R_{12}, R_{13}, R_{14}$ and $R_{15}$ each independently represent a hydrogen atom or an organic group having 1 to 10 carbon atoms.

[Chemical Formula 2]

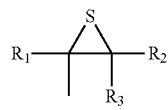

(3)

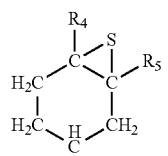

(4)

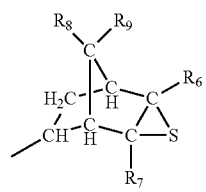

(5)

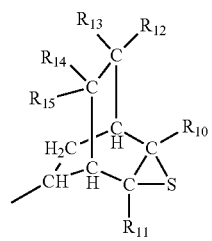

(6)

Specific examples of the (B) epoxy compound include a monofunctional epoxy compound, a polyfunctional epoxy compound which is a glycidyl etherification product of a polyphenol compound, an alicyclic epoxy compound, a polyfunctional epoxy compound which is a glycidyl etherification product of one of various novolac compounds, a nuclear-hydrogenated product of an aromatic epoxy compound, a heterocyclic epoxy compound, a glycidyl ester-based epoxy compound, a glycidylamine-based epoxy compound, an epoxy compound obtained by glycidylating a halogenated phenol, a sulfur-containing polyfunctional aliphatic epoxy compound, a silicone compound having an epoxy group in the molecule, and a heteropolymerizable substituent-containing epoxy compound. These may be used singly, or plural kinds may be used in combination.

(Monofunctional Epoxy Compound)

There are no particular limitations on the monofunctional epoxy compound, and specifically, the monofunctional epoxy compound can be selected from ethylene oxide, propylene oxide, 1-butene oxide, 2-butene oxide, butadiene oxide, butadiene diepoxide, cyclobutene oxide, 1,3-cyclobutadiene diepoxide, 1-pentene oxide, 2-pentene oxide, 1,3-pentadiene diepoxide, 1,4-pentadiene diepoxide, 2-methyl-2-butene oxide, 2-methyl-3-butene oxide, cyclopentene oxide, 1,3-cyclopentadiene diepoxide, 1-methylcyclobutene oxide, 3-methyl-1-cyclobutene oxide, 1-hexene oxide, 2-hexene oxide, 3-hexene oxide, 1,3-hexadiene diepoxide, 1,4-hexadiene diepoxide, 1,5-hexadiene diepoxide, 1,3,5-hexatriene triepoxide, cyclohexene oxide, 1,3-cyclohexadiene diepoxide, 1,3,5-cyclohexatriene triepoxide, 1-methylcyclopentene oxide, 3-methylcyclopentene oxide, 1-methyl-1,3-cyclopentadiene diepoxide, 2-methyl-1,3-cyclopentadiene diepoxide, 5-methyl-1,3-cyclopentadiene diepoxide, 3,4-dimethylcyclobutene oxide, 2,3-dimethylcyclobutene oxide, 1,2-dimethylcyclobutene oxide, 1,2-dimethyl-1,3-cyclobutadiene diepoxide, 2,3-dimethyl-1,3-cyclobutadiene diepoxide, 3,3-dimethyl-1,2-epoxybutane, 1-heptene oxide, 2-heptene oxide, 3-heptene oxide, 1,3-heptadiene diepoxide, 1,4-heptadiene diepoxide, 1,5-heptadiene diepoxide, 1,5-heptadiene diepoxide, 1,6-heptadiene diepoxide, 1,3,5-heptatriene triepoxide, 1,3,6-heptatriene triepoxide, 1,4,6-heptatriene triepoxide, cycloheptene oxide, 1-methyl-cyclohexene oxide, 3-methyl-cyclohexene oxide, 4-methyl-cyclohexene oxide, 1-methyl-1,3-cyclohexadiene diepoxide, 1-methyl-1,4-hexadiene diepoxide, 1-methyl-1,3,5-hexatriene triepoxide, 1,2-epoxy-5-hexene, 1,2-epoxy-4-vinylcyclohexene, 2-norbornene oxide, 7-methyl-2-norbornene oxide, 7,7-dimethyl-2-norbornene oxide, 2-methyl-2-norbornene oxide, 2,3-dimethyl-2-norbornene oxide, 2,7-dimethyl-2-norbornene oxide, 2,7,7-trimethyl-2-norbornene oxide, 2,3-epoxybicyclo[2,2,2]octane, 2,3-epoxy-2-methylbicyclo[2,2,2]octane, 2,3-epoxy-2,3-dimethylbicyclo[2,2,2]octane, 2,3-epoxy-2,5-dimethylbicyclo[2,2,2]octane, 2,3-epoxy-2,6-dimethylbicyclo[2,2,2]octane, 2,3-epoxy-2,3,5-trimethylbicyclo[2,2,2]octane, 2,3-epoxy-2,5,6-trimethylbicyclo[2,2,2]octane, 2,3-epoxy-2,3,5,6-tetramethylbicyclo[2,2,2]octane, dioctyl epoxyhexahydrophthalate, di-2-ethylhexyl epoxyhexahydrophthalate, stilbene oxide, phenyl glycidyl ether, 3-(2,2,3,3-tetrafluoropropoxy)-1,2-epoxypropane, pinene oxide, isoprene monoxide, 1,2-epoxyethylbenzene, naphthyl glycidyl ether, 3-(2-biphenyloxy)-1,2-epoxypropane, allyl glycidyl ether, 1,1-diphenylethylene oxide, glycidyl(meth)acrylate, glycidyl butyrate, iodomethyloxirane, 4-(2,3-epoxypropyl)morpholine, glycidyl methyl ether, 2-phenyl-propylene oxide, 2,3-epoxypropyl furfuryl ether, 2,3,4,5,6-pentafluorostyrene oxide, ethyl-3-phenyl glycidate, fosmidomycin, limonene oxide, epoxysuccinic acid, 3-glycidoxypropyltrimethoxysilane, (3-glycidoxypropyl)pentamethyldisiloxane, 3-glycidoxypropyl(methyl)dimethoxysilane, 3-glycidoxypropyl(methyl)diethoxysilane, 3-glycidoxypropyl(methyl)dibutoxysilane, 2-(3,4-epoxycyclohexyl)ethyl(methyl)dimethoxysilane, 2-(3,4-epoxycyclohexyl)ethyl(phenyl)diethoxysilane, 2,3-epoxypropyl(methyl)dimethoxysilane, 2,3-epoxypropyl(phenyl)dimethoxysilane, 3-glycidoxypropyltrimethoxysilane, 3-glycidoxypropyltriethoxysilane, 3-glycidoxypropyltributoxysilane, 2-(3,4-epoxycyclohexyl)ethyltrimethoxysilane, 2-(3,4-epoxycyclohexyl)ethyltriethoxysilane, 2,3-epoxypropyltrimethoxysilane, and 2,3-epoxypropyltriethoxysilane.

Among those described above, from the viewpoint that the vapor pressure in the standard state is high, handling is easy, and there is a tendency that the production of a polymerization product of the episulfide compound and the reaction between the thiating agent and the episulfide compound can be suppressed, it is preferable that the monofunctional epoxy compound be at least one compound selected from the following group:

ethylene oxide, propylene oxide, 1-butene oxide, 2-butene oxide, butadiene oxide, butadiene diepoxide, cyclobutene oxide, 1,3-cyclobutadiene diepoxide, 1-pentene oxide, 2-pentene oxide, 1,3-pentadiene diepoxide, 1,4-pentadiene diepoxide, 2-methyl-2-butene oxide, 2-methyl-3-butene oxide, cyclopentene oxide, 1,3-cyclopentadiene diepoxide, 1-methylcyclobutene oxide, 3-methyl-1-cyclobutene oxide, 1-hexene oxide, 2-hexene oxide, 3-hexene oxide, 1,3-hexadiene diepoxide, 1,4-hexadiene diepoxide, 1,5-hexadiene diepoxide, 1,3,5-hexatriene triepoxide, cyclohexene oxide, 1,3-cyclohexadiene diepoxide, 1,3,5-cyclohexatriene triepoxide, 1-methylcyclopentene oxide, 3-methylcyclopentene oxide, 1-methyl-1,3-cyclopentadiene diepoxide, 2-methyl-1,3-cyclopentadiene diepoxide, 5-methyl-1,3-cyclopentadiene diepoxide, 3,4-dimethylcyclobutene oxide, 2,3-dimethylcyclobutene oxide, 1,2-dimethylcyclobutene oxide, 1,2-dimethyl-1,3-cyclobutadiene diepoxide, 2,3-dimethyl-1,3-cyclobutadiene diepoxide, 3,3-dimethyl-1,2-epoxybutane, 1-heptene oxide, 2-heptene oxide, 3-heptene oxide, 1,3-heptadiene diepoxide, 1,4-heptadiene diepoxide, 1,5-heptadiene diepoxide, 1,5-heptadiene diepoxide, 1,6-heptadiene diepoxide, 1,3,5-heptatriene triepoxide, 1,3,6-heptatriene triepoxide, 1,4,6-heptatriene triepoxide, cycloheptene oxide, 1-methyl-cyclohexene oxide, 3-methyl-cyclohexene oxide, 4-methyl-cyclohexene oxide, 1-methyl-1,3-cyclohexadiene diepoxide, 1-methyl-1,4-hexadiene diepoxide, 1-methyl-1,3,5-hexatriene triepoxide, 1,2-epoxy-5-hexene, 1,2-epoxy-4-vinylcyclohexene, dioctyl epoxyhexahydrophthalate, di-2-ethylhexyl epoxyhexahydrophthalate, stilbene oxide, phenyl glycidyl ether, 3-(2,2,3,3-tetrafluoropropoxy)-1,2-epoxypropane, pinene oxide, isoprene monoxide, 1,2-epoxyethylbenzene, naphthyl glycidyl ether, 3-(2-biphenyloxy)-1,2-epoxypropane, allyl glycidyl ether, 1,1-diphenylethylene oxide, glycidyl(meth)acrylate, glycidyl butyrate, iodomethyloxirane, 4-(2,3-epoxypropyl)morpholine, glycidyl methyl ether, 2-phenyl-propylene oxide, 2,3-epoxypropyl furfuryl ether, 2,3,4,5,6-pentafluorostyrene oxide, ethyl-3-phenyl glycidate, fosmidomycin, limonene oxide, epoxysuccinic acid, 3-glycidoxypropyltrimethoxysilane, (3-glycidoxypropyl)pentamethyldisiloxane, 3-glycidoxypropyl(methyl)dimethoxysilane, 3-glycidoxypropyl(methyl)diethoxysilane, 3-glycidoxypropyl(methyl)dibutoxysilane, 2-(3,4-epoxycyclohexyl)ethyl(methyl)dimethoxysilane, 2-(3,4-epoxycyclohexyl)ethyl(phenyl)diethoxysilane, 2,3-epoxypropyl(methyl)dimethoxysilane, 2,3-epoxypropyl(phenyl)dimethoxysilane, 3-glycidoxypropyltrimethoxysilane, 3-glycidoxypropyltriethoxysilane, 3-glycidoxypropyltributoxysilane, 2-(3,4-epoxycyclohexyl)ethyltrimethoxysilane, 2-(3,4-epoxycyclohexyl)ethyltriethoxysilane, 2,3-epoxypropyltrimethoxysilane, and 2,3-epoxypropyltriethoxysilane.

Even more preferably, the monofunctional epoxy compound is at least one compound selected from the following group:

propylene oxide, 1-butene oxide, 2-butene oxide, butadiene oxide, butadiene diepoxide, 1-pentene oxide, 2-pentene oxide, 1,3-pentadiene diepoxide, 1,4-pentadiene diepoxide, 2-methyl-2-butene oxide, 2-methyl-3-butene oxide, cyclopentene oxide, 1-methylcyclobutene oxide, 3-methyl-1-cyclobutene oxide, 1-hexene oxide, 2-hexene oxide, 3-hexene oxide, 1,3-hexadiene diepoxide, 1,4-hexadiene diepoxide, 1,5-hexadiene diepoxide, 1,3,5-hexatriene triepoxide, cyclohexene oxide, 1,3-cyclohexadiene diepoxide, 1-methylcyclopentene oxide, 3-methylcyclopentene oxide, 2-heptene oxide, 3-heptene oxide, 1,3-heptadiene diepoxide, 1,4-heptadiene diepoxide, 1,5-heptadiene diepoxide, 1,5-heptadiene diepoxide, 1,6-heptadiene diepoxide, 1-methyl-cyclohexene oxide, 3-methyl-cyclohexene oxide, 4-methyl-cyclohexene oxide, 1,2-epoxy-5-hexene, 1,2-epoxy-4-vinylcyclohexene, stilbene oxide, phenyl glycidyl ether, 3-(2,2,3,3-tetrafluoropropoxy)-1,2-epoxypropane, pinene oxide, isoprene monoxide, 1,2-epoxyethylbenzene, naphthyl glycidyl ether, 3-(2-biphenyloxy)-1,2-epoxypropane, allyl glycidyl ether, 1,1-diphenyl-ethylene oxide, glycidyl(meth)acrylate, glycidyl butyrate, iodomethyloxirane, 4-(2,3-epoxypropyl)morpholine, glycidyl methyl ether, 2-phenyl-propylene oxide, 2,3-epoxypropyl-furfuryl ether, 2,3,4,5,6-pentafluorostyrene oxide, ethyl-3-phenyl glycidate, fosmidomycin, limonene oxide, epoxysuccinic acid, 3-glycidoxypropyltrimethoxysilane, (3-glycidoxypropyl)pentamethyldisiloxane, 3-glycidoxypropyl(methyl)dimethoxysilane, 3-glycidoxypropyl(methyl)diethoxysilane, 3-glycidoxypropyl(methyl)dibutoxysilane, 2-(3,4-epoxycyclohexyl)ethyl(methyl)dimethoxysilane, 2-(3,4-epoxycyclohexyl)ethyl(phenyl)diethoxysilane, 2,3-epoxypropyl(methyl)dimethoxysilane, 2,3-epoxypropyl(phenyl)dimethoxysilane, 3-glycidoxypropyltrimethoxysilane, 3-glycidoxypropyltriethoxysilane, 3-glycidoxypropyltributoxysilane, 2-(3,4-epoxycyclohexyl)ethyltrimethoxysilane, 2-(3,4-epoxycyclohexyl)ethyltriethoxysilane, 2,3-epoxypropyltrimethoxysilane, and 2,3-epoxypropyltriethoxysilane.

(Polyfunctional Epoxy Compound)

There are no particular limitations on the polyfunctional epoxy compound which is a glycidyl etherification product of a polyphenol compound, and specifically, the polyfunctional epoxy compound can be selected from glycidyl etherification products of polyphenol compounds such as bisphenol A, bisphenol F, bisphenol S, 4,4'-biphenol, tetramethylbisphenol A, dimethylbisphenol A, tetramethylbisphenol F, dimethylbisphenol F, tetramethylbisphenol S, dimethylbisphenol S, tetramethyl-4,4'-biphenyl, dimethyl-4,4'-biphenylphenol, 1-(4-hydroxyphenyl)-2-[4-(1,1-bis-(4-hydroxyphenyl)ethyl)phenyl]propane, 2,2'-methylenebis(4-methyl-6-t-butylphenol), 4,4'-butylidenebis(3-methyl-6-t-butylphenol), trishydroxyphenylmethane, resorcinol, hydroquinone, 2,6-di(t-butyl)hydroquinone, pyrogallol, phenols having a diisopropylidene skeleton, phenols having a 1,1-di(4-hydroxyphenyl)fluorene skeleton, and phenolated polybutadiene.

Among those described above, from the viewpoint of being available at low cost and having a tendency that the production of a polymerization product of the episulfide compound and the reaction between the thiating agent and the episulfide compound can be suppressed, polyfunctional epoxy compounds which are glycidyl etherification products of phenols having a bisphenol A skeleton or a bisphenol F skeleton are preferred.

Representative examples of the polyfunctional epoxy compounds which are glycidyl etherification products of phenols having a bisphenol skeleton are shown below.

[Chemical Formula 3]

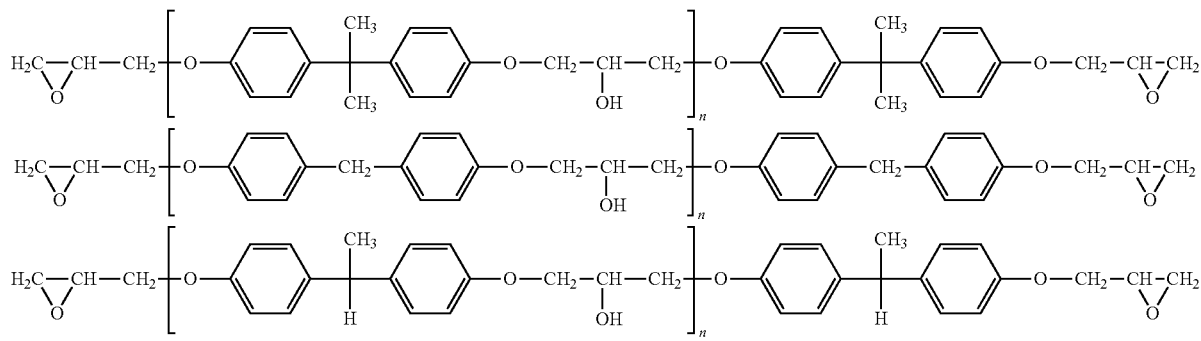

(Alicyclic Epoxy Compound)

The alicyclic epoxy compound is not particularly limited as long as it is an epoxy compound having an alicyclic epoxy group, and can be selected from, for example, epoxy compounds having a cyclohexene oxide group, a tricyclodecene oxide group or a cyclopentene oxide group.

Specific examples of the alicyclic epoxy compound include 3,4-epoxycyclohexenylmethyl-3',4'-epoxycyclohexene carboxylate, 3,4-epoxycyclohexylmethyl-3,4-epoxycyclohexane carboxylate, 3,4-epoxycyclohexyloctyl-3,4-epoxycyclohexane carboxylate, 2-(3,4-epoxycyclohexyl-5,5-spiro-3,4-epoxy)cyclohexane-meta-dioxane, bis(3,4-epoxycyclohexylmethyl) adipate, vinylcyclohexene dioxide, bis(3,4-epoxy-6-methylcyclohexylmethyl) adipate, 3,4-epoxy-6-methylcyclohexyl-3,4-epoxy-6-methylcyclohexane carboxylate, methylenebis(3,4-epoxycyclohexane), dicyclopentadiene diepoxide, ethylene glycol di(3,4-epoxycyclohexylmethyl) ether, ethylenebis(3,4-epoxycyclohexane carboxylate), and 1,2,8,9-diepoxylimonene. Other examples of the polyfunctional alicyclic epoxy compound include a 1,2-epoxy-4-(2-oxiranyl)cyclohexene adduct of 2,2-bis(hydroxymethyl)-1-butanol. Examples of commercially available products of the polyfunctional alicyclic epoxy compound include EPOLIDE GT401 and EHPE3150 (manufactured by Daicel Chemical Industries, Ltd.).

Representative examples of the alicyclic epoxy compound are shown below.

[Chemical Formula 4]

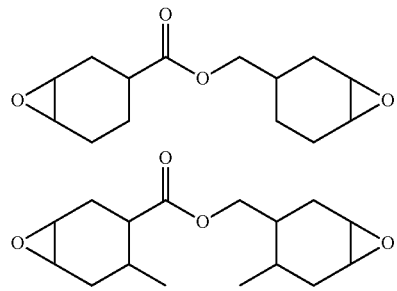

15
-continued
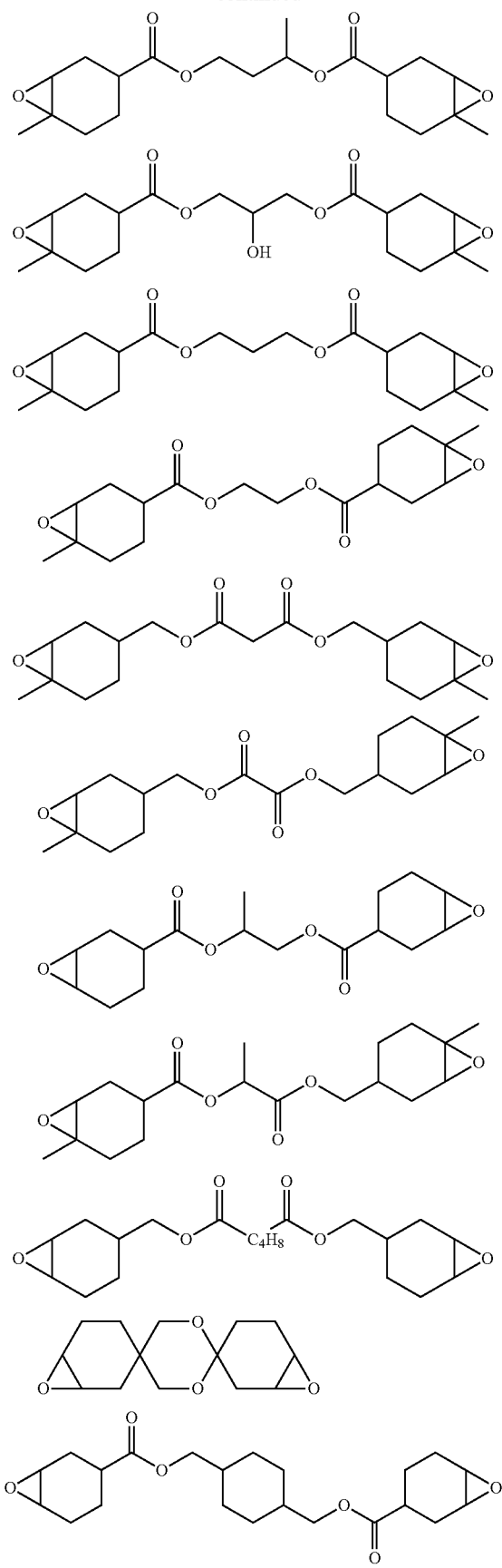
16
-continued
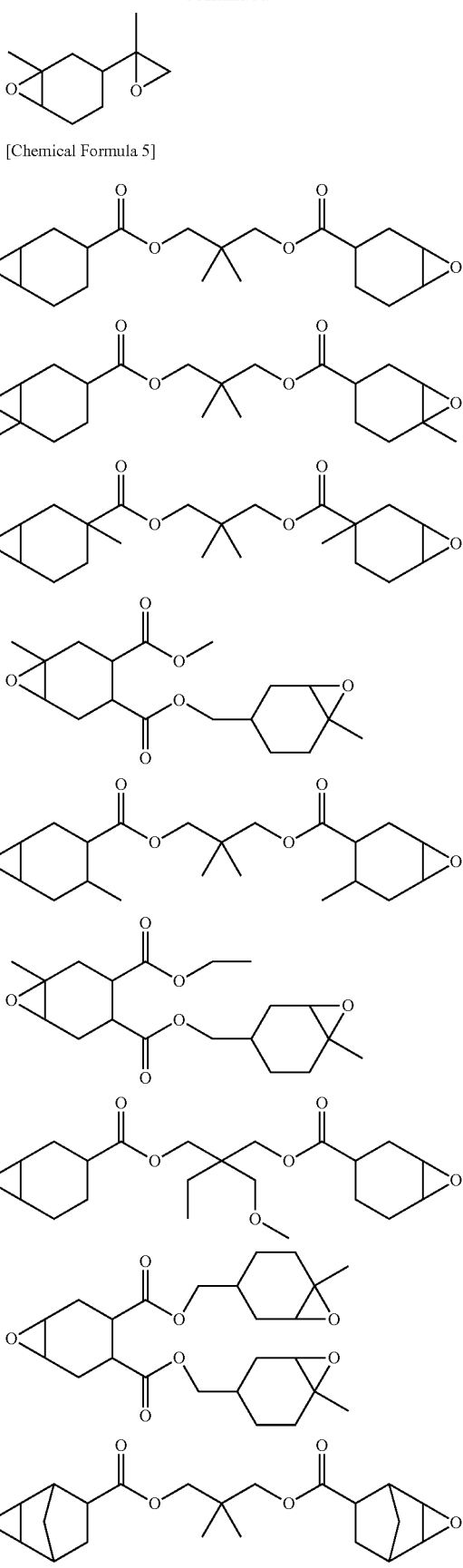
[Chemical Formula 5]

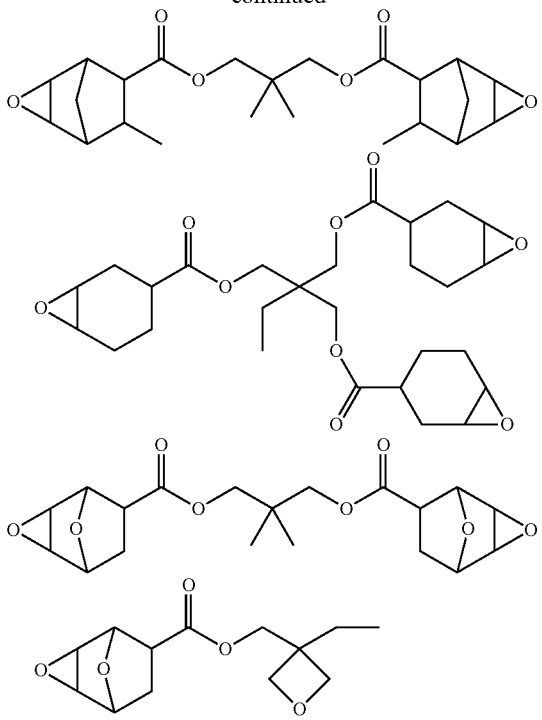

(Polyfunctional Epoxy Compound which is Glycidyl Etherification Product of Novolac Compound)

There are no particular limitations on the polyfunctional epoxy compound which is a glycidyl etherification product of a novolac compound, and the polyfunctional epoxy compound can be selected from, for example, glycidyl etherification products of various novolac compounds such as novolac compounds produced using various phenols such as phenol, cresols, ethylphenols, butylphenols, octylphenols, bisphenol A, bisphenol F, bisphenol S and naphthols as raw materials; xylylene skeleton-containing phenol novolac compounds, dicyclopentadiene skeleton-containing phenol novolac compounds, biphenyl skeleton-containing phenol novolac compounds, and fluorene skeleton-containing phenol novolac compounds.

Among those described above, from the viewpoint of being easily available, novolac compounds produced using phenol, cresols and the like as raw materials are preferred.

A representative example of the polyfunctional epoxy compound which is a glycidyl etherification product of a novolac compound is shown below.

[Chemical Formula 6]

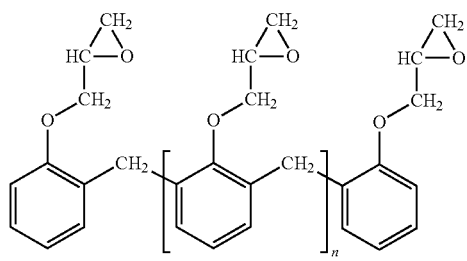

(Nuclear-Hydrogenated Product of Aromatic Epoxy Compound)

There are no particular limitations on the a nuclear-hydrogenated product of an aromatic epoxy compound, and the nuclear-hydrogenated compound can be selected from, for example, glycidyl etherification products of phenol compounds (bisphenol A, bisphenol F, bisphenol S, 4,4'-biphenol, and the like); products obtained by converting the aromatic rings of various phenols (phenol, cresols, ethylphenols, butylphenols, octylphenols, bisphenol A, bisphenol F, bisphenol S, naphthols, and the like); and a nuclear-hydrogenated products of glycidyl etherification products of novolac compounds.

(Heterocyclic Epoxy Compound)

There are no particular limitations on the heterocyclic epoxy compound, and the compound can be selected from, for example, heterocyclic epoxy compounds having heterocyclic rings such as an isocyanuric ring and a hydantoin ring.

(Glycidyl Ester-Based Epoxy Compound)

There are no particular limitations on the glycidyl ester-based epoxy compound, and the compound can be selected from, for example, epoxy compounds derived from carboxylic acid compounds, such as hexahydrophthalic acid digylcidyl ester and tetrahydrophthalic acid diglycidyl ester.

(Glycidylamine-Based Epoxy Compound)

There are no particular limitations on the glycidylamine-based epoxy compound, and the compound can be selected from, for example, epoxy compounds obtained by glycidylating amines such as aniline, toluidine, p-phenylenediamine, m-phenylenediamine, diaminodiphenylmethane derivatives and diaminomethylbenzene derivatives.

(Epoxy Compound Obtained by Glycidylating Halogenated Phenols)

There are no particular limitations on the epoxy compound obtained by glycidylating halogenated phenols, and the epoxy compound can be selected from, for example, epoxy compounds obtained by glycidyl etherifying halogenated phenols such as brominated bisphenol A, brominated bisphenol F, brominated bisphenol S, brominated phenol novolac, brominated cresol novolac, chlorinated bisphenol S and chlorinated bisphenol A.

(Sulfur-Containing Polyfunctional Aliphatic Epoxy Compound)

There are no particular limitations on the sulfur-containing polyfunctional aliphatic epoxy compound, and specifically, the aliphatic epoxy compound is selected from 1,1-bis(epoxyethyl)methane, 1-(epoxyethyl)-1-(β-epoxypropyl)methane, 1,1-bis(β-epoxypropyl)methane, 1-(epoxyethyl)-1-(β-epoxypropyl)ethane, 1,2-bis(β-epoxypropyl)ethane, 1-(epoxyethyl)-3-(β-epoxypropyl)butane, 1,3-bis(β-epoxypropyl)propane, 1-(epoxyethyl)-4-(β-epoxypropyl)pentane, 1,4-bis(β-epoxypropyl)butane, 1-(epoxyethyl)-5-(β-epoxypropyl)hexane, 1-(epoxyethyl)-2-(γ-epoxybutylthio)ethane, 1-(epoxyethyl)-2-[2-(γ-epoxybutylthio)ethylthio]ethane, tetrakis(β-epoxypropyl)methane, 1,1,1-tris(β-epoxypropyl)propane, 1,3-bis(β-epoxypropyl)-1-(β-epoxypropyl)-2-thiapropane, 1,5-bis(β-epoxypropyl)-2,4-bis(β-epoxypropyl)-3-thiapentane, 1,3- or 1,4-bis(epoxyethyl)cyclohexane, 1,3- or 1,4-bis(β-epoxypropyl)cyclohexane, 2,5-bis(epoxyethyl)-1,4-dithiane, 2,5-bis(β-epoxypropyl)-1,4-dithiane, 4-epoxy-1,2-cyclohexene oxide, 2,2-bis[4-(epoxyethyl)cyclohexyl]propane, 2,2-bis[4-(β-epoxypropyl)cyclohexyl]propane, bis[4-(epoxyethyl)cyclohexyl]methane, bis[4-(β-epoxypropyl)cyclohexyl]methane, bis[4-(β-epoxypropyl)cyclohexyl]sulfide, bis[4-(epoxyethyl)cyclohexyl]sulfide, bis(β-epoxypropyl) ether, bis(β-epoxypropyloxy)methane, 1,2-bis(β-epoxypropyloxy)ethane, 1,3-bis(β-epoxypropyloxy)propane, 1,2-bis(β-epoxypropyloxy)propane, 1-(β- epoxypropyloxy)-2-(β-epoxypropyloxymethyl)propane, 1,4-bis(β-epoxypropyloxy)butane, 1,3-bis(β-epoxypropyloxy)butane, 1-(β-epoxypropyloxy)-3-(β-epoxypropyloxymethyl)butane, 1,5-bis(β-epoxypropyloxy)pentane, 1-(β-epoxypropyloxy)-4-(β-epoxypropyloxymethyl)pentane, 1,6-bis(β-epoxypropyloxy)hexane, 1-(β-epoxypropyloxy)-5-(β-epoxypropyloxymethyl)hexane, 1-(β-epoxypropyloxy)-2-[(2-β-epoxypropyloxyethyl)oxy]ethane, 1-(β-epoxypropyloxy)-2-[[2-(2-β-epoxypropyloxyethyl) oxyethyl]oxy]ethane, tetrakis(β-epoxypropyloxymethyl) methane, 1,1,1-tris(β-epoxypropyloxymethyl)propane, 1,5-bis(β-epoxypropyloxy)-2-(β-epoxypropyloxymethyl)-3-thiapentane, 1,5-bis(β-epoxypropyloxy)-2,4-bis(β-epoxypropyloxymethyl)-3-thiapentane, 1-(β-epoxypropyloxy)-2,2-bis(β-epoxypropyloxymethyl)-4-thiahexane, 1,5,6-tris(β-epoxypropyloxy)-4-(β-epoxypropyloxymethyl)-3-thiahexane, 1,8-bis(β-epoxypropyloxy)-4-(β-epoxypropyloxymethyl)-3,6-dithiaoctane, 1,8-bis(β-epoxypropyloxy)-4,5-bis(β-epoxypropyloxymethyl)-3,6-dithiaoctane, 1,8-bis(β-epoxypropyloxy)-4,4-bis(β-epoxypropyloxymethyl)-3,6-dithiaoctane, 1,8-bis(β-epoxypropyloxy)-2,4,5-tris(β-epoxypropyloxymethyl)-3,6-dithiaoctane, 1,8-bis(β-epoxypropyloxy)-2,5-bis(β-epoxypropyloxymethyl)-3,6-dithiaoctane, 1,9-bis(β-epoxypropyloxy)-5-(β-epoxypropyloxymethyl)-5-[(2-β-epoxypropyloxyethyl)oxymethyl]-3,7-dithianonane, 1,10-bis(β-epoxypropyloxy)-5,6-bis[(2-β-epoxypropyloxyethyl)oxy]-3,6,9-trithiadecane, 1,11-bis(β-epoxypropyloxy)-4,8-bis(β-epoxypropyloxymethyl)-3,6,9-trithiaundecane, 1,11-bis(β-epoxypropyloxy)-5,7-bis(β-epoxypropyloxymethyl)-3,6,9-trithiaundecane, 1,11-bis(β-epoxypropyloxy)-5,7-[(2-β-epoxypropyloxyethyl)oxymethyl]-3,6,9-trithiaundecane, 1,11-bis(β-epoxypropyloxy)-4,7-bis(β-epoxypropyloxymethyl)-3,6,9-trithiaundecane, 1,3- or 1,4-bis(β-epoxypropyloxy)cyclohexane, 1,3- or 1,4-bis(β-epoxypropyloxymethyl)cyclohexane, bis[4-(β-epoxypropyloxy)cyclohexyl]methane, 2,2-bis[4-(β-epoxypropyloxy)cyclohexyl]propane, bis[4-(β-epoxypropyloxy)cyclohexyl]sulfide, 2,5-bis(β-epoxypropyloxymethyl)-1,4-dithiane, 2,5-bis(β-epoxypropyloxyethyloxymethyl)-1,4-dithiane, bis(β-epoxypropyl) sulfide, bis(β-epoxypropyl)disulfide, bis(β-epoxypropyl) trisulfide, bis(β-epoxypropylthio)methane, bis(β-epoxypropyldithio)methane, bis(β-epoxypropyldithio)ethane, bis(β-epoxypropyldithioethyl) sulfide, bis(β-epoxypropyldithioethyl)disulfide, 1,2-bis(β-epoxypropylthio)ethane, 1,3-bis(β-epoxypropylthio)propane, 1,2-bis(β-epoxypropylthio)propane, 1-(β-epoxypropylthio)-2-(β-epoxypropylthiomethyl)propane, 1,4-bis(β-epoxypropylthio)butane, 1,3-bis(β-epoxypropylthio)butane, 1-(β-epoxypropylthio)-3-(β-epoxypropylthiomethyl)butane, 1,5-bis(β-epoxypropylthio)pentane, 1-(β-epoxypropylthio)-4-(β-epoxypropylthiomethyl)pentane, 1,6-bis(β-epoxypropylthio)hexane, 1-(β-epoxypropylthio)-5-(β-epoxypropylthiomethyl)hexane, 1-(β-epoxypropylthio)-2-[(2-β-epoxypropylthioethyl)thio]ethane, 1-(β-epoxypropylthio)-2-[[2-(2-β-epoxypropylthiothioethyl]thio]ethane tetrakis(β-epoxypropylthiomethyl)methane, tetrakis(β-epoxypropyldithiomethyl)methane, 1,1,1-tris(β-epoxypropylthiomethyl)propane, 1,2,3-tris(β-epoxypropyldithio)propane, 1,5-bis(β-epoxypropylthio)-2-(β-epoxypropylthiomethyl)-3-thiapentane, 1,5-bis(β-epoxypropylthio)-2,4-bis(β-epoxypropylthiomethyl)-3-thiapentane, 1,6-bis(β-epoxypropyldithiomethyl)-2-(β-epoxypropyldithioethylthio)-4-thiahexane, 1-(β-epoxypropylthio)-2,2-bis(β-epoxypropylthiomethyl)-4-thiahexane, 1,5,6-tris(β-epoxypropylthio)-4-(β-epoxypropylthiomethyl)-3-thiahexane, 1,8-bis(β-epoxypropylthio)-4-(β-epoxypropylthiomethyl)-3,6-dithiaoctane, 1,8-bis(β-epoxypropylthio)-4,5-bis(β-epoxypropylthiomethyl)-3,6-dithiaoctane, 1,8-bis(β-epoxypropylthio)-4,4-bis(β-epoxypropylthiomethyl)-3,6-dithiaoctane, 1,8-bis(β-epoxypropylthio)-2,4,5-tris(β-epoxypropylthiomethyl)-3,6-dithiaoctane, 1,8-bis(β-epoxypropylthio)-2,5-bis(β-epoxypropylthiomethyl)-3,6-dithiaoctane, 1,9-bis(β-epoxypropylthio)-5-(β-epoxypropylthiomethyl)-5-[(2-β-epoxypropylthioethyl)thiomethyl]-3,7-dithianonane, 1,10-bis(β-epoxypropylthio)-5,6-bis[(2-β-epoxypropylthioethyl)thio]-3,6,9-trithiadecane, 1,11-bis(β-epoxypropylthio)-4,8-bis(β-epoxypropylthiomethyl)-3,6,9-trithiaundecane, 1,11-bis(β-epoxypropylthio)-5,7-bis(β-epoxypropylthiomethyl)-3,6,9-trithiaundecane, 1,11-bis(β-epoxypropylthio)-5,7-[(2-β-epoxypropylthioethyl)thiomethyl]-3,6,9-trithiaundecane, 1,11-bis(β-epoxypropylthio)-4,7-bis(β-epoxypropylthiomethyl)-3,6,9-trithiaundecane, tetra[2-(β-epoxypropylthio)acetylmethyl]methane, 1,1,1-tri[2-(β-epoxypropylthio)acetylmethyl]propane, tetra[2-(β-epoxypropylthiomethyl)acetylmethyl]methane, 1,1,1-tri[2-(β-epoxypropylthiomethyl)acetylmethyl]propane, 1,3- or 1,4-bis(β-epoxypropylthio)cyclohexane, 1,3- or 1,4-bis(β-epoxypropylthiomethyl)cyclohexane, 2,5-bis(β-epoxypropylthiomethyl)-1,4-dithiane, 2,5-bis(β-epoxypropyldithiomethyl)-1,4-dithiane, 2,5-bis(β-epoxypropylthioethylthiomethyl)-1,4-dithiane, bis[4-(β-epoxypropylthio)cyclohexyl]methane, 2,2-bis[4-(β-epoxypropylthio)cyclohexyl]propane, bis[4-(β-epoxypropylthio)cyclohexyl]sulfide, 2,2-bis[4-(β-epoxypropylthio)cyclohexyl]propane, and bis[4-(β-epoxypropylthio)cyclohexyl]sulfide.

Among those compounds described above, from the viewpoint that since production can be easily carried out, the cost of the episulfide compound thus obtainable can be suppressed, and economic efficiency is excellent, the sulfur-containing polyfunctional aliphatic epoxy compound is preferably at least one compound selected from the following group: bis(β-epoxypropyloxy)methane, 1,2-bis(β-epoxypropyloxy)ethane, 1,3-bis(β-epoxypropyloxy)propane, 1,2-bis(β-epoxypropyloxy)propane, 1-(β-epoxypropyloxy)-2-(β-epoxypropyloxymethyl)propane, 1,4-bis(β-epoxypropyloxy)butane, 1,3-bis(β-epoxypropyloxy)butane, 1-(β-epoxypropyloxy)-3-(β-epoxypropyloxymethyl)butane, 1,6-bis(β-epoxypropyloxy)hexane, 1-(β-epoxypropyloxy)-5-(β-epoxypropyloxymethyl)hexane, 1-(β-epoxypropyloxy)-2-[(2-β-epoxypropyloxyethyl)oxy]ethane, 1-(β-epoxypropyloxy)-2-[[2-(2-β-epoxypropyloxyethyl)oxyethyl]oxy]ethane, tetrakis(β-epoxypropyloxymethyl)methane, 1,1,1-tris(β-epoxypropyloxymethyl)propane, 1-(β-epoxypropyloxy)-2,2-bis(β-epoxypropyloxymethyl)-4-thiahexane, 1,5,6-tris(β-epoxypropyloxy)-4-(β-epoxypropyloxymethyl)-3-thiahexane, 1,8-bis(β-epoxypropyloxy)-4-(β-epoxypropyloxymethyl)-3,6-dithiaoctane, 1,8-bis(β-epoxypropyloxy)-4,5-bis(β-epoxypropyloxymethyl)-3,6-dithiaoctane, 1,8-bis(β-epoxypropyloxy)-4,4-bis(β-epoxypropyloxymethyl)-3,6-dithiaoctane, 1,8-bis(β-epoxypropyloxy)-2,4,5-tris(β-epoxypropyloxymethyl)-3,6-dithiaoctane, 1,8-bis(β-epoxypropyloxy)-2,5-bis(β-epoxypropyloxymethyl)-3,6-dithiaoctane, 1,3- or 1,4-bis(β-epoxypropyloxy)cyclohexane, 1,3- or 1,4-bis(β-epoxypropyloxymethyl)cyclohexane, bis[4-(β-epoxypropyloxy)cyclohexyl]methane, 2,2-bis[4-(β-epoxypropyloxy)cyclohexyl]propane, bis[4-(β-epoxypropyloxy)cyclohexyl]sulfide, 2,5-bis(β-epoxypropyloxymethyl)-1,4-dithiane, 2,5-bis(β-epoxypropyloxyethyloxymethyl)-1,4-dithiane, bis(β-epoxypropyl) sulfide, bis(β-epoxypropyl)disulfide, bis(β-epoxypropylthio) methane, bis(β-epoxypropyldithio) methane, bis(β-epoxypropyldithio)ethane, bis(β-epoxypropyldithioethyl)sulfide, bis(β-epoxypropyldithioethyl)disulfide, 1,2-bis(β-epoxypropylthio)ethane, 1,3-bis(β-epoxypropylthio)propane, 1,2-bis(β-epoxypropylthio)propane, 1-(β-epoxypropylthio)-2-(β-epoxypropylthiomethyl)propane, 1,4-bis(β-epoxypropylthio)butane, 1,3-bis(β-epoxypropylthio)butane, 1-(β-epoxypropylthio)-3-(β-epoxypropylthiomethyl)butane, 1,6-bis(β-epoxypropylthio)hexane, 1-(β-epoxypropylthio)-5-(β-epoxypropylthiomethyl)hexane, 1-(β-epoxypropylthio)-2-[(2-β-epoxypropylthioethyl)thio]ethane, 1-(β-epoxypropylthio)-2-[[2-(2-β-epoxypropylthioethyl)thioethyl]thio]ethane tetrakis(β-epoxypropylthiomethyl)methane, tetrakis(β-epoxypropyldithiomethyl)methane, 1,1,1-tris(β-epoxypropylthiomethyl)propane, 1,2,3-tris(β-epoxypropyldithio)propane, 1,6-bis(β-epoxypropyldithiomethyl)-2-(β-epoxypropyldithioethylthio)-4-thiahexane, 1-(β-epoxypropylthio)-2,2-bis(β-epoxypropylthiomethyl)-4-thiahexane, 1,5,6-tris(β-epoxypropylthio)-4-(β-epoxypropylthiomethyl)-3-thiahexane, 1,8-bis(β-epoxypropylthio)-4-(β-epoxypropylthiomethyl)-3,6-dithiaoctane, 1,8-bis(β-epoxypropylthio)-4,5-bis(β-epoxypropylthiomethyl)-3,6-dithiaoctane, 1,8-bis(β-epoxypropylthio)-4,4-bis(β-epoxypropylthiomethyl)-3,6-dithiaoctane, 1,8-bis(β-epoxypropylthio)-2,4,5-tris(β-epoxypropylthiomethyl)-3,6-dithiaoctane, 1,8-bis(β-epoxypropylthio)-2,5-bis(β-epoxypropylthiomethyl)-3,6-dithiaoctane, tetra[2-(β-epoxypropylthio)acetylmethyl]methane, 1,1,1-tri[2-(β-epoxypropylthio)acetylmethyl]propane, tetra[2-(β-epoxypropylthiomethyl)acetylmethyl]methane, 1,1,1-tri[2-(β-epoxypropylthiomethyl)acetylmethyl]propane, 1,3- or 1,4-bis(β-epoxypropylthio)cyclohexane, 1,3- or 1,4-bis(β-epoxypropylthiomethyl)cyclohexane, 2,5-bis(β-epoxypropylthiomethyl)-1,4-dithiane, 2,5-bis(β-epoxypropyldithiomethyl)-1,4-dithiane, 2,5-bis(β-epoxypropylthioethylthiomethyl)-1,4-dithiane, bis[4-(β-epoxypropylthio)cyclohexyl]methane, 2,2-bis[4-(β-epoxypropylthio)cyclohexyl]propane, bis[4-(β-epoxypropylthio)cyclohexyl]sulfide, 2,2-bis[4-(β-epoxypropylthio)cyclohexyl]propane, and bis[4-(β-epoxypropylthio)cyclohexyl]sulfide.

(Silicone Compound Having Epoxy Group in Molecule)

There are no particular limitations on the silicone compound having an epoxy group in the molecule, and the silicone compound can be selected from, for example, compounds represented by the following formula (7):

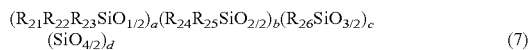

$(R_{21}R_{22}R_{23}SiO_{1/2})_a(R_{24}R_{25}SiO_{2/2})_b(R_{26}SiO_{3/2})_c$
$(SiO_{4/2})_d$ (7)

in formula (7), a, b, c and d respectively represent numbers satisfying the equation: a+b+c+d=1.0, while the following relations are satisfied: 0≤a/(a+b+c+d)≤1, 0≤b/(a+b+c+d)≤1, 0≤c/(a+b+c+d)≤1, and 0≤d/(a+b+c+d)<1; and at least one of $R_{21}$ to $R_{26}$ represents a group containing an epoxy group, and the others of $R_{21}$ to $R_{26}$ each represent a linear or branched hydrocarbon group having 1 to 8 carbon atoms, or a group obtained by fluorinating the relevant hydrocarbon group, while these may be identical with or different from each other.

(Heteropolymerizable Substituent-Containing Epoxy Compound)

There are no particular limitations on the heteropolymerizable substituent-containing epoxy compound, and the epoxy compound can be selected from, for example, compounds represented by the following formula (8):

[Chemical Formula 7]

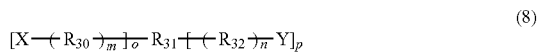

$[X\!-\!(\!-\!R_{30}\!-\!)_m\!-\!]_o\!-\!R_{31}\!-\![\!-\!(\!-\!R_{32}\!-\!)_n\!-\!Y]_p$ (8)

in formula (8), $R_{30}$ to $R_{32}$ each represent a substituted or unsubstituted, chain-like, branched or cyclic aliphatic or aromatic hydrocarbon group which may be thiated; m, n, o and p each independently represent a real number of 1 or greater; X represents an epoxy group; Y is selected, in the case of representing a single kind of a polymerizable substituent, from a cyclic ether structure, a cyclic thioether structure, a lactone structure, a cyclic carbonate structure and a sulfur-containing analogous structure thereof, a cyclic acetal structure and a sulfur-containing analogous structure thereof, a cyclic amine structure, a cyclic iminoether structure, a lactam structure, a cyclic thiourea structure, a cyclic phosphinate structure, a cyclic phosphonite structure, a cyclic phosphite structure, a vinyl structure, an allyl structure, a (meth)acrylic structure and a cycloalkane structure, and in the case of representing plural kinds of polymerizable substituents, Y represents at least two or more structures selected from the group described above.

When there is a smaller amount of impurities (for example, raw materials for producing the epoxy compound, chlorides, heavy metals, and sodium) that are contained in the (B) epoxy compound, the effects of the present invention are further enhanced, and/or after completion of the reaction, at the time of separating and/or purifying the episulfide compound, unreacted epoxy compound, a compound produced as a result of substitution of a sulfur atom of the thiating agent with an oxygen atom, the thiating agent and the polyhydric hydroxyl compound, separation of impurities is not needed. Therefore, it is a beneficial effective method for obtaining the aforementioned compound with high purity. The content of the impurities is preferably 5000 ppm or less, more preferably 2000 ppm or less, and even more preferably 500 ppm or less.

The (C) thiating agent of the present exemplary embodiment is not particularly limited as long as it is a compound which reacts with an epoxy group and produces an episulfide group. A single kind of thiating agent may be used alone, or plural kinds of thiating agents may be used in combination.

The (C) thiating agent preferably includes at least one compound selected from the group consisting of thiocyanates and thioureas. More preferably, the thiating agent is at least one or more compounds selected from the group consisting of sodium thiocyanate, potassium thiocyanate, ammonium thiocyanate and thiourea, and is even more preferably thiourea. Since thiocyanates and thioureas are easily available, economic efficiency tends to be excellent. Furthermore, when sodium thiocyanate, potassium thiocyanate, potassium thiocyanate, ammonium thiocyanate and thiourea, the reaction time is shortened, and there is a tendency that economic efficiency becomes excellent. Thus, from the same point of view, thiourea is particularly preferred.

Specific examples of the (C) thiating agent include lithium thiocyanate, sodium thiocyanate, potassium thiocyanate, rubidium thiocyanate, cesium thiocyanate, silver thiocyanate, cobalt(I) thiocyanate, mercury(II) thiocyanate, thallium(I)

thiocyanate, copper(I) thiocyanate, lead dithiocyanate, nickel dithiocyanate, barium dithiocyanate, ammonium thiocyanate, guanidine thiocyanate, thiourea, N,N'-dimethylthiourea, N,N,N',N'-tetramethylthiourea, N,N'-diethylthiourea, propylthiourea, N,N'-diisopropylthiourea, N,N'-dibutylthiourea, N-methyl-N'-(2-methyl-2-propenyl)thiourea, N-phenylthiourea, N,N'-diphenylthiourea, 1-methyl-2-imidazolidinethione, 1-benzyl-2-thiourea, N-(3,5-dimethylphenyl)thiourea, N-(2,6-dimethylphenyl)thiourea, N-(2,3-dimethylphenyl)thiourea, N-(2,4,6-trimethylphenyl)thiourea, N,N'-bis(2-methylphenyl)thiourea, N,N'-bis(3,5-dimethylphenyl)thiourea, N,N'-bis(2,6-dimethylphenyl)thiourea, N,N'-bis(2,4,6-trimethylphenyl)thiourea, N-(2-chlorophenyl)thiourea, N-(3-chlorophenyl)thiourea, N-(4-chlorophenyl)thiourea, N-(3,4-dichlorophenyl)thiourea, N-(3,5-dichlorophenyl)thiourea, N-(2,6-dichlorophenyl)thiourea, N-(2,4,6-trichlorophenyl)thiourea, N,N'-bis(2-chlorophenyl)thiourea, N,N'-bis(3,5-dichlorophenyl)thiourea, N,N'-bis(2,6-dichlorophenyl)thiourea, N-(2-fluorophenyl)thiourea, N-(3-fluorophenyl)thiourea, N-(4-fluorophenyl)thiourea, N-[2-(trifluoromethyl)phenyl]thiourea, N-[3-(trifluoromethyl)phenyl]thiourea, N-[4-(trifluoromethyl)phenyl]thiourea, N-(2,6-difluorophenyl)thiourea, N-(2,4-difluorophenyl)thiourea, N-(2,3-difluorophenyl)thiourea, N-(2,4,6-trifluorophenyl)thiourea, N,N'-bis(2-fluorophenyl)thiourea, N,N'-bis(2,6-difluorophenyl)thiourea, N,N'-bis(2,4,6-trifluorophenyl)thiourea, N-(2-cyanophenyl)thiourea, N-(3-cyanophenyl)thiourea, N-(4-cyanophenyl)thiourea, N-(3,5-dicyanophenyl)thiourea, N,N'-bis(4-cyanophenyl)thiourea, N,N'-bis(3,5-dicyanophenyl)thiourea, N-(2-methoxyphenyl)thiourea, N-(3-methoxyphenyl)thiourea, N-(4-methoxyphenyl)thiourea, N-(2,6-dimethoxyphenyl)thiourea, N-(3,5-dimethoxyphenyl)thiourea, N-(2,4,6-tridimethoxyphenyl)thiourea, N,N'-bis(4-methoxyphenyl)thiourea, N,N'-bis(2,6-dimethoxyphenyl)thiourea, N,N'-bis(2,4,6-tridimethoxyphenyl)thiourea, N-(2-nitrophenyl)thiourea, N-(3-nitrophenyl)thiourea, N-(4-nitrophenyl)thiourea, N-(3,5-dinitrophenyl)thiourea, and N,N'-bis(3,5-dinitrophenyl)thiourea.

When a support and a supported material having the thiating agent supported on the support are used, there are occasions in which the reaction time is shortened, the production of a polymerization product between the molecules of the episulfide compound and a reaction product between the episulfide compound and the thiating agent can be suppressed, the yield is increased, and after completion of the reaction, the operation at the time of separating the thiating agent is facilitated by separating the supported material. Meanwhile, the term supporting as used herein means attachment of the thiating agent onto the support or to the interior of the support, or exchange of an anionic atom or molecule with a thioisocyanate anion.

The support is not particularly limited as long as it is a generally used support, and specific examples thereof include silica (may have any shape such as a spherical shape, a granular shape or a scale-like shape, and may be acidic or neutral), alumina (may have any shape such as a spherical shape, an annular shape or a pellet shape, and may or may not be subjected to an activation treatment), and an ion exchange resin (for example, AMBERLYST™, AMBERLITE™, AMBERJET™, and DOW X™ manufactured by Dow Chemical Corp., polyvinylamine, and polyvinylpyridine).

When there is a smaller amount of impurities (for example, sulfates, chlorides, sulfides, copper, lead, iron, iodine, and sodium) that are contained in the (C) thiating agent, the effects of the present invention are further enhanced, and/or after completion of the reaction, at the time of separating and/or purifying the episulfide compound, unreacted epoxy compound, a compound produced as a result of substitution of a sulfur atom of the thiating agent with an oxygen atom, the thiating agent and the polyhydric hydroxyl compound, separation of impurities is not needed. Therefore, it is a beneficial effective method for obtaining the aforementioned compound with high purity. The content of the impurities is preferably 5000 ppm or less, more preferably 2000 ppm or less, and even more preferably 500 ppm or less.

On the occasion of the reaction between the (B) epoxy compound and the (C) thiating agent, the mixing rate of these agents can be represented by the mixing index $\alpha$ that is calculated by the following formula (1):

$$\text{Mixing index } \alpha = \alpha t / \alpha e \quad (1)$$

in formula (1), $\alpha t$ represents the amount of substance (mol) of sulfur atoms contained in the thiating agent, which atoms can be used in the production of episulfide groups; and $\alpha e$ represents the amount of substance (mol) of epoxy groups contained in the epoxy compound.

In the present exemplary embodiment, the mixing index $\alpha$ is preferably 1 or greater, more preferably 1.2 or greater, and even more preferably 1.5 or greater. When the mixing index $\alpha$ is 1 or greater, the time of reaction between the epoxy compound and the thiating agent is further shortened, and productivity tends to increase. When the mixing index $\alpha$ is 1.2 or greater, unreacted epoxy compound is decreased, and the yield of the episulfide compound tends to further increase. From the same viewpoint, the mixing index $\alpha$ is even more preferably 1.5 or greater.

The mixing index $\alpha$ is preferably 10 or less, more preferably 6 or less, and even more preferably 4 or less. When the mixing index $\alpha$ is 10 or less, since the thiating agent is not used in excess, economic efficiency tends to be excellent. Furthermore, when the mixing index $\alpha$ is 6 or less, the production of a reaction product between the episulfide compound and the thiating agent can be suppressed, and there is a tendency that the yield can be increased. From the same viewpoint, the mixing index $\alpha$ is even more preferably 4 or less.

The mixing rate of the (A) polyhydric hydroxyl compound and the (C) thiating agent at the time of the reaction between the (B) epoxy compound and the (C) thiating agent can be represented by the mixing index $\beta$ that is calculated by the following formula (2):

$$\text{Mixing index } \beta = \beta t / \beta o \quad (2)$$

in formula (2), $\beta t$ represents the mass (g) of the thiating agent, and $\beta o$ represents the mass (g) of the polyhydric hydroxyl compound.

In the present exemplary embodiment, the mixing index $\beta$ is preferably 0.010 or greater, more preferably 0.015 or greater, and even more preferably 0.020 or greater. When the mixing index $\beta$ is 0.010 or greater, the time of reaction of the epoxy compound is further shortened, and productivity tends to increase. When the mixing index $\beta$ is 0.015 or greater, since the amount of use of the polyhydric hydroxyl compound can be reduced, economic efficiency tends to be excellent. From the same viewpoint, the mixing index $\beta$ is even more preferably 0.020 or greater.

The mixing index $\beta$ is preferably 0.500 or less, more preferably 0.450 or less, and even more preferably 0.420 or less. When the mixing index $\beta$ is 0.500 or less, the time of reaction with the epoxy compound is further shortened, and productivity tends to increase. When the mixing index $\beta$ is 0.450 or less, the production of a polymerization product of the episulfide compound is suppressed, and the selectivity of the product tends to be superior. From the same viewpoint, the mixing index β is even more preferably 0.420 or less.

The reaction between the (B) epoxy compound and the (C) thiating agent is carried out in a reaction liquid containing the (A) polyhydric hydroxyl compound, the (B) epoxy compound, and the (C) thiating agent. When the reaction liquid is prepared, the (A) polyhydric hydroxyl compound, the (B) epoxy compound, and the (C) thiating agent may be added at any order. The respective compounds may be added all at once, or may be slowly added. In regard to preparation of the reaction liquid, a method of preparing a solution containing (A) a polyhydric hydroxyl compound and (C) a thiating agent, with these being uniformly mixed therein, and adding (B) an epoxy compound to this solution thereafter; or a method of adding this solution to (B) an epoxy compound, is particularly effective from the viewpoint of an increase in the yield of the episulfide compound, and stabilization of the reaction time.

When the reaction liquid further includes a solvent, the solvent may serve as an effective technique depending on the kind of the (B) epoxy compound and/or the (C) thiating agent.

There are no particular limitations on the solvent, but specific examples thereof include monovalent hydroxyl compounds such as water, methanol and ethanol; ethers such as diethyl ether, tetrahydrofuran and dioxane; hydroxyethers such as methyl cellosolve, ethyl cellosolve, and butyl cellosolve; nitriles such as acetonitrile, propionitrile, butyronitrile, valeronitrile, and benzonitrile; amides such as N,N-dimethylformamide and N,N-dimethylacetamide; sulfoxides such as dimethyl sulfoxide and dibutyl sulfoxide; and aromatic hydrocarbons such as benzene, toluene and xylene. These may be used singly, or plural kinds may be used in combination.

When the reaction liquid contains a reaction catalyst, it is an effective technique because the reaction time is further shortened. There are no particular limitations on the reaction catalyst, but examples thereof include organic catalysts and inorganic catalysts. These may be used singly, or plural kinds may be used in combination.

Specific examples of organic catalysts include trifluoromethanesulfonic acid, oxalic acid, p-toluenesulfonic acid, cyanuric acid chloride, ammonium acetate, methyl phosphite, ethyl phosphite, propyl phosphite, butyl phosphite, and β-dextrin. These may be used singly, or plural kinds may be used in combination.

Specific examples of inorganic catalysts include acidic ion exchange resins (for example, AMBERLITE™, AMBERJET™ and DOW X™ manufactured by Dow Chemical Corp.), supported materials in which aluminum chloride or tetrafluoroboric acid is supported on the aforementioned supports, activated alumina, trichlorotitanium(IV) trifluoromethanesulfonate, titanium(IV) oxytrifluoromethanesulfonate, iron(III) trifluoromethanesulfonate, aluminum(III) dodecanoate, ruthenium chloride, bismuth chloride, cerium ammonium nitrate, ammonium decatungstocerate(IV) icosahydrate, potassium dodecatungstocobaltate trihydrate, and tin(IV) tetraphenylporphyrinatotetrafluoroborate. These may be used singly, or plural kinds may be used in combination.

When the reaction catalyst is not included in the reaction liquid, after completion of the reaction, at the time of separating and/or purifying the episulfide compound, unreacted epoxy compound, a compound produced as a result of substitution of a sulfur atom of the thiating agent with an oxygen atom, the thiating agent and the polyhydric hydroxyl compound, separation of the reaction catalyst is not needed. Therefore, it is an effective method for obtaining the aforementioned compound with high purity.

When the reaction liquid contains an acid and/or an acid anhydride, it is an effective technique in view of increasing the yield because polymerization between the molecules of the episulfide compound may be further suppressed.

There are no particular limitations on the acid and acid anhydride, but specific examples thereof include nitric acid, hydrochloric acid, sulfuric acid, fuming sulfuric acid, boric acid, arsenic acid, phosphoric acid, hydrocyanic acid, acetic acid, peracetic acid, thioacetic acid, tartaric acid, propionic acid, oxalic acid, butyric acid, succinic acid, maleic acid, benzoic acid, anhydrous nitric acid, boron oxide, arsenic acid pentoxide, phosphorus pentoxide, anhydrous chromic acid, acetic anhydride, propionic anhydride, butyric anhydride, succinic anhydride, maleic anhydride, benzoic anhydride, phthalic anhydride, silica gel, silica alumina, and aluminum chloride. These may be used singly, or plural kinds may be used in combination.

When the reaction liquid contains an ammonium salt, it is an effective technique from the viewpoint of improving the working environment because when a foul odor occurs during the reaction, the foul odor can be suppressed.

There are no particular limitations on the ammonium salt, but specific examples thereof include ammonium chloride, ammonium bromide, ammonium iodide, ammonium formate, ammonium acetate, ammonium propionate, ammonium benzoate, ammonium sulfate, ammonium nitrate, ammonium carbonate, ammonium phosphate, and ammonium hydroxide. These may be used singly, or plural kinds may be used in combination.

When the (A) polyhydric hydroxyl compound and the (B) epoxy compound are not uniformly dissolved, a method of finely dispersing the polyhydric hydroxyl compound or the epoxy compound in the system is an effective technique because the reaction time of the epoxy compound is further shortened.

There are no particular limitations on the method for fine dispersion, and examples include, for example, a method of increasing the stirring intensity. Specifically, fine dispersion is achieved by appropriately setting the stirring method (a stirring blade type, a homogenizer, a high pressure homogenizer, an ultrahigh pressure homogenizer, an ultrasonic homogenizer, a Polytron homogenizer, and the like), the shape of the stirring blade (for example, fan, propeller, cross, butterfly, dragonfly, turbine, disc turbine, Disper, paddle, and oblique paddle), the stirring speed of the stirring blade, installation of baffles in the reaction tank, the shaft shape of the homogenizer (universal type, stirring type, multiple ultrasonic type, open type, closed type, and the like), and the like.

The reaction temperature (temperature of the reaction liquid) of the reaction between the (B) epoxy compound and the (C) thiating agent is preferably 0° C. or higher because there are occasions in which the solvent may coagulate depending on the selection of the solvent, and the reaction rate may decrease. Furthermore, from the viewpoint that the reaction time of the epoxy compound can be further shortened, the reaction temperature is more preferably 5° C. or higher, and even more preferably 10° C. or higher. The reaction temperature is preferably 100° C. or lower, from the viewpoint that the decomposition of the episulfide group is suppressed, and the yield of the product tends to increase. Furthermore, since the production of a polymerization product of the episulfide compound is suppressed, and the yield of the product tends to further increase, the reaction temperature is more preferably 80° C. or lower, and even more preferably 60° C. or lower.

It is not necessary that the reaction temperature be constant as long as the reaction temperature is in the range described above, and the temperature may be changed in the middle of the operation.

The reaction atmosphere is not particularly limited as long as it is an atmosphere that is generally used, but usually an air atmosphere, a nitrogen atmosphere, an argon atmosphere, and the like are used. Among these, from the viewpoint that there are occasions in which coloration of the reaction liquid can be suppressed, a nitrogen atmosphere and an argon atmosphere are preferred. Furthermore, from the viewpoint that economic efficiency tends to be excellent, a nitrogen atmosphere is more preferred.

The reaction pressure is not particularly limited, and usually, the reaction is carried out at atmospheric pressure. However, when the vapor pressure in the standard state of the (B) epoxy compound is low, and there is a possibility that the epoxy compound may volatilize during the reaction, application of a pressure higher than or equal to the atmospheric pressure serves as an effective means.

An episulfide compound of high purity and an epoxy compound of high purity can be obtained by carrying out, after completion of the reaction, a step of separating the episulfide compound or a mixture of the episulfide compound and the epoxy compound from the others; and in the case of a mixture of the episulfide compound and the epoxy compound, a step of separating these, and if necessary, a step of purifying the episulfide compound and/or the epoxy compound thus obtained.

Regarding the method of separating a reaction product including the episulfide compound or a mixture of the episulfide compound and the epoxy compound, and others from the reaction liquid, for example, a method of allowing the reaction liquid to stand still, and thereby separating the reaction product and others; a method of adding water to the reaction liquid, partitioning the mixture into two layers of the reaction product and an aqueous layer, and thereby separating the reaction product; and a method of adding a non-polar solvent and water to the reaction liquid, partitioning the mixture into two layers of a non-polar solvent layer and an aqueous layer, and extracting the reaction product from the non-polar solvent layer, are effective.

The non-polar solvent is not particularly limited as long as it is a conventionally used non-polar solvent, but specific examples thereof include aliphatic hydrocarbon compounds such as n-pentane, n-hexane, isohexane, n-heptane, n-octane, n-decane, cyclopentane, cyclohexane, cycloheptane, and cyclooctane; aromatic hydrocarbon compounds such as benzene, toluene, xylene, ethylbenzene, diethylbenzene, isopropylbenzene, naphthalene, tetralin and biphenyl; halogenated hydrocarbon compounds such as methylene chloride, chloroform, carbon tetrachloride, ethylene chloride, trichloroethane, tetrachloroethane, pentachloroethane, hexachloroethane, dichloroethylene, trichloroethylene, tetrachloroethylene, dichloropropane, trichloropropane, isopropyl chloride, butyl chloride, hexyl chloride, chlorobenzene, dichlorobenzene, trichlorobenzene, chlorotoluene, and chloronaphthalene; ether compounds such as diethyl ether, tetrahydrofuran, and dioxane; and hydroxyether compounds such as methyl cellosolve, ethyl cellosolve, and butyl cellosolve. These non-polar solvents may be used singly, or plural kinds may be used in combination.

A method of adding a salt compound to the reaction liquid, the two layers composed of the reaction product and water, or the two layers composed of a non-polar solvent layer and an aqueous layer, may serve as an effective technique for accelerating the separation of these two layers.

Specific examples of the salt compound include sodium chloride, potassium chloride, ammonium chloride, sodium hydrogen carbonate, sodium carbonate, and sodium thiosulfate. These salt compounds may be used singly, or plural kinds may be used in combination.

When the aqueous layer between the two layers composed of the reaction product and water or between the two layers composed of a non-polar solvent layer and an aqueous layer is removed, the reaction product or a non-polar solvent layer containing the reaction product can be obtained.

When the non-polar solvent in the non-polar solvent layer thus obtained is removed using an evaporator or the like, and the reaction product is concentrated, the content of the episulfide compound or a mixture of the episulfide compound and the epoxy compound in the reaction product can be increased.

Washing of the reaction product using an acidic aqueous solution may serve as an effective technique in view of enhancing stability of the reaction product.

The acidic aqueous solution is not particularly limited as long as it is a conventionally used acidic aqueous solution, but specific examples thereof include aqueous solutions of nitric acid, hydrochloric acid, sulfuric acid, boric acid, arsenic acid, phosphoric acid, hydrocyanic acid, peracetic acid, thioacetic acid, oxalic acid, tartaric acid, butyric acid, succinic acid, and maleic acid. These acidic aqueous solutions may be used singly, or plural kinds may be used in combination. These acidic aqueous solutions tend to exhibit their effect at pH 6 or lower, and a more effective range is pH 3 or less.

When the reaction product is dissolved in a hydrocarbon-based solvent, the solution is left to stand, and then a layer formed of a polymerization product of the episulfide compound is removed, it may be an effective technique as a method of increasing the purity of the episulfide compound.

The hydrocarbon-based solvent is not particularly limited as long as it is a conventionally used solvent, but specific examples thereof include aliphatic hydrocarbon compounds such as n-pentane, n-hexane, isohexane, n-heptane, n-octane, n-decane, cyclopentane, cyclohexane, cycloheptane and cyclooctane; aromatic hydrocarbon compounds such as benzene, toluene, xylene, ethylbenzene, diethylbenzene, isopropylbenzene, naphthalene, tetralin and biphenyl; and halogenated hydrocarbon compounds such as methylene chloride, chloroform, carbon tetrachloride, ethylene chloride, trichloroethane, tetrachloroethane, pentachloroethane, hexachloroethane, dichloroethylene, trichloroethylene, tetrachloroethylene, dichloropropane, trichloropropane, isopropyl chloride, butyl chloride, hexyl chloride, chlorobenzene, dichlorobenzene, trichlorobenzene, chlorotoluene, and chloronaphthalene. These hydrocarbon solvents may be used singly, or plural kinds may be used in combination.

When the episulfide compound or the mixture of the episulfide compound and the epoxy compound can be separated by distillation, a method of distilling the reaction liquid or the reaction product, and thereby obtaining the episulfide compound of higher purity and the epoxy compound is used as an effective technique for separation and/or purification. The distillation temperature and the distillation pressure are appropriately set based on the boiling point of the episulfide compound or the epoxy compound.

The distillation temperature is preferably 100° C. or lower, more preferably 80° C. or lower, and even more preferably 60° C. or lower. When the distillation temperature is 100° C. or lower, the decomposition reaction of the episulfide group can be suppressed, and the yield tends to further increase. When the distillation temperature is 80° C. or lower, the production of a polymerization product of the episulfide compound is suppressed, and the yield tends to further increase.

From the same viewpoint, the distillation temperature is even more preferably 60° C. or lower.

The distillation pressure is appropriately set depending on the distillation temperature, but when the distillation temperature is higher than 100° C., it is preferable to set the pressure to a pressure lower than the atmospheric pressure.

As a method for obtaining the episulfide compound of high purity and/or the epoxy compound from the reaction liquid or the reaction product, a technique called column chromatography is effective.

Column chromatography is a method of allowing a reaction liquid or reaction product dissolved in an organic solvent to infiltrate into a column packed with an inorganic material or an organic material, and causing the reaction liquid or reaction product to pass therethrough using a eluent, and specific examples include open column chromatography, flash column chromatography, high performance liquid chromatography (HPLC), gas permeation chromatography (GPC), and ion exchange column chromatography.

The organic solvent and the eluent are not particularly limited as long as they are conventionally used solvents, but specific examples thereof include saturated hydrocarbon compounds such as n-pentane, n-hexane, isohexane, n-heptane, n-octane, isooctane, n-nonane, n-decane, cyclopentane, cyclohexane, cycloheptane, and cyclooctane; aromatic hydrocarbon compounds such as benzene, toluene, xylene, ethylbenzene, diethylbenzene, isopropylbenzene, naphthalene, tetralin, and biphenyl; halogenated hydrocarbon compounds such as methylene chloride, chloroform, carbon tetrachloride, ethylene chloride, trichloroethane, tetrachloroethane, pentachloroethane, hexachloroethane, dichloroethylene, trichloroethylene, tetrachloroethylene, dichloropropane, trichloropropane, isopropyl chloride, butyl chloride, hexyl chloride, chlorobenzene, dichlorobenzene, trichlorobenzene, chlorotoluene, and chloronaphthalene;

alcohols such as methanol, ethanol, propanol, isopropanol, butanol, isobutanol, pentanol, hexanol, heptanol, octanol, nonanol, decanol, undecanol, dodecanol, cyclohexanol, and benzyl alcohol; ethers such as ethyl ether, dichloroethyl ether, isopropyl ether, butyl ether, hexyl ether, methyl phenyl ether, ethyl phenyl ether, butyl phenyl ether, dioxane, trioxane, and tetrahydrofuran; ketones such as acetone, methylacetone, ethyl methyl ketone, methyl propyl ketone, methyl butyl ketone, methyl isobutyl ketone, methyl hexyl ketone, diethyl ketone, ethyl butyl ketone, dipropyl ketone, diisobutyl ketone, and cyclohexanone; and esters such as ethyl acetate, propyl acetate, butyl acetate, isobutyl acetate, pentyl acetate, hexyl acetate, octyl acetate, cyclohexyl acetate, methyl propionate, ethyl propionate, butyl propionate, methyl benzoate, ethyl benzoate, propyl benzoate, butyl benzoate, and benzyl benzoate. These organic solvents and eluents may be used singly, or plural kinds may be used in combination.

The inorganic material that is used as a packing agent for column chromatography is not particularly limited as long as it is a conventionally used inorganic material, but specific examples thereof include silica gel, chemically modified silica gel, alumina, zirconia, and hydroxyapatite.

The organic material that is used as a packing agent for column chromatography is not particularly limited as long as it is a conventionally used organic material, but specific examples thereof include a styrene-divinylbenzene copolymer, polymethacrylate, polyhydroxymethacrylate, polyvinyl alcohol, activated carbon for OH-form adsorption, Cr metal-impregnated carbon, gaseous layer mercaptan-adsorbed carbon, and alkali-impregnated carbon.

Among these packing agents, from the viewpoint that separation can be achieved with higher resolution, an inorganic material is preferred, and silica gel is even more preferred.

When the packing agent is silica gel, the average particle size of this silica gel is not particularly limited, but from the viewpoint that there is a tendency that materials other than the episulfide compound and/or the epoxy compound can be effectively removed, the average particle size of the silica gel is preferably 600 μm or less, more preferably 500 μm or less, and even more preferably 400 μm or less. Since the load of a pump required in order to cause the eluent to flow through the column can be reduced, and a stable flow rate can be controlled, the average particle size is preferably 5 μm or greater, more preferably 10 μm or greater, and even more preferably 20 μm or greater. The pore volume of silica gel is not particularly limited, but from the viewpoint of increasing the strength of the packing agent and suppressing disintegration of the packing agent due to the pressure occurring as a result of the eluent to flow through, the pore volume is preferably 5 mL/mL or less, more preferably 3 mL/mL or less, and even more preferably 1 mL/mL or less. The pore volume of silica gel is preferably 0.1 mL/mL or greater, more preferably 0.3 mL/mL or greater, and even more preferably 0.5 mL/mL or greater, since there is a tendency that materials other than the episulfide compound and/or the epoxy compound can be effectively removed. The specific surface area of silica gel is not particularly limited, but since there is a tendency that materials other than the episulfide compound and/or the epoxy compound can be effectively removed, the specific surface area is preferably 100 $m^2/g$ or greater, more preferably 200 $m^2/g$ or greater, and even more preferably 300 $m^2/g$ or greater. Since there is a tendency that the load of a pump required to allow the eluent to flow through the column can be reduced, and the flow rate can be stably controlled, the specific surface area of silica gel is preferably 5000 $m^2/g$ or less, more preferably 4000 $m^2/g$ or less, and even more preferably 3000 $m^2/g$ or less.

In regard to column chromatography, the ratio of the column length (L) and the column diameter (D), L/D, is not particularly limited, but the ratio is preferably 0.01 or greater, more preferably 0.03 or greater, and even more preferably 0.05 or greater. When the ratio L/D is 0.01 or greater, there is a tendency that materials other than the episulfide compound and/or epoxy compound can be effectively removed. The ratio L/D is preferably 1000 or less, more preferably 700 or less, and even more preferably 500 or less. When the ratio L/D is 1000 or less, there is a tendency that the chance for the episulfide compound and/or epoxy compound to react with the packing agent inside the column can be decreased.

There are no particular limitations on the flow rate per minute (linear velocity, cm/min) of the eluent that passes through the column, but from the viewpoint controlling a stable flow rate, the flow rate per minute is preferably 0.1 cm/min or greater, more preferably 0.15 cm/min or greater, and even more preferably 0.2 cm/min or greater. When the flow rate is large, the load of a pump required to allow the eluent to flow through the column increases. Therefore, the flow rate per minute is preferably 10,000 cm/min or less, more preferably 5,000 cm/min or less, and even more preferably 2,000 cm/min or less. The temperature at which column chromatography is performed is not particularly limited; however, since the eluent congeals depending on the selection of the eluent, and the load of a pump required to allow the eluent to flow through the column increases, the temperature is preferably 0° C. or higher, more preferably 5° C. or higher, and even more preferably 10° C. or higher. Since there is a tendency that the chance for the episulfide compound and/or epoxy compound to react with the packing agent inside the column can be reduced, the temperature at which column chromatography is performed is preferably 100° C. or lower, more preferably 80° C. or lower, and even more preferably 60° C. or lower.

The epoxy compound obtained by the separation and/or purification as described above can be reutilized in a process of thiating epoxy groups of (B) an epoxy compound by a reaction with (C) a thiating agent, in the presence of (A) a polyhydric hydroxyl compound having two or more hydroxyl groups. This operation is an effective technique because the amount of the epoxy compound as a waste material is reduced, and the cost needed for the production of the episulfide compound can be lowered.

The polyhydric hydroxyl compound contained in the residue when the reaction product is separated from the reaction liquid, the polyhydric hydroxyl compound contained in the aqueous layer obtainable by extraction, and the polyhydric hydroxyl compound contained in the distillation residue when the episulfide compound or a mixture of the episulfide compound and the epoxy compound is distilled, can be separated from the other components by performing operations such as distillation and/or column chromatography.

The distillation temperature and distillation pressure for separating the polyhydric hydroxyl compound are appropriately set according to the boiling point of the polyhydric hydroxyl compound. The distillation temperature is not particularly limited as long as the temperature is in a conventionally used range; however, from the viewpoint of controlling the production cost, the distillation temperature is preferably 300° C. or lower, more preferably 250° C. or lower, and even more preferably 200° C. or lower. The distillation pressure is not particularly limited as long as the pressure is in a conventionally used range, and the distillation pressure can be appropriately set to an increased pressure, a normal pressure, or a reduced pressure. However, when the distillation temperature is greater than the preferred range described above, it is preferable to reduce the pressure.

Column chromatography can be carried out by a method such as described above.

Furthermore, when it is intended to purify the polyhydric hydroxyl compound obtainable by the separation operation into a high purity compound, it may be effective to repeatedly perform the separation operations such as distillation and column chromatography.

The polyhydric hydroxyl compound thus separated can be reutilized in a process of thiating epoxy groups of (B) an epoxy compound by a reaction with (C) a thiating agent in the presence of (A) a polyhydric hydroxyl compound having two or more hydroxyl groups. This operation is an effective means since the amount of disposal of the polyhydric hydroxyl compound is decreased, and the cost needed for the production of the episulfide compound may be lowered.

By carrying out a process of separating a compound produced as a result of the substitution of a sulfur atom of the thiating agent with an oxygen atom, or a compound mixture of the relevant compound and the thiating agent from the other compounds; and in the case of having a mixture of a compound produced as a result of the substitution of a sulfur atom of the thiating agent with an oxygen atom and the thiating agent, a process of separating those compounds, and if necessary, a process of purifying a thiating agent produced as a result of the substitution of a sulfur atom of the thiating agent with an oxygen atom, and/or the thiating agent, a compound produced as a result of the substitution of a sulfur atom of the thiating agent with an oxygen atom, and the thiating agent can be obtained.

A residue obtained after the reaction product is separated from the reaction liquid, an aqueous layer obtainable by extraction, a residue obtainable when the episulfide compound or a mixture of the episulfide compound and the epoxy compound is distilled, and a compound produced as a result of the substitution of a sulfur atom of the thiating agent with an oxygen atom, which compound is contained in the residue obtainable when the polyhydric hydroxyl compound is distilled, or a mixture of the relevant compound and the thiating agent, can be separated from the other components by carrying out an operation such as distilling-off or precipitation.

The distill-off temperature and the distill-off pressure are appropriately set based on the boiling points of the components other than the compound produced as a result of the substitution of a sulfur atom of the thiating agent with an oxygen atom, or a mixture of the relevant compound and the thiating agent.

The distill-off temperature is not particularly limited as long as the temperature is in a conventionally used range, but from the viewpoint of suppressing thermal decomposition of the compound produced as a result of the substitution of a sulfur atom of the thiating agent with an oxygen atom, and the thiating agent, the distill-off temperature is preferably 250° C. or lower, more preferably 200° C. or lower, and even more preferably 150° C. or lower.

The distill-off pressure is not particularly limited as long as the pressure is in a conventionally used range, and the pressure can be appropriately set to an increased pressure, a normal pressure, or a reduced pressure. However, when the distill-off pressure is greater than the preferred range described above, it is preferable to reduce the pressure.

In regard to the residue obtained after the reaction product is separated from the reaction liquid, the aqueous layer obtainable by extraction, the residue obtainable when the episulfide compound or a mixture of the episulfide compound and the epoxy compound is distilled, or the residue obtainable when the polyhydric hydroxyl compound is distilled, after a solvent is added to the residue as necessary to obtain a solution, a compound produced as a result of the substitution of a sulfur atom of the thiating agent with an oxygen atom, and/or the thiating agent can be separated by causing the compound to precipitate out, by utilizing the difference in solubility depending on temperature, the decrease in solubility caused by concentration of the solution, addition of another solvent or the like, or the common ion effect.

When a mixture of a compound produced as a result of the substitution of a sulfur atom of the thiating agent with an oxygen atom and the thiating agent has precipitated out, the compound produced as a result of the substitution of a sulfur atom of the thiating agent with an oxygen atom can be separated from the thiating agent by performing the above-described precipitation operation again.

The conditions used to utilize precipitation can be appropriately adjusted from general conditions, by any person having ordinary skill in the art. For example, a separation operation based on precipitation can be carried out with reference to the methods illustrated as examples in Shin Jikken Kagaku Kouza (New Lectures on Experimental Science) (Maruzen Co., Ltd.), Yuki Kessho Sakusei Handobukku (Handbook of Organic Crystal Production) (Maruzen Co., Ltd.), and Yuki Kagobutsu Kessho Sakusei Handobukku, Genri to Nohau (Handbook on Organic Compound Crystal Production: Principle and Know-how) (Maruzen Co., Ltd.). Furthermore, precipitation can be utilized by changing the conditions such as temperature, pressure, solvent and additives, with reference to the methods illustrated as examples in the literatures described above.

Furthermore, in order to purify the compound produced as a result of the substitution of a sulfur atom of the thiating agent with an oxygen atom, which is obtainable by the separation operation described above, and/or the thiating agent, to obtain a high purity compound or agent, it may be an effective means to carry out the separation operations such as distilling-off and precipitation repeatedly.

The thiating agent can be regenerated by carrying out a process of regenerating the compound produced as a result of the substitution of a sulfur atom of the thiating agent with an oxygen atom, or a mixture of the relevant compound with the thiating agent, into the thiating agent.

The method for regenerating the thiating agent is not particularly limited as long as the method is a general method, and regeneration can be carried out with reference to, for example, the methods illustrated as examples in Faming Zhuanli Shenqing Gongkai Shuomingshu (2009), CN 101602702; Huaxue Gongye Yu Gongcheng (Tianjin, China) 2006, 23, 407-410.; and Journal of Sulfur Chemistry 2005, 26, 155-161. Furthermore, regeneration can be utilized by changing the conditions such as temperature, pressure, solvent and additives, with reference to the methods illustrated as examples in the literatures described above.

In the case of utilizing, as a method for regenerating the thiating agent, a method of allowing a compound having a 1,3,2,4-dithiadiphosphetane-2,4-disulfide skeleton represented by the following formula (9) to react with a compound produced as a result of the substitution of a sulfur atom of the thiating agent with an oxygen atom, or a mixture of the compound and the thiating agent, specific examples of the compound represented by formula (9) include compounds described in Tetrahedron 1985, 41, 5061-5087; J. Chem. Soc., Dalton Trans., 2000, 1533-1543; and Synthesis 2003, 1929-1958.

[Chemical Formula 8]

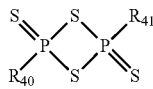

(9)

in the formula, $R_{40}$ and $R_{41}$ each represent an organic group having 1 to 20 carbon atoms, and may be identical with or independent from each other.

The thiating agent thus regenerated can be reutilized in the process of thiating epoxy groups of (B) an epoxy compound by a reaction with (C) a thiating agent in the presence of (A) a polyhydric hydroxyl compound having two or more hydroxyl groups. This operation is an effective means since the amount of disposal of a compound produced as a result of the substitution of a sulfur atom of the thiating agent with an oxygen atom, or the thiating agent is reduced, and the cost needed for the production of the episulfide compound may be lowered.

The episulfide compound thus obtained can be produced into a polymerization product by performing polymerization with heating or heat removal, in the presence of a polymerization catalyst, or by performing polymerization by irradiation with an energy line. Furthermore, when the episulfide compound has two or more episulfide groups, a cured product can be obtained by the same method.

Specific examples of a curing catalyst that is used for the polymerization with heating or heat removal include compounds of (1) to (11) as described below.

(1) Primary amines such as ethylamine, n-propylamine, sec-propylamine, n-butylamine, sec-butylamine, i-butylamine, tert-butylamine, pentylamine, hexylamine, heptylamine, octylamine, decylamine, laurylamine, myristylamine, 1,2-dimethylhexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxyl)propylamine, aminocyclopentane, aminocyclohexane, aminonorbornene, aminomethylcyclohexane, aminobenzene, benzylamine, phenethylamine, α-phenylethylamine, naphthylamine and furfurylamine;

primary polyamines such as ethylendiamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl) ether, 1,2-bis-(3-aminopropoxyl)ethane, 1,3-bis-(3-aminopropoxy)-2,2'-dimethylpropane, aminoethylethanolamine, 1,2-bisaminocyclohexane, 1,3-bisaminocyclohexane, 1,4-bisaminocyclohexane, 1,3-bisaminomethylcyclohexane, 1,4-bisaminomethylcyclohexane, 1,3-bisaminoethylcyclohexane, 1,4-bisaminoethylcyclohexane, 1,3-bisaminopropylcyclohexane, 1,4-bisaminopropylcyclohexane, hydrogenated 4,4'-diaminodiphenylmethane, 2-aminopiperidine, 4-aminopiperidine, 2-aminomethylpiperidine, 4-aminomethylpiperidine, 2-aminoethylpiperidine, 4-aminoethylpiperidine, N-aminoethylpiperidine, N-aminopropylpiperidine, N-aminoethylmorpholine, N-aminopropylmorpholine, isophoronediamine, methanediamine, 1,4-bisaminopropylpiperazine, o-phenylenediamine, m-phenylenediamine, p-phenylenediamine, 2,4-tolylenediamine, 2,6-tolylenediamine, 2,4-toluenediamine, m-aminobenzylamine, 4-chloro-o-phenylenediamine, tetrachloro-p-xylenediamine, 4-methoxy-6-methyl-m-phenylenediamine, m-xylenediamine, p-xylenediamine, 1,5-naphthalenediamine, 2,6-naphthalenediamine, benzidine, 4,4'-bis(o-toluidine), dianisidine, 4,4'-diaminodiphenylmethane, 2,2-(4,4'-diaminodiphenyl)propane, 4,4'-diaminodiphenyl ether, 4,4'-thiodianiline, 4,4'-diaminodiphenylsulfone, 4,4'-diaminoditolylsulfone, methylenebis(o-chloroaniline), 3,9-bis(3-aminopropyl)-2,4,8,10-tetraoxaspiro[5,5]undecane, diethylenetriamine, iminobispropylamine, methyliminobispropylamine, bis(hexamethylene)triamine, triethylenetetramine, tetraethylenepentamine, pentaethylenehexamine, N-aminoethylpiperazine, N-aminopropylpiperazine, 1,4-bis (aminoethylpiperazine), 1,4-bis(aminopropylpiperazine), 2,6-diaminopyridine, and bis(3,4-diaminophenyl)sulfone;

secondary amines such as diethylamine, dipropylamine, di-n-butylamine, di-sec-butylamine, diisobutylamine, di-n-pentylamine, di-3-pentylamine, dihexylamine, octylamine, di(2-ethylhexyl)amine, methylhexylamine, diallylamine, pyrrolidine, piperidine, 2-picoline, 3-picoline, 4-picoline, 2,4-lutidine, 2,6-lutidine, 3,5-lutidine, diphenylamine, N-methylaniline, N-ethylaniline, dibenzylamine, methylbenzylamine, dinaphthylamine, pyrrole, indoline, indole, and morpholine;

secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2- diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-piperidyl)butane, and tetramethylguanidine;

tertiary amines such as trimethylamine, triethylamine, tri-n-propylamine, triisopropylamine, tri-1,2-dimethylpropylamine, tri-3-methoxypropylamine, tri-n-butylamine, triisobutylamine, tri-sec-butylamine, tripentylamine, tri-3-pentylamine, tri-n-hexylamine, tri-n-octylamine, tri-2-ethylhexylamine, tridodecylamine, trilaurylamine, dicyclohexylethylamine, cyclohexyldiethylamine, tricyclohexylamine, N,N-dimethylhexylamine, N-methyldihexylamine, N,N-dimethylcyclohexylamine, N-methyldicyclohexylamine, N,N-diethylethanolamine, N,N-dimethylethanolamine, N-ethyldiethanolamine, triethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenol, N,N-dimethylaniline, N,N-diethylaniline, pyridine, quinoline, N-methylmorpholine, N-methylpiperidine, and 2-(2-dimethylaminoethoxy)-4-methyl-1,3,2-dioxabornane;

tertiary polyamines such as tetramethylethylenediamine, pyrazine, N,N'-dimethylpiperazine, N,N'-bis((2-hydroxy)propyl)piperazine, hexamethylenetetramine, N,N,N',N'-tetramethyl-1,3-butanamine, 2-dimethylamino-2-hydroxypropane, diethylaminoethanol, N,N,N-tris(3-dimethylaminopropyl)amine, 2,4,6-tris(N,N-dimethylaminomethyl)phenol, and heptamethylisobiguanide;

various imidazoles such as imidazole, N-methylimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2'-cyanoethyl)-2-undecylimidazole, N-(2'-cyanoethyl)-2-phenylimidazole, 3,3-bis-(2-ethyl-4-methylimidazolyl)methane, an adduct of alkylimidazole and isocyanuric acid, and a condensate of alkylimidazole and formaldehyde; amidines such as 1,8-diazabicyclo(5,4,0)undecene-7,1,5-diazabicyclo(4,3,0)nonene-5,6-dibutylamino-1,8-diazabicyclo(5,4,0) undecene-7; amine compounds represented by the above compounds.

(2) Complexes between the amines of (1), borane and boron trifluoride.

(3) Phosphines such as trimethylphosphine, triethylphosphine, triisopropylphosphine, tri-n-butylphosphine, tri-n-hexylphosphine, tri-n-octylphosphine, tricyclohexylphosphine, triphenylphosphine, tribenzylphosphine, tris(2-methylphenyl)phosphine, tris(3-methylphenyl)phosphine, tris(4-methylphenyl)phosphine, tris(diethylamino)phosphine, tris(4-methylphenyl)phosphine, dimethylphenylphosphine, diethylphenylphosphine, dicyclohexylphenylphosphine, ethyldiphenylphosphine, diphenylcyclohexylphosphine, and chlorodiphenylphosphine (4) Quaternary ammonium salts such as tetramethylammonium chloride, tetramethylammonium bromide, tetramethylammonium acetate, tetraethylammonium chloride, tetraethylammonium bromide, tetraethylammonium acetate, tetra-n-butylammonium fluoride, tetra-n-butylammonium chloride, tetra-n-butylammonium bromide, tetra-n-butylammonium iodide, tetra-n-butylammonium acetate, tetra-n-butylammonium borohydride, tetra-n-butylammonium hexafluorophosphite, tetra-n-butylammonium hydrogen sulfite, tetra-n-butylammonium tetrafluoroborate, tetra-n-butylammonium tetraphenylborate, tetra-n-butylammonium para-toluenesulfonate, tetra-n-hexylammonium chloride, tetra-n-hexylammonium bromide, tetra-n-hexylammonium acetate, tetra-n-octylammonium chloride, tetra-n-octylammonium bromide, and tetra-n-octylammonium acetate, trimethyl-n-octylammonium chloride, trimethylbenzylammonium chloride, trimethylbenzylammonium bromide, triethyl-n-octylammonium chloride, triethylbenzylammonium chloride, triethylbenzylammonium bromide, tri-n-butyl-n-octylammonium chloride, tri-n-butylbenzylammonium fluoride, tri-n-butylbenzylammonium chloride, tri-n-butylbenzylammonium bromide, tri-n-butylbenzylammonium iodide, methyltriphenylammonium chloride, methyltriphenylamonium bromide, ethyltriphenylammonium chloride, ethyltriphenylammonium bromide, n-butyltriphenylammonium chloride, n-butyltriphenylammonium bromide, 1-methylpyridinium bromide, 1-ethylpyridinium bromide, 1-n-butylpyridinium bromide, 1-n-hexylpyridinium bromide, 1-n-octylpyridinium bromide, 1-n-dodecylpyridinium bromide, 1-n-phenylpyridinium bromide, 1-methylpicolinium bromide, 1-ethylpicolinium bromide, 1-n-butylpicolinium bromide, 1-n-hexylpicolinium bromide, 1-n-octylpicolinium bromide, 1-n-dodecylpicolinium bromide, and 1-n-phenylpicolinium bromide.

(5) Phosphonium salts such as tetramethylphosphonium chloride, tetramethylphosphonium bromide, tetraethylphosphonium chloride, tetraethylphosphonium bromide, tetra-n-butylphosphonium chloride, tetra-n-butylphosphonium bromide, tetra-n-butylphosphonium iodide, tetra-n-hexylphosphonium bromide, tetra-n-octylphosphonium bromide, methyltriphenylphosphonium bromide, methyltriphenylphosphonium iodide, ethyltriphenylphosphonium bromide, ethyltriphenylphosphonium iodide, n-butyltriphenylphosphonium bromide, n-butyltriphenylphosphonium iodide, n-hexyltriphenylphosphonium bromide, n-octyltriphenylphosphonium bromide, tetraphenylphosphonium bromide, tetrakishydroxymethylphosphonium chloride, tetrakishydroxymethylphosphonium bromide, tetrakishydroxyethylphosphonium chloride, and tetrakishydroxybutylphosphonium chloride.

(6) Sulfonium salts such as trimethylsulfonium bromide, triethylsulfonium bromide, tri-n-butylsulfonium chloride, tri-n-butylsulfonium bromide, tri-n-butylsulfonium iodide, tri-n-butylsulfonium tetrafluoroborate, tri-n-hexylsulfonium bromide, tri-n-octylsulfonium bromide, triphenylsulfonium chloride, triphenylsulfonium bromide, and triphenylsulfonium iodide.

(7) Iodonium salts such as diphenyliodonium chloride, diphenyliodonium bromide, and diphenyliodonium iodide.

(8) Mineral acids such as hydrochloric acid, sulfuric acid, nitric acid, phosphoric acid, and carbonic acid, and semi-esters thereof.

(9) Lewis acids represented by boron trifluoride, etherate of boron trifluoride, and the like.

(10) Organic acids and semi-esters thereof.

(11) Silicic acid and tetrafluoroboric acid.

These compounds may be used singly, or two or more kinds may be used in combination. Among these, preferred examples which produce polymerization products with less coloration include amines, phosphines, quaternary ammonium salts, quaternary phosphonium salts, tertiary sulfonium salts, and secondary iodonium salts.

Polymerization by irradiation of an energy line refers to a method of producing a polymerization product by irradiating an energy line (light such as ultraviolet radiation, near-ultraviolet radiation, visible light, near-infrared radiation, and infrared radiation, electron beam, and the like). There are no particular limitations on the kind of energy line, but the energy line is preferably light, and more preferably ultraviolet radiation.

There are no particular limitations on the generation source of energy line, and examples include various light sources such as a low pressure mercury lamp, a medium pressure mercury lamp, a high pressure mercury lamp, an ultrahigh pressure mercury lamp, a UV lamp, a xenon lamp, a carbon arc lamp, a metal halide lamp, a fluorescent lamp, a tungsten lamp, an argon ion laser, a helium-cadmium laser, a helium-neon laser, a krypton ion laser, various semiconductor lasers, a YAG laser, an excimer laser, a light emitting diode, a CRT light source, a plasma light source, and an electron beam irradiator.

There are no particular limitations on the technique for the polymerization using an energy line, and usually, a procedure in which polymerization utilizing a polymerizable functional group of an object material is initiated by a polymerization initiator species that is generated as a polymerization catalyst is decomposed by energy line stimulation, is followed.

The polymerization catalyst used for the polymerization using energy line irradiation is not particularly limited, and can be roughly divided into the following three categories on the basis of the active species thus generated. These polymerization catalysts may be used singly, or plural kinds may be used in combination.

(1) A polymerization catalyst which generates a radical under the irradiation of an energy line;

(2) a polymerization catalyst which generates a cation under the irradiation of an energy line (when the energy line is light, the catalyst is called a photo-acid generator); and (3) a polymerization catalyst which generates an anion under the irradiation of an energy line (when the energy line is light, the catalyst is called a photo-base generator).

Specific examples of the polymerization catalyst used for the polymerization using an energy line include, for example, benzoins and benzoin alkyl ethers (benzoin, benzyl, benzoin methyl ether, and benzoin isopropyl ether), acetophenones (acetophenone, 2,2-dimethoxy-2-phenylacetophenone, 2,2-diethoxy-2-phenylacetophenone, 1,1-dichloroacetophenone, 1-hydroxycyclohexyl phenyl ketone, 2-methyl-1-(4-(methylthio)phenyl)-2-morpholinopropan-1-one, N,N-dimethylaminoacetophenone, and the like), anthraquinones such as (2-methylanthraquinone, 2-ethylanthraquinone, 2-tert-butylanthraquinone, 1-chloroanthraquinone, 2-amylanthraquinone, 2-aminoanthraquinone, and the like), thioxanthones (2,4-dimethylthioxanthone, 2,4-diethylthioxanthone, 2-chlorothioxanthone, 2,4-diisopropylthioxanthone, and the like), ketals (acetophenone dimethyl ketal, benzyl dimethyl ketal, and the like), benzophenones (benzophenone, methylbenzophenone, 4,4'-dichlorobenzophenone, 4,4'-bisdiethylaminobenzophenone, and the like), xanthones, benzoic acid esters (ethyl 4-dimethylaminobenzoate, 2-(dimethylamino) ethyl benzoate, and the like), amines (triethylamine, triethanolamine, and the like), iodonium salt compounds, sulfonium salt compounds, ammonium salt compounds, phosphonium salt compounds, arsonium salt compounds, stibonium salt compounds, oxonium salt compounds, selenium salt compounds, and stannonium salt compounds.

The proportion of the polymerization catalyst described above is preferably 0.0001 moles or more, more preferably 0.005 or more, and even more preferably 0.001 or more, relative to 1 mole of the episulfide compound. When the polymerization catalyst is used in an amount of 0.0001 moles or more, polymerization proceeds efficiently, and there is a tendency that the presence of residual episulfide compound can be reduced. The proportion of the polymerization catalyst is preferably 1.0 mole or less, more preferably 0.5 moles or less, and even more preferably 0.1 moles or less, relative to 1 mole of the episulfide compound. When the polymerization catalyst is 1.0 mole or less, there is a tendency that coloration can be reduced at the time of polymerization.

In the case where the episulfide compound has two or more episulfide groups, a cured product can be obtained by allowing the episulfide compound to react with a curing agent.

The curing agent is not particularly limited as long as it is a conventionally used agent, but specific examples thereof include compounds of the following (1) to (3). These may be used singly, or plural kinds may be used in combination.

(1) Primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl) ether, 1,2-bis-(3-aminopropoxyl)ethane, 1,3-bis-(3-aminopropoxy)-2,2'-dimethylpropane, aminoethylethanolamine, 1,2-bisaminocyclohexane, 1,3-bisaminocyclohexane, 1,4-bisaminocyclohexane, 1,3-bisaminoethylcyclohexane, 1,4-bisaminoethylcyclohexane, 1,3-bisaminopropylcyclohexane, 1,4-bisaminopropylcyclohexane, hydrogenated 4,4'-diaminodiphenylmethane, 2-aminopiperidine, 4-aminopiperidine, 2-aminomethylpiperidine, 4-aminomethylpiperidine, 2-aminoethylpiperidine, 4-aminoethylpiperidine, N-aminoethylpiperidine, N-aminopropylpiperidine, N-aminoethylmorpholine, N-aminopropylmorpholine, isophoronediamine, methanediamine, 1,4-bisaminopropylpiperazine, o-phenylenediamine, m-phenylenediamine, p-phenylenediamine, 2,4-tolylenediamine, 2,6-tolylenediamine, 2,4-toluenediamine, m-aminobenzylamine, 4-chloro-o-phenylenediamine, tetrachloro-p-xylenediamine, 4-methoxy-6-methyl-m-phenylenediamine, m-xylenediamine, p-xylenediamine, 1,5-naphthalenediamine, 2,6-naphthalenediamine, benzidine, 4,4'-bis(o-toluidine), dianisidine, 4,4'-diaminodiphenylmethane, 2,2-(4,4'-diaminodiphenyl)propane, 4,4'-diaminodiphenyl ether, 4,4'-thiodianiline, 4,4'-diaminodiphenylsulfone, 4,4'-diaminoditolylsulfone, methylenebis(o-chloroaniline), 3,9-bis(3-aminopropyl)-2,4,8,10-tetraoxaspiro[5,5]undecane, diethylenetriamine, iminobispropylamine, methyliminobispropylamine, bis(hexamethylene)triamine, triethylenetetramine, tetraethylenepentamine, pentaethylenehexamine, N-aminoethylpiperazine, N-aminopropylpiperazine, 1,4-bis(aminoethylpiperazine), 1,4-bis(aminopropylpiperazine), 2,6-diaminopyridine, and bis(3,4-diaminophenyl)sulfone;

secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5-dimethylpiperazine, 2,6-dimethylpiperazine, homopiperazine, 1,1-di(4-piperidyl)methane, 1,2-di(4-piperidyl)ethane, 1,3-di(4-piperidyl)propane, 1,4-di(4-piperidyl)butane, and tetramethylguanidine; and tertiary polyamines such as tetramethylethylenediamine, pyrazine, N,N'-dimethylpiperazine, N,N'-bis((2-hydroxy)propyl)piperazine, hexamethylenetetramine, N,N,N',N'-tetramethyl-1,3-butanamine, 2-dimethylamino-2-hydroxypropane, diethylaminoethanol, N,N,N-tris(3-dimethylaminopropyl)amine, 2,4,6-tris(N,N-dimethylaminomethyl)phenol, and heptamethylisobiguanide; amine-based compounds represented by the above compounds.

(2) Phthalic anhydride, succinic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, 1,2,3,6-tetrahydrophthalic anhydride, 3,4,5,6-tetrahydrophthalic anhydride, hexahydrophthalic anhydride, "4-methylhexahydrophthalic anhydride/hexahydrophthalic anhydride=70/30", 4-methylhexahydrophthalic anhydride, "methylbicyclo[2.2.1]heptanes-2,3-dicarboxylic acid anhydride/bicyclo[2.2.1]heptanes-2,3-dicarboxylic acid anhydride", tetrapropenylsuccinic anhydride, octenylsuccinic anhydride, and 2,5-diketotetrahydrofuran; acid anhydride compounds represented by the above compounds.

(3) Thiol compounds such as methanedithiol, 1,2-dimercaptoethane, 2,2-dimercaptopropane, 1,3-dimercaptopropane, 1,2,3-trimercaptopropane, 1,4-dimercaptobutane, 1,6-dimercaptohexane, bis(2-mercaptoethyl) sulfide, 1,2-bis(2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane-1,2-dithiol, 2-mercaptomethyl-1,3-dimercaptopropane, 2-mercaptomethyl-1,4-dimercaptopropane, 2-(2-mercaptoethylthio)-1,3-dimercaptopropane, 1,2-bis(2-mercaptoethylthio)-3-mercaptopropane, 1,1,1-tris(mercaptomethyl)propane, tetrakis(mercaptomethyl)methane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, ethylene glycol bis(2-mercaptoacetate), ethylene glycol bis(3-mercaptopropionate), 1,4-butanediol bis(2-mercaptoacetate), 1,4-butanediol bis(3-mercaptopropionate), trimethylolpropane tris(2-mercaptoacetate), trimethylolpropane tris(3-mercaptopropionate), pentaerythritol tetrakis(2-mercaptoacetate), pentaerythritol tetrakis(3-mercaptopropionate), 1,1-dimercaptocyclohexane, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-bis(mercaptomethyl)-1,4-dithiane, 2,5-bis(mercaptoethyl)-1,4-dithiane, 1,2-bis(mercaptomethyl)benzene, 1,3-bis(mercaptomethyl)benzene, 1,4-bis(mercaptomethyl)benzene, bis(4-mercaptophenyl) sulfide, bis(4-mercaptophenyl) ether, 2,2-bis(4-mercaptophenyl)propane, bis(4-mercaptomethylphenyl) sulfide, bis(4-mercaptomethylphenyl) ether, 2,2-bis(4-mercaptomethylphenyl)propane, o-dimercaptobenzene, m-dimercaptobenzene, p-dimercaptobenzene, and 1,3,5-trimercaptobenzene.

The amount of the curing agent is not particularly limited, but preferably, the amount can be determined by using the mixing index γ, which is the ratio of the amount of substance of the substituent that is capable of reacting with the episulfide group contained in the curing agent with respect to the amount of substance of the episulfide group contained in the episulfide compound, as an index. The mixing index γ is represented by the following formula (10):

$$\text{Mixing index } \gamma=(\gamma k)/(\gamma e) \quad (10)$$

in formula (10), γk represents the amount of substance (mol) of the substituent that is capable of reacting with the episulfide group contained in the curing agent; and γe represents the amount of substance (mol number) of the episulfide group.

The mixing index γ is preferably 0.1 or greater, more preferably 0.2 or greater, and even more preferably 0.3 or greater. When the mixing index γ is 0.1 or greater, the presence of residual episulfide groups can be suppressed, and there is a tendency that a satisfactory cured product is obtained. The mixing index γ is preferably 1.5 or less, more preferably 1.3 or less, and even more preferably 1.2 or less. When the mixing index γ is 1.5 or less, the presence of residual substituents that are contained in the curing agent and are capable of reacting with the episulfide group can be suppressed, and there is a tendency that the mechanical properties of the cured product thus obtained can be enhanced.

In the process of obtaining a cured product from the episulfide compound and a curing agent, it is effective to use a curing accelerator for the purpose of further increasing the curing rate.

The curing accelerator is not particularly limited, but can be selected from tertiary amines and salts thereof, organic phosphorus compounds, quaternary phosphonium salts, organic metal compounds, quaternary ammonium salts, and metal halides. These may be used singly, or plural kinds may be used in combination. Specific examples of the curing accelerator include compounds of the following (1) to (8).

(1) Tertiary amines: benzyldimethylamine, 2,4,6-tris(dimethylaminomethyl)phenol, cyclohexyldimethylamine, triethanolamine, and the like;

(2) imidazoles: 2-methylimidazole, 2-n-heptylimidazole, 2-n-undecylimidazole, 2-phenylimidazole, 2-phenyl-4-methylimidazole, 1-benzyl-2-methylimidazole, 1-benzyl-2-phenylimidazole, 1,2-dimethylimidazole, 2-ethyl-4-methylimidazole, 1-(2-cyanoethyl)-2-methylimidazole, 1-(2-cyanoethyl)-2-n-undecylimidazole, 1-(2-cyanoethyl)-2-phenylimidazole, 1-(2-cyanoethyl)-2-ethyl-4-methylimidazole, 2-phenyl-4-methyl-5-hydroxymethylimidazole, 2-phenyl-4,5-di(hydroxymethyl)imidazole, 1-(2-cyanoethyl)-2-phenyl-4,5-di[(2'-cyanoethoxy)methyl]imidazole, 1-(2-cyanoethyl)-2-n-undecylimidazoium trimellitate, 1-(2-cyanoethyl)-2-phenylimidazolium trimellitate, 1-(2-cyanoethyl)-2-ethyl-4-methylimidazolium trimellitate, 2,4-diamino-6-[2'-methylimidazolyl(1')]ethyl-s-triazine, 2,4-diamino-6-(2'-n-undecylimidazolyl)ethyl-s-triazine, 2,4-diamino-6-[2'-ethyl-4'-methylimidazolyl(1')]ethyl-s-triazine, an isocyanuric acid adduct of 2-methylimidazole, an isocyanuric acid adduct of 2-phenylimidazole, an isocyanuric acid adduct of 2,4-diamino-6-[2'-methylimidazolyl(1')]ethyl-s-triazine, and the like;

(3) organic phosphorus-based compounds: diphenylphosphine, triphenylphosphine, triphenyl phosphite, and the like;

(4) quaternary phosphonium salts: benzyltriphenylphosphonium chloride, tetra-n-butylphosphonium bromide, methyltriphenylphosphonium bromide, ethyltriphenylphosphonium bromide, n-butyltriphenylphosphonium bromide, tetraphenylphosphonium bromide, ethyltriphenylphosphonium iodide, ethyltriphenylphosphonium acetate, tetra-n-butylphosphonium o,o-diethylphosphorodithionate, tetra-n-butylphosphonium benzotriazolate, tetra-n-butylphosphonium tetrafluoroborate, tetra-n-butylphosphonium tetraphenylborate, tetraphenylphosphonium tetraphenylborate, and the like;

(5) diazabicycloalkenes: 1,8-diazabicyclo[5.4.0]undecene-7 and organic acid salts thereof, and the like;

(6) organometallic compounds: zinc octoate, tin octoate, an aluminum-acetylacetone complex, and the like;

(7) quaternary ammonium salts: tetraethylammonium bromide, tetra-n-butylammonium bromide, and the like;

(8) metal halogenated compounds: boron compounds such as boron trifluoride and triphenyl borate; zinc chloride, stannic chloride, and the like.

The amount of the curing accelerator is not particularly limited, and a preferred amount can be determined from the mixing index η, which is a ratio of the amount of the curing accelerator with respect to the mass of the episulfide compound. The mixing index δ is represented by the following formula (11):

$$\text{Mixing index } \delta = (\delta c)/(\delta e) \times 100 \qquad (11)$$

in formula (11),

δc represents the mass (g) of the curing accelerator; and
δe represents the mass (g) of the episulfide compound.

The mixing index δ is preferably 0.01 or greater, more preferably 0.05 or greater, and even more preferably 0.1 or greater. When the mixing index δ is 0.01 or greater, the presence of residual episulfide group can be suppressed, and there is a tendency that a satisfactory cured product is obtained. The mixing index δ is preferably 1 or less, more preferably 0.7 or less, and even more preferably 0.5 or less. When the mixing index δ is 1 or less, coloration of the cured product may be suppressed.

The polymerization product and cured product of the episulfide compound can appropriately contain various organic resins, an inorganic filler, a colorant, a leveling agent, a lubricating agent, a surfactant, a silicone compound, a reactive diluent, a non-reactive diluent, an oxidation inhibitor, a photo stabilizer, and the like in accordance with the purpose. In addition to those, materials that are generally provided as additives for resin (a plasticizer, a flame retardant, a stabilizer, an antistatic agent, an impact resistant reinforcing agent, a foaming agent, an antibacterial/antifungal agent, a conductive filler, an antifog agent, a crosslinking agent, and the like) may be incorporated into the polymerization product or the cured product without any problem.

There are no particular limitations on the organic resin, and examples include an acrylic resin, a polyester resin, and a polyimide resin.

Examples of the inorganic filler include silicas (molten pulverized silica, crystal pulverized silica, spherical silica, fumed silica, colloidal silica, precipitated silica, and the like), silicon carbide, silicon nitride, boron nitride, calcium carbonate, magnesium carbonate, barium sulfate, calcium sulfate, mica, talc, clay, aluminum oxide, magnesium oxide, zirconium oxide, aluminum oxide, magnesium oxide, calcium silicate, aluminum silicate, aluminum lithium silicate, zirconium silicate, barium titanate, glass fiber, carbon fiber, and molybdenum disulfide. Among these, silicas, calcium carbonate, aluminum oxide, aluminum hydroxide and calcium silicate are preferred, and when the properties of the cured product are considered, silicas are more preferred. These inorganic fillers may be used singly, or plural kinds may be used in combination.

The colorant is not particularly limited as long as it is a substance used for the purpose of coloration, and for example, the colorant can be selected from various organic coloring materials of phthalocyanine, azo, disazo, quinacridone, anthraquinone, flavanthrone, perinone, perylene, dioxazine, condensed azo, and azomethine compounds; and inorganic pigments such as titanium oxide, lead sulfate, Chrome Yellow, Zinc Yellow, Chrome Vermilion, Anomia ephippium, Cobalt Violet, Prussian Blue, Ultramarine, carbon black, Chrome Green, chromium oxide, and Cobalt Green. These colorants may be used singly, and plural kinds may be used in combination.

The leveling agent is not particularly limited, and can be selected from, for example, oligomers having molecular weights of 4,000 to 12,000 formed from acrylates such as ethyl acrylate, butyl acrylate and 2-ethylhexyl acrylate; epoxidated soybean fatty acids, epoxidated abietyl alcohol, hydrogenated castor oil, and titanium-based coupling agents. These leveling agents may be used singly, or plural kinds may be used in combination.

The lubricating agent is not particularly limited, and can be selected from hydrocarbon-based lubricants such as paraffin wax, microcrystalline wax and polyethylene wax; higher fatty acid-based lubricants such as lauric acid, myristic acid, palmitic acid, stearic acid, arachidic acid and behenic acid; higher fatty acid amide-based lubricants such as stearylamide, palmityl amide, oleyl amide, methylene bisstearo amide, and ethylene bisstearoamide; higher fatty acid ester-based lubricants such as hardened castor oil, butyl stearate, ethylene glycol monostearate, and pentaerythritol (mono-, di-, tri- or tetra-)stearate; alcohol-based lubricants such as cetyl alcohol, stearyl alcohol, polyethylene glycol, and polyglycerol; metal soaps which are metal salts of magnesium, calcium, cadmium, barium, zinc, lead, and the like of lauric acid, myristic acid, palmitic acid, stearic acid, arachidic acid, behenic acid, ricinolic acid, and naphthenic acid; and natural waxes such as carnauba wax, candelilla wax, beeswax and montan wax. These lubricants may be used singly, or plural kinds may be used in combination.

The term surfactant refers to an amphiphilic substance having, in the molecule, a hydrophobic group that does not have affinity to the solvent and a solvophilic group (usually, a hydrophilic group) having affinity to the solvent. There are no particular limitations on the kind of the surfactant, and examples include silicone-based surfactants and fluorine-based surfactants. The surfactants may be used singly, or plural kinds may be used in combination.

There are no particular limitations on the silicone-based compound, and examples include silicone resins, silicone condensates, silicone partial condensates, silicone oils, silane coupling agents, silicone oils, and polysiloxanes. The silicone compounds may be modified by having organic groups introduced into both ends, a single end, or a side chain. The method for modifying the silicone-based compounds is also not particularly limited, and examples include amino modification, epoxy modification, alicyclic epoxy modification, carbinol modification, methacryl modification, polyether modification, mercapto modification, carboxyl modification, phenol modification, silanol modification, polyether modification, polyether methoxy modification, and diol modification.

There are no particular limitations on the reactive diluent, and can be selected from, for example, alkyl glycidyl ethers, monoglycidyl ethers of alkyl phenol, neopentyl glycol diglycidyl ether, 1,6-hexanediol diglycidyl ether, alkanoic acid glycidyl esters, ethylene glycol diglycidyl ether, and propylene glycol diglycidyl ether.

The non-reactive diluent is not particularly limited, and can be selected from, for example, high boiling point solvents such as benzyl alcohol, butyl diglycol, and propylene glycol monomethyl ether.

The oxidation inhibitor is not particularly limited, but can be selected from, for example, phenolic oxidation inhibitors, phosphorus-based oxidation inhibitors, sulfur-based oxidation inhibitors, and amine-based oxidation inhibitors. These may be used singly, or plural kinds may be used in combination. Specific examples of the oxidation inhibitor include compounds of the following (1) to (4).

(1) Phenolic oxidation inhibitors: for example, the following alkylphenols, hydroquinones, thioalkyls or thioaryls, benzyl compounds, triazines, esters of β-(3,5-di-tert-butyl-4-hydroxyphenyl)propionic acid and monohydric or polyhydric alcohols, esters of β-(5-tert-butyl-4-hydroxy-3-methylphenyl)propionic acid and monohydric or polyhydric alcohols, esters of β-(3,5-dicyclohexyl-4-hydroxyphenyl)propionic acid and monohydric or polyhydric alcohols, esters of 3,5-di-tert-butyl-4-hydroxyphenylacetic acid and monohydric or polyhydric alcohols, amides of β-(3,5-di-tert-butyl-4-hydroxyphenyl)propionic acid, and vitamins.

(1-1) Alkylphenols: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols having linear or branched side chains (for example, 2,6-dinonyl-4-methylphenol), 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol, and mixtures thereof, 4-hydroxylauranilide, 4-hydroxystearanilide, and octyl N-(3,5-di-tert-butyl-4-hydroxyphenyl)carbamate, and the like;

(1-2) hydroquinones: 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate, and the like;

(1-3) thioalkylphenols or thioarylphenols: 2,4-dioctylthiomethyl-6-tert-butylphenol, 2,4-dioctylthiomethyl-6-methylphenol, 2,4-dioctylthiomethyl-6-ethyl phenol, 2,6-didodecylthiomethyl-4-nonylphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide, and the like;

(1-5) bisphenols: 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane, and the like;

(1-4) benzyl compounds: 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulfide, isooctyl 3,5-di-tert-butyl-4-hydroxybenzylmercaptoacetate, dioctadecyl 2,2-bis(3,5-di-tert-butyl-2-hydroxybenzyl)malonate, dioctadecyl 2-(3-tert-butyl-4-hydroxy-5-methylbenzyl)malonate, didodecylmercaptoethyl 2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol, and the like;

(1-5) triazines: 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate, and the like;

(1-6) esters of β-(3,5-di-tert-butyl-4-hydroxyphenyl)propionic acid and monohydric or polyhydric alcohols: esters of β-(3,5-di-tert-butyl-4-hydroxyphenyl)propionic acid and monohydric or polyhydric alcohols selected from methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, and the like;

(1-7) esters of β-(5-tert-butyl-4-hydroxy-3-methylphenyl)propionic acid and monohydric or polyhydric alcohols: esters of β-(5-tert-butyl-4-hydroxy-3-methylphenyl)propionic acid and monohydric or polyhydric alcohols selected from methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, 3,9-bis[2-{3-(3-tert-butyl-4-hydroxy-5-methylphenyl)propionyloxy}-1,1-dimethylethyl]-2,4,8,10-tetraoxaspiro[5.5]undecane, and the like;

(1-8) esters of β-(3,5-dicyclohexyl-4-hydroxyphenyl)propionic acid and monohydric or polyhydric alcohols: esters of β-(3,5-dicyclohexyl-4-hydroxyphenyl)propionic acid and monohydric or polyhydric alcohols selected from methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oximide, 3-thiaundecanol, 3-thiapentadecanol, trimethylhexanediol, trimethylolpropane, and 4-hydroxymethyl-1-phospha-2,6,7-trioxabicyclo[2.2.2]octane;

(1-9) esters of 3,5-di-tert-butyl-4-hydroxyphenylacetic acid and monohydric or polyhydric alcohols: esters of 3,5-di-tert-butyl-4-hydroxyphenylacetic acid and monohydric or polyhydric alcohols selected from methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, and 4-hydroxymethyl-1-phospha-2,6,7-trioxabicyclo[2.2.2]octane.

(1-10) amides of β-(3,5-di-tert-butyl-4-hydroxyphenyl) propionic acid: N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl) hydrazide, and N,N'-bis[2-(3-[3,5-di-tert-butyl-4-hydroxyphenyl]propionyloxy)ethyl]oxamide, and the like; and (1-11) vitamins: α-tocopherol, β-tocopherol, γ-tocopherol, δ-tocopherol, and mixtures thereof, tocotrienol, ascorbic acid, and the like.

(2) Phosphorus-based oxidation inhibitors: the following phosphonates, phosphites, and oxaphosphaphenanthrenes.

(2-1) Phosphonates: dimethyl-2,5-di-tert-butyl-4-hydroxybenzyl phosphonate, diethyl-3,5-di-tert-butyl-4-hydroxybenzyl phosphonate, dioctadecyl-3,5-di-tert-butyl-4-hydroxybenzyl phosphonate, dioctadecyl-5-tert-butyl-4-hydroxy-3-methylbenzyl phosphonate, tetrakis(2,4-di-tert-butylphenyl)-4,4'-biphenylene diphosphonate, calcium salt of monoethyl ester of 3,5-di-tert-butyl-4-hydroxybenzylphosphonic acid, and the like;

(2-2) phosphites: trioctyl phosphite, trilauryl phosphite, tridecyl phosphite, octyl diphenyl phosphite, tris(2,4-di-tert-butylphenyl)phosphite, triphenyl phosphite, tris(butoxyethyl)phosphite, tris(nonylphenyl)phosphite, distearyl pentaerythritol diphosphite, tetra(tridecyl)-1,1,3-tris(2-methyl-5-tert-butyl-4-hydroxy phenyl)butane diphosphite, tetra (C12-C15 mixed alkyl)-4,4'-isopropylidene diphenyl diphosphite, tetra(tridecyl)-4,4'-butylidenebis(3-methyl-6-tert-butylphenol)diphosphite, tris(3,5-di-tert-butyl-4-hydroxyphenyl)phosphite, tris(mono-, di-mixed nonylphenyl) phosphite, hydrogenated-4,4'-isopropylidene diphenol polyphosphite, bis(octylphenyl)-bis[4,4'-butylidenebis(3-methyl-6-tert-butylphenol)]-1,6-hexanediol diphosphite, phenyl-4,4'-isopropylidene diphenol pentaerythritol diphosphite, bis(2,4-di-tert-butylphenyl)pentaerythritol diphosphite, bis(2,6-di-tert-butyl-4-methylphenyl)pentaerythritol diphosphite, tris[4,4'-isopropylidenebis(2-tert-butylphenol)]phosphite, phenyl diisodecyl phosphite, di(nonylphenyl)pentaerythritol diphosphite), tris(1,3-distearoyloxyisopropyl)phosphite, 4,4'-isopropylidenebis(2-tert-butylphenol)-di(nonylphenyl)phosphite, and the like;

(2-3) oxaphosphaphenanthrenes: 9,10-dihydro-9-oxa-10-phosphaphenanthrene-10-oxide, 8-chloro-9,10-dihydro-9-oxa-10-phosphaphenanthrene-10-oxide, 8-t-butyl-9,10-dihydro-9-oxa-10-phosphaphenanthrene-10-oxide, and the like.

(3) Sulfur-based oxidation inhibitors: the following dialkylthiopropionates, esters of octylthiopropionic acid and polyhydric alcohols, esters of laurylthiopropionic acid and polyhydric alcohols, and esters of stearylthiopropionic acid and polyhydric alcohols.

(3-1) Dialkyl thiopropionates: dilauryl thiodipropionate, dimyristyl thiodipropionate, distearyl thiodipropionate, and the like;

(3-2) esters of octylthiopropionic acid and polyhydric alcohols: esters of octylthiopropionic acid and polyhydric alcohols selected from glycerin, trimethylolethane, trimethylolpropane, pentaerythritol, trishydroxyethyl isocyanurate, and the like;

(3-3) esters of laurylthiopropionic acid and polyhydric alcohols: esters of laurylthiopropionic acid and glycerin, trimethylolethane, trimethylolpropane, pentaerythritol, and trishydroxyethyl isocyanurate; and (3-4) esters of stearylthiopropionic acid and polyhydric alcohols: esters of stearylthiopropionic acid and polyhydric alcohols selected from such as glycerin, trimethylolethane, trimethylolpropane, pentaerythritol, trishydroxyethyl isocyanurate, and the like.

(4) amine-based oxidation inhibitors: N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine (for example, p,p'-di-tert-octyl diphenylamine), 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl)phenyl]amine, tert-octylated N-phenyl-1-naphthylamine, a mixture of monoalkylated and dialkylated tert-butyl-/tert-octyldiphenylamines, a mixture of monoalkylated and dialkylated nonyldiphenylamines, a mixture of monoalkylated and dialkylated dodecyldiphenylamines, a mixture of monoalkylated and dialkylated isopropyl/isohexyldiphenylamines, a mixture of monoalkylated and dialkylated tert-butyldiphenylamines, 2,3-dihydro-3,3-dimethyl-4H-1,4-benzothiazine, phenothiazine, a mixture of monoalkylated and dialkylated tert-butyl/tert-octylphenothiazines, a mixture of monoalkylated and dialkylated tert-octylphenothiazines, N-allylphenothiazine, N,N,N',N'-tetraphenyl-1,4-diaminobutane-2-ene, N,N-bis(2,2,6,6-tetramethylpiperid-4-yl) hexamethylenediamine, bis(2,2,6,6-tetra-methylpiperid-4-yl)sebacate, 2,2,6,6-tetramethylpiperidin-4-one, 2,2,6,6-tetramethylpiperidin-4-ol, and the like.

The photostabilizer is not particularly limited, but can be selected from triazole-based, benzophenone-based, ester-based, acrylate-based, nickel-based, triazine-based, oxamide-based ultraviolet absorbers; and hindered amine-based photostabilizers. These may be used singly, or plural kinds may be used in combination. Specific examples of the oxidation inhibitor include compounds of the following (1) to (7).

(1) Triazoles: 2-(2'-hydroxy-5'-(1,1,3,3-tetramethylbutyl) phenyl)benzotriazole, 2-(2'-hydroxy-4'-octyloxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol], a transesterification product of 2-[3'-tert-butyl-5'-(2-methoxycarbonylethyl)-2'-hydroxyphenyl]-2H-benzotriazole and polyethylene glycol 300, a triazole compound represented by the following formula (12):

[Chemical formula 9]

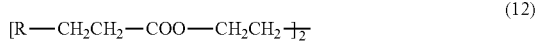

(12)

(wherein R represents 3'-tert-butyl-4'-hydroxy-5'-2H-benzotriazol-2-ylphenyl), 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole, and the like.

(2) Benzophenone compounds: 4-decyloxy, 4-benzyloxy, 4,2',4'-trihydroxy, and 2'-hydroxy-4,4'-dimethoxy derivatives, and the like.

(3) Ester compounds: 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl-3,5-di-tert-butyl-4-hydroxybenzoate, octadecyl-3,5-di-tert-butyl-4-hydroxybenzoate, 2-methyl-4,6-di-tert-butylphenyl 3,5-di-tert-butyl-4-hydroxybenzoate, and the like.

(4) Acrylate compounds: ethyl-α-cyano-β,β-diphenyl acrylate, isooctyl-α-cyano-β,β-diphenyl acrylate, methyl-α-carbomethoxycinnamate, methyl-α-cyano-β-methyl-p-methoxycinnamate, butyl-α-cyano-β-methyl-p-methoxycinnamate, methyl-α-carbomethoxy-p-methoxycinnamate, N-(β-carbomethoxy-β-cyanovinyl)-2-methylindoline, and the like.

(5) Nickel compounds: 1:1 or 1:2 complexes that do or do not have additional ligands such as n-butylamine, triethanolamine and N-cyclohexyldiethanolamine (for example, nickel complex of 2,2'-thiobis[4-(1,1,3,3-tetramethylbutyl) phenol]), nickel dibutyl dithiocarbamate, nickel salt of a monoalkyl ester (for example, methyl or ethyl ester) of 4-hydroxy-3,5-di-tert-butylbenzylphosphoric acid, nickel complexes of ketoximes (for example, a nickel complex of 2-hydroxy-4-methylphenylundecyl ketoxime), nickel complexes of 1-phenyl-4-lauroyl-5-hydroxypyrazole, which do or do not have additional ligands, and the like.

(6) Triazine compounds: 2,4,6-tris(2-hydroxy-4-octyloxyphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy) phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethyl phenyl)-1,3,5-triazine, and the like.

(7) Oxamide compounds: 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide, a mixture thereof with 2-ethoxy-2'-ethyl-5,4'-di-tert-butoxanilide, a mixture of o- and p-methoxy-disubstituted oxanilides, a mixture of o- and p-ethoxy-disubstituted oxanilides, and the like.

(8) Hindered amine compounds: bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzyl malonate, condensate of 1-(2-hydroxyethyl)-2,2,6,6-tetramethyl-4-hydroxypiperidine and succinic acid, linear or cyclic condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensate of N,N'-bis(2,2,6,6-tetramethyl-4-piperidyl)hexamethylenediamine and 4-morpholino-2,6-dichloro-1,3,5-triazine, condensate of 2-chloro-4,6-bis(4-n-butylamino-2,2,6,6-tetramethylpiperidyl)-1,3,5-triazine and 1,2-bis(3-aminopropylamino)ethane, condensate of 2-chloro-4,6-di(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro [4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, 5-(2-ethylhexanoyl)-oxymethyl-3,3,5-trimethyl-2-morpholinone, 1-(2-hydroxy-2-methylpropyl)-4-octadecanoyloxy-2,2,6,6-tetramethylpiperidine, 1,3,5-tris(N-cyclohexyl-N-(2,2,6,6-tetramethylpiperazin-3-on-4-yl)amino)-s-triazine, 1,3,5-tris(N-cyclohexyl-N-(1,2,2,6,6-pentamethylpiperazin-3-on-4-yl)amino)-s-triazine, reaction product between 2,4-bis[(1-cyclohexyloxy-2,2,6,6-piperidin-4-yl)butylamino]-6-chloro-s-triazine and N,N'-bis(3-aminopropyl) ethylenediamine, a mixture of 4-hexadecyloxy- and 4-stearyloxy-2,2,6,6-tetramethylpiperidines, condensate of N,N'-bis(2,2,6,6-tetramethyl-4-piperidyl)hexamethylenediamine and 4-cyclohexylamino-2,6-dichloro-1,3,5-triazine, condensate of 1,2-bis(3-aminopropylamino)ethane and 2,4,6-trichloro-1,3,5-triazine as well as 4-butylamino-2,2,6,6-tetramethylpiperidine, condensate of 1,6-hexanediamine and 2,4,6-trichloro-1,3,5-triazine as well as N,N-dibutylamine and 4-butylamino-2,2,6,6-tetramethylpiperidine, N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4.5]decane; 5-(2-ethylhexanoyl)oxymethyl-3,3,5-trimethyl-2-morpholinone, a reaction product between 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl) ethene, N,N'-bisformyl-N,N'-bis(2,2,6,6-tetramethyl-4-piperidyl)hexamethylene diamine, diester of 4-methoxymethylenemalonic acid and 1,2,2,6,6-pentamethyl-4-hydroxypiperidine, poly[methylpropyl-3-oxy-4-(2,2,6,6-tetramethyl-4-piperidyl)]siloxane, a reaction product between a maleic anhydride-α-olefin copolymer and 2,2,6,6-tetramethyl-4-aminopiperidine or 1,2,2,6,6-pentamethyl-4-aminopiperidine, and the like.

There are no particular limitations on the use of the episulfide compound and a polymerization product or cured product thereof, and the compounds can be used as, for example, electronic materials (insulators; templates and circuit units for alternating current transformer, switching devices and the like; packages for various components; peripheral materials of IC/LED/semiconductors [encapsulant materials, lens materials, substrate materials, die bonding materials, chip coating materials, laminates, optical fibers, light waveguides, optical filters, adhesives for electronic components, coating materials, sealing materials, insulating materials, photoresists, encapsulant materials, potting materials, light transmitting layers or interlayer insulating layers of optical discs, light guiding plates, antireflection films, and the like]; rotator coils for power generating machines, motors, and the like; coil impregnation, printed wiring boards, laminates, insulating boards, medium-sized insulators, coils, connectors, terminals, various casings, electric components, and the like), coating materials (corrosion-proof coating materials, maintenance materials, ship coating, corrosion-resistant lining, primers for automobiles and electrical appliances, beverage/beer cans, lacquer for exterior surfaces, extruded tube coating, general corrosion-proof coating, maintenance coating, lacquer for woodwork products, electrodeposition primers for automobiles, other industrial electrodeposition coating, lacquer for beverage/beer can interior surfaces, coil coating, coating for drum/can interior surfaces, acid-resistant lining, wire enamel, insulating coating materials, primers for automobiles, decorative and corrosion-proof coating for various metal products, coating for pipe interior and exterior surfaces, insulative coating for electric components, and the like), composite materials (pipe/tanks for chemical plants, flight equipment, automobile members, various sport goods, carbon fiber composite materials, aramid fiber composite materials, and the like), materials for civil engineering and construction (floor materials, paving materials, membranes, slip-proof and lamination pavement, concrete construction jointing/padding, anchor embedding and adhesion, precast concrete bonding, tile adhesion, repair of cracks in concrete structures, pedestal grout leveling, corrosion-proof/waterproof coating for water and sewage facilities, corrosion-proof lamination lining for tanks, corrosion-proof coating for iron structures, mastic coating for construction exterior walls, and the like), adhesives (adhesives for materials of the same kind or different kinds, such as metals, glass, ceramics, cement, concrete, wood and plastics; adhesives for assembling of automobiles, railway vehicles, aircrafts and the like; adhesives for composite panel production for prefabs, and the like: including one-liquid type, two-liquid type, and sheet-type adhesives), jigs and tools for aircrafts, automobiles and plastic molding (resin molds such as press mold, stretched die, and matched die; molds for vacuum molding and blow molding, master models, patterns for casting, lamination jigs and tools, jigs and tools for various testings, and the like), modifiers/stabilizers (resin processing of fibers, stabilizers for polyvinyl chloride, additives to synthetic rubbers, and the like), insecticides (against harmful insects such as houseflies, mosquitoes, cockroaches and the like), drugs (therapeutic agents for inflammatory/allergic diseases [for example, systemic inflammatory response syndrome (SIRS), anaphylaxis or anaphylactic responses, allergic vasculitis, hepatitis, nephritis, renal failure, pancreatitis, rhinitis, arthritis, inflammatory ocular diseases (for example, conjunctivitis), inflammatory bower diseases (for example, ulcerative colonitis, Crohn's disease, and eosinophilic gastritis), cerebral circulatory system diseases (for example, arteriosclerosis, thrombosis, ischemia/reperfusion injury, restenosis, and infarction), respiratory system diseases (for example, acute respiratory distress syndrome (ARDS), asthma, and allergic bronchopulmonary aspergillosis), dermatoses (for example, dermatitis (for example, atopic dermatitis, psoriasis, contact dermatitis, eczema, urticaria, and itchness), and the like), autoimmune diseases (for example, multiple sclerosis, chronic arthritic rheumatism, systemic erythematodes, Type I diabetes mellitus, glomerulonephritis, and Sjogren syndrome), and transplanted organ rejection reaction], metabolic/endocrine system diseases [for example, diabetes mellitus], cancerous diseases [for example, malignant neoplasm (for example, leukemia, solid tumors, and cancer metastasis)], infections or diseases related to infection [for example, viral diseases (for example, acquired immune deficiency syndrome and SARS), AIDS, and dementia], and the like), herbicides (acetyl-coenzyme A carboxylase inhibitors, 5-enol-pyruvyl shikimate-3-phosphate synthetase inhibitors, synthetic auxin agent, photosystem II inhibitors, protoporphyrinogen oxidase inhibitors, phytoene desaturase inhibitors, 4-hydroxyphenylpyruvate oxygenase inhibitors, VLCFA (very long chain fatty acid) synthesis inhibitors, and the like), rubber modifiers (vulcanizers, vulcanization accelerators, and the like), fragrances (perfumed soaps, shower gels or bath gels, shampoos, hair conditioners, body deodorants, antiperspirants, air fresheners, liquid or solid detergents for fabric treatment, detergent compositions or cleaner products for tableware or various surfaces, cosmetics, laundry detergents, fabric softeners, food flavors, and the like), and the like.

Examples of the lens materials include lenses for optical instruments, lenses for automobile lamps, spectacle lenses, pickup lenses for CD, DVD and the like, and projector lenses.

There are no particular limitations on the use of LED encapsulant materials, and the use can be extended to a wide variety of fields such as displays, electric signboards, traffic signals, display backlights (organic EL displays, mobile telephones, mobile PC's, and the like), interior and exterior illuminations for automobiles, illuminations, lighting devices, and flashlights.

EXAMPLES

Hereinafter, Examples that specifically explain the present exemplary embodiment will be illustrated. The present invention is not intended to be limited to the following Examples as long as the gist is maintained.

<Hydroxyl Value (HV)>
The hydroxyl value (HV) was calculated by the following formula (13):

$$HV\ (mg/g)=1/MWPO \times OHN \times 1000 \times MWPH \quad (13)$$

wherein MWPO represents the molecular weight of a polyhydric hydroxyl compound;

OHN represents the number of hydroxyl groups contained in the polyhydric hydroxyl compound; and MWPH represents the molecular weight of potassium hydroxide.

However, when the polyhydric hydroxyl compound was a mixture of plural kinds of compounds, and a definite molecular weight could not be determined, the hydroxyl value was measured by "JIS K1557-1:2007 Plastics—Testing method for polyols for the use in the production of polyurethane—Part 1: Method for determining hydroxyl value".

<Epoxy Equivalent (WPE)>
The epoxy equivalent of an epoxy resin was measured according to "JIS K7236:2001 (Method for determining epoxy equivalent of epoxy resin)".

<Calculation of Mixing Index $\alpha$>
The mixing index $\alpha$ was calculated by the following formula (1):

$$\text{Mixing index } \alpha = \alpha t/\alpha e \quad (1)$$

wherein $\alpha t$ represents the amount of substance (mol) of sulfur atoms that are contained in a thiating agent and can be used in the production of episulfide groups; and $\alpha e$ represents the amount of substance (mol) of epoxy groups that are contained in an epoxy compound.

<Calculation of mixing index $\beta$>
The mixing index $\beta$ was calculated by the following formula (2):

$$\text{Mixing index } \beta = \beta t/\beta o \quad (2)$$

wherein $\beta t$ represents the mass (g) of a thiating agent; and $\beta o$ represents the mass (g) of a polyhydric hydroxyl compound.

<Calculation of Mixing Index $\epsilon$>
The mixing index $\epsilon$ is a mixing index which replaces the mixing index $\beta$ in the case where a monohydric hydroxyl compound is used. The mixing index $\epsilon$ was calculated by the following formula (14):

$$\text{Mixing index } \epsilon = \epsilon t/\epsilon o \quad (14)$$

wherein $\epsilon t$ represents the mass (g) of a thiating agent; and $\epsilon o$ represents the mass (g) of a monohydric hydroxyl compound.

<Calculation of Epoxy Group Reaction Rate and Episulfide Group Yield: $^1$H-NMR Analysis>
The $^1$H-NMR analysis was carried out by the following procedure.

(1) 10 mg of a sample and 20 mg of an internal standard substance were weighed in a sample bottle, and chloroform-d (manufactured by Wako Pure Chemical Industries, Ltd.) was added thereto to adjust the total amount to 1 g.

Internal standard substance: 1,1,2,2-tetrabromoethane (manufactured by Tokyo Chemical Industry Co., Ltd.; hereinafter, referred to as "TBE")

(2) The solution of the above item (1) was transferred to an NMR tube having a diameter of 5 mm$\phi$, and $^1$H-NMR was measured under the conditions described below.

Fourier-transform nuclear magnetic resonance apparatus: "Model $\alpha$-400" manufactured by JEOL, Ltd.

Nuclide: $^1$H
Number of average: 200 times

From the measurement results, the epoxy group reaction rate and the episulfide group yield were calculated by the following procedure.

(3) From the $^1$H-NMR chart, the area values of an epoxy group-derived peak and an episulfide group-derived peak were calculated.

The epoxy group-derived peak refers to a peak originating from one hydrogen atom on the hydrocarbon that constitutes an epoxy group. A peak which does not overlap with the peaks originating from the polyhydric hydroxyl compound, episulfide groups thus produced, polymerization products of the episulfide compound, and other components that were added at the time of reaction, is appropriately selected.

The episulfide group-derived peak refers to a peak originating from one hydrogen atom on the hydrocarbon that constitutes an episulfide group. A peak which does not overlap with the peaks originating from epoxy groups, the polyhydric hydroxyl compound, polymerization products of the episulfide compound, and other components that were added at the time of reaction, is appropriately selected.

(4) From the $^1$H-NMR chart, the area value of the peak originating from the internal standard substance was calculated.

(5) The area values calculated in the above items (3) and (4) were inserted into the formulas described below, and the epoxy group reaction rate (%) and the episulfide group yield (%) were determined.

$$\text{Epoxy group reaction rate (\%)}=100-\text{EPOA}\times(\text{TBEG}/\text{TBEM})\times(\text{EPOM}/\text{EPOG})\times(\text{REAG}/\text{SAMG})\times(2/\text{TBEA})\times100$$

$$\text{Episulfide group yield (\%)}=\text{EPIA}\times(\text{TBEG}/\text{TBEM})\times(\text{EPIM}/\text{EPIG})\times(\text{REAG}/\text{SAMG})\times(2/\text{TBEA})\times100$$

EPOA: Area value of the epoxy group-derived peak

EPIA: Area value of the episulfide group-derived peak

TBEA: Area value of the peaks derived from two hydrogen atoms of TBE

EPOG: Mass (g) of the epoxy compound used to prepare the reaction liquid

EPOM: Molecular weight of the epoxy compound used to prepare the reaction liquid EPIG: Mass (g) of the episulfide compound obtainable when the epoxy group reaction rate of the epoxy compound used to prepare the reaction liquid is 100%

EPIM: Molecular weight of the episulfide compound obtainable by the reaction

REAG: Mass (g) of the reaction liquid

TBEG: Mass (g) of TBE used to prepare a solution for performing a $^1$H-NMR analysis (20 mg in the present Example)

TBEM: Molecular weight of TBE

SAMG: Mass (g) of the sample used to prepare a solution for performing a $^1$H-NMR analysis (10 mg in the present Example)

When the hydrogen atoms on the hydrocarbon that constitutes the epoxy groups in the epoxy compound are observed to be represented by the same peak in the $^1$H-NMR chart, or when the hydrogen atoms on the hydrocarbon that constitutes the episulfide group in the resulting episulfide compound are observed to be represented by the same peak in the $^1$H-NMR analytic chart, the calculation can be carried out by modifying the procedure of the item (5) as follows.

(5-2) The area values calculated in the above items (3) and (4) were inserted into the formulas described below, and the epoxy group reaction rate (%) and the episulfide group yield (%) were determined.

Epoxy group reaction rate (%)=100−{EPOA/(number of hydrogen atoms that constitute the epoxy group-derived peak)}×(TBEG/TBEM)×(EPOM/EPOG)×(REAG/SAMG)×(2/TBEA)×100

Episulfide group yield (%)={EPIA/(number of hydrogen atoms that constitute the episulfide group-derived peak)}×(TBEG/TBEM)×(EPIM/EPIG)×(REAG/SAMG)×(2/TBEA)×100

The episulfide group yield was considered satisfactory when the value was 80% or greater, and was considered particularly satisfactory when the value was 90% or greater, while the result was considered inferior in cases other than these.

<Calculation of Epoxy Compound Content and Episulfide Compound Content: $^1$H-NMR Analysis>

The $^1$H-NMR analysis was carried out by the following procedure.

(1) 10 mg of a sample and 20 mg of an internal standard substance were weighed in a sample bottle, and chloroform-d (manufactured by Wako Pure Chemical Industries, Ltd.) was added thereto to adjust the total amount to 1 g.

Internal standard substance: TBE (2) The solution of the above item (1) was transferred to an NMR tube having a diameter of 5 mmφ, and $^1$H-NMR was measured under the conditions described below.

Fourier-transform nuclear magnetic resonance apparatus: "Model α-400" manufactured by JEOL, Ltd.

Nuclide: $^1$H

Number of average: 200 times

From the analysis results, the epoxy compound content and the episulfide compound content were calculated by the following procedure.

(3) From the $^1$H-NMR chart, the area values of an epoxy group-derived peak and an episulfide group-derived peak were calculated.

The epoxy group-derived peak refers to a peak originating from one hydrogen atom on the hydrocarbon that constitutes an epoxy group. A peak which does not overlap with the peaks originating from the polyhydric hydroxyl compound, episulfide groups thus produced, polymerization products of the episulfide compound, and other components that were added at the time of reaction, is appropriately selected.

The episulfide group-derived peak refers to a peak originating from one hydrogen atom on the hydrocarbon that constitutes an episulfide group. A peak which does not overlap with the peaks originating from epoxy groups, the polyhydric hydroxyl compound, polymerization products of the episulfide compound, and other components that were added at the time of reaction, is appropriately selected.

(4) From the $^1$H-NMR chart, the area value of the peak originating from the internal standard substance was calculated.

(5) The area values calculated in the above items (3) and (4) were inserted into the formulas described below, and the episulfide compound content (%) was determined.

Epoxy compound content (%)=EPOA×(TBEG/TBEM)×(EPOM/SAMG)×(2/TBEA)×100

EPOA: Area value of the epoxy group-derived peak

TBEA: Area value of the peaks derived from two hydrogen atoms of TBE

EPOM: Molecular weight of the epoxy compound used to prepare the reaction liquid TBEG: Mass (g) of TBE used to prepare a solution for performing a $^1$H-NMR analysis (20 mg in the present Example) TBEM: Molecular weight of TBE SAMG: Mass (g) of the sample used to prepare a solution for performing a $^1$H-NMR analysis (10 mg in the present Example)

When the hydrogen atoms on the hydrocarbon that constitutes the epoxy groups in the epoxy compound are observed to be represented by the same peak in the $^1$H-NMR chart, the calculation can be carried out by modifying the procedure of the item (5) as follows.

(5-2) The area values calculated in the above items (3) and (4) were inserted into the formulas described below, and the epoxy compound content (%) was determined.

Epoxy compound content (%)={EPOA/(number of hydrogen atoms that constitute the epoxy group-derived peak)}×(TBEG/TBEM)×(EPOM/SAMG)×(2/TBEA)×100

Episulfide group content (%)=EPIA×(TBEG/TBEM)×(EPIM/SAMG)×(2/TBEA)×100

EPIA: Area value of the episulfide group-derived peak

TBEA: Area value of the peaks derived from two hydrogen atoms of TBE

EPIM: Molecular weight of the episulfide compound obtainable by the reaction

TBEG: Mass (g) of TBE used to prepare a solution for performing a $^1$H-NMR analysis (20 mg in the present Example)

TBEM: Molecular weight of TBE

SAMG: Mass (g) of the sample used to prepare a solution for performing a $^1$H-NMR analysis (10 mg in the present Example)

When the hydrogen atoms on the hydrocarbon that constitutes the episulfide groups in the episulfide compound are observed to be represented by the same peak in the $^1$H-NMR chart, the calculation can be carried out by modifying the procedure of the item (5) as follows.

(5-3) The area values calculated in the above items (3) and (4) were inserted into the formulas described below, and the episulfide compound content (%) was determined.

Episulfide compound content (%)={EPIA/(number of hydrogen atoms that constitute the episulfide group-derived peak)}×(TBEG/TBEM)×(EPIM/SAMG)×(2/TBEA)×100

<Reaction Time>

The reaction time means the time period measured from the time point where mixing of all the compounds used in the preparation has been completed, as the initiation point, and taken from the initiation point to the point where a desired epoxy group reaction rate has reached.

The reaction time was considered satisfactory when the time was 24 hours or less, and was considered particularly satisfactory when the time was 6 hours or less, while the result was considered inferior in cases other than these.

<Overall Decision>

In regard to the episulfide group yield and the reaction time, when it was considered that both of them were considered particularly satisfactory, when any one of them was considered particularly satisfactory while the other was considered satisfactory, and when both of them were considered satisfactory, an overall decision was made that the results were acceptable. In cases other than these, an overall decision was made that the results were unacceptable.

<Storage Stability>

A portion of the reaction product was placed and maintained for one year in a constant temperature chamber set at 23° C., and then the episulfide compound content was measured. From the measurement results, the degeneration ratio was calculated using the following formula:

Degeneration ratio (%)={1−(Episulfide compound content after maintenance for one year)/(episulfide compound content before maintenance)}×100

The storage stability was considered satisfactory when the degeneration ratio was 20% or less, and was considered particularly satisfactory when the degeneration ratio was 10% or less, while the result was considered inferior.

<Measurement of Purity of Regenerated Thiating Agent>

The purity of a regenerated thiating agent was measured according to the method described below.

"JIS K8635:2008 (thiourea (reagent))"
"JIS K9000:2008 (ammonium thiocyanate (reagent))"
"JIS K9001:2008 (potassium thiocyanate (reagent))"
"JIS K9002:2008 (sodium thiocyanate (reagent))"

The raw materials used in Examples and Comparative Examples will be described in the following (1) to (73).

(Polyhydric Hydroxyl Compound)

(1) Polyhydric hydroxyl compound A: ethylene glycol (manufactured by Wako Pure Chemical Industries, Ltd.; hereinafter, referred to as "EG")
Hydroxyl value (HV): 1808 mg/g (2) Polyhydric hydroxyl compound B: 1,2-propylene glycol (manufactured by Wako Pure Chemical Industries, Ltd.; hereinafter, referred to "12PG")
Hydroxyl value (HV): 1475 mg/g (3) Polyhydric hydroxyl compound C: 1,3-propylene glycol (manufactured by Wako Pure Chemical Industries, Ltd.; hereinafter, referred to as "13PG")
Hydroxyl value (HV): 1475 mg/g (4) Polyhydric hydroxyl compound D: 1,2-butanediol (manufactured by Wako Pure Chemical Industries, Ltd.; hereinafter, referred to as "12BD")
Hydroxyl value (HV): 1245 mg/g (5) Polyhydric hydroxyl compound E: 1,3-butanediol (manufactured by Wako Pure Chemical Industries, Ltd.; hereinafter, referred to as "13BD")
Hydroxyl value (HV): 1245 mg/g (6) Polyhydric hydroxyl compound F: 1,4-butanediol (manufactured by Wako Pure Chemical Industries, Ltd.; hereinafter, referred to as "14BD")
Hydroxyl value (HV): 1245 mg/g (7) Polyhydric hydroxyl compound G: 1,2-pentanediol (manufactured by Wako Pure Chemical Industries, Ltd.; hereinafter, referred to as "15PD")
Hydroxyl value (HV): 1078 mg/g (8) Polyhydric hydroxyl compound H: 1,2-hexanediol (manufactured by Wako Pure Chemical Industries, Ltd.; hereinafter, referred to as "12HD")
Hydroxyl value (HV): 950 mg/g (9) Polyhydric hydroxyl compound I: 1,2-octanediol (manufactured by Sigma-Aldrich Co.; hereinafter, referred to as "12OD")
Hydroxyl value (HV): 767 mg/g

(10) Polyhydric hydroxyl compound J: glycerol (manufactured by Wako Pure Chemical Industries, Ltd.; hereinafter, referred to as "GL")
Hydroxyl value (HV): 1828 mg/g

(11) Polyhydric hydroxyl compound K: meso-erythritol (manufactured by Wako Pure Chemical Industries, Ltd.; hereinafter, referred to as "ETT")
Hydroxyl value (HV): 1838 mg/g

(12) Polyhydric hydroxyl compound L: xylytol (manufactured by Wako Pure Chemical Industries, Ltd.; hereinafter, referred to as "XT")
Hydroxyl value (HV): 1844 mg/g

(13) Polyhydric hydroxyl compound M: D-mannitol (manufactured by Wako Pure Chemical Industries, Ltd.; hereinafter, referred to as "DMT")
Hydroxyl value (HV): 1848 mg/g

(14) Polyhydric hydroxyl compound M: volemitol (manufactured by Sigma-Aldrich Co.; hereinafter, referred to as "VLT")
Hydroxyl value (HV): 1851 mg/g

(15) Polyhydric hydroxyl compound N: (D)-glucose (Wako Pure Chemical Industries, Ltd.; hereinafter, referred to as "DLC")
Hydroxyl value (HV): 1557 mg/g

(16) Polyhydric hydroxyl compound 0: sucrose (manufactured by Wako Pure Chemical Industries, Ltd.; hereinafter, referred to as "SCR")
Hydroxyl value (HV): 1311 mg/g

(17) Polyhydric hydroxyl compound P: diethylene glycol (manufactured by Wako Pure Chemical Industries, Ltd.; hereinafter, referred to as "DEG")
Hydroxyl value (HV): 1057 mg/g

(18) Polyhydric hydroxyl compound Q: triethylene glycol (manufactured by Wako Pure Chemical Industries, Ltd.; hereinafter, referred to as "TEG")
Hydroxyl value (HV): 747 mg/g

(19) Polyhydric hydroxyl compound R: tetraethylene glycol (manufactured by Wako Pure Chemical Industries, Ltd.; hereinafter, referred to as "TEEG")
Hydroxyl value (HV): 578 mg/g

(20) Polyhydric hydroxyl compound S: pentaethylene glycol (manufactured by Wako Pure Chemical Industries, Ltd.; hereinafter, referred to as "PEEG")
Hydroxyl value (HV): 471 mg/g

(21) Polyhydric hydroxyl compound T: hexaethylene glycol (manufactured by Wako Pure Chemical Industries, Ltd.; hereinafter, referred to as "HEED")
Hydroxyl value (HV): 397 mg/g

(22) Polyhydric hydroxyl compound U: octaethylene glycol (manufactured by Sigma-Aldrich Co.; hereinafter, referred to as "OCEG")
Hydroxyl value (HV): 303 mg/g

(23) Polyhydric hydroxyl compound V: dodecaethylene glycol (manufactured by Sigma-Aldrich Co.; hereinafter, referred to as "DDEG")
Hydroxyl value (HV): 205 mg/g

(24) Polyhydric hydroxyl compound W: polyethylene glycol 200 (manufactured by Wako Pure Chemical Industries, Ltd.; hereinafter, referred to as "PEG200")
Hydroxyl value (HV): 561 mg/g

(25) Polyhydric hydroxyl compound X: polyethylene glycol 300 (manufactured by Wako Pure Chemical Industries, Ltd.; hereinafter, referred to as "PEG300")
Hydroxyl value (HV): 374 mg/g

(26) Polyhydric hydroxyl compound Y: polyethylene glycol 400 (manufactured by Wako Pure Chemical Industries, Ltd.; hereinafter, referred to as "PEG400")
Hydroxyl value (HV): 281 mg/g

(27) Polyhydric hydroxyl compound Z: aqueous solution of methanediol (hereinafter, referred to as "MEOS")

A 10% aqueous solution of formaldehyde (manufactured by Wako Pure Chemical Industries, Ltd.) was diluted with water to prepare a 5% aqueous solution of formaldehyde containing methanediol. The concentration of methanediol was 4%.

Hydroxyl value (HV): 2336 mg/g (in terms of methanediol)

(Epoxy Compound)

(28) Epoxy compound A: phenyl glycidyl ether (manufactured by Wako Pure Chemical Industries, Ltd.; hereinafter, referred to as "PGE")
Epoxy equivalent (WPE): 150 g/eq.

(29) Epoxy compound B: ethylene oxide (manufactured by Sigma-Aldrich Co.; hereinafter, referred to as "EO")
Epoxy equivalent (WPE): 44 g/eq.

(30) Epoxy compound C: propylene oxide (manufactured by Wako Pure Chemical Industries, Ltd.: hereinafter, referred to as "PO")
Epoxy equivalent (WPE): 58 g/eq.

(31) Epoxy compound D: 1,2-epoxybutane (manufactured by Tokyo Chemical Industry Co., Ltd.; hereinafter, referred to as "12EB")
Epoxy equivalent (WPE): 72 g/eq.

(32) Epoxy compound E: 1,2-epoxypentane (manufactured by Tokyo Chemical Industry Co., Ltd.; hereinafter, referred to as "12EP")
Epoxy equivalent (WPE): 86 g/eq.

(33) Epoxy compound F: 1,2-epoxyhexane (manufactured by Tokyo Chemical Industry Co., Ltd.; hereinafter, referred to as "12EH")
Epoxy equivalent (WPE): 100 g/eq.

(34) Epoxy compound G: 1,2-epoxyheptane (manufactured by Tokyo Chemical Industry Co., Ltd.; hereinafter, referred to as "12EHP")
Epoxy equivalent (WPE): 114 g/eq.

(35) Epoxy compound H: 1,2-epoxyoctane (manufactured by Wako Pure Chemical Industries, Ltd.; hereinafter, referred to as "12EO")
Epoxy equivalent (WPE): 128 g/eq.

(36) Epoxy compound I: 1,2-epoxydecane (manufactured by Wako Pure Chemical Industries, Ltd.; hereinafter, referred to as "12ED")
Epoxy equivalent (WPE): 156 g/eq.

(37) Epoxy compound J: 1,2-epoxydodecane (manufactured by Wako Pure Chemical Industries, Ltd.; hereinafter, referred to as "12EDD")
Epoxy equivalent (WPE): 184 g/eq.

(38) Epoxy compound K: 1,2-epoxytetradecane (manufactured by Wako Pure Chemical Industries, Ltd.; hereinafter, referred to as "12ETD")
Epoxy equivalent (WPE): 212 g/eq.

(39) Epoxy compound L: 1,2-epoxyhexadecane (manufactured by Tokyo Chemical Industry Co., Ltd.; hereinafter, referred to as "12EHD")
Epoxy equivalent (WPE): 240 g/eq.

(40) Epoxy compound M: 1,2-epoxyoctadecane (manufactured by Tokyo Chemical Industry Co., Ltd.; hereinafter, referred to as "12EOD")
Epoxy equivalent (WPE): 268 g/eq.

(41) Epoxy compound N: 1,2-epoxyeicosane (manufactured by Tokyo Chemical Industry Co., Ltd.; hereinafter, referred to as "12EEC")
Epoxy equivalent (WPE): 297 g/eq.

(42) Epoxy compound 0: bisphenol A type epoxy compound (hereinafter, referred to as "Bis-A-1")
Trade name: manufactured by Asahi Kasei Epoxy Co., Ltd., "AER"
Epoxy equivalent (WPE): 189 g/eq.

(43) Epoxy compound P: hydrogenated bisphenol A type epoxy compound (hereinafter, referred to as "hydrogenated Bis-A")
Trade name: manufactured by Japan Epoxy Resin Co., Ltd., "YX8000"
Epoxy equivalent (WPE): 205 g/eq.

(44) Epoxy compound Q: bisphenol A type epoxy compound (hereinafter, referred to as "Bis-A-2")
Trade name: manufactured by Asahi Kasei Epoxy Co., Ltd., "AER"
Epoxy equivalent (WPE): 480 g/eq.

(45) Epoxy compound R: bisphenol A type epoxy compound (hereinafter, referred to as "Bis-A-3")
Trade name: manufactured by Asahi Kasei Epoxy Co., Ltd., "AER"
Epoxy equivalent (WPE): 560 g/eq.

(46) Epoxy compound S: bisphenol A type epoxy compound (hereinafter, referred to as "Bis-A-4")
Trade name: manufactured by Asahi Kasei Epoxy Co., Ltd., "AER"
Epoxy equivalent (WPE): 650 g/eq.

(47) Epoxy compound T: cyclopentene oxide (manufactured by Sigma-Aldrich Co.; hereinafter, referred to as "C50")
Epoxy equivalent (WPE): 84 g/eq.

(48) Epoxy compound U: cyclohexene oxide (manufactured by Sigma-Aldrich Co.; hereinafter, referred to as "C60")
Epoxy equivalent (WPE): 98 g/eq.

(49) Epoxy compound V: cycloheptene oxide (manufactured by Sigma-Aldrich Co.; hereinafter, referred to as "C70")
Epoxy equivalent (WPE): 112 g/eq.

(50) Epoxy compound W: cyclooctene oxide (manufactured by Sigma-Aldrich Co.; hereinafter, referred to as "C80")
Epoxy equivalent (WPE): 126 g/eq.

(51) Epoxy compound X: alicyclic epoxy compound (hereinafter, referred to as "CEL")
Trade name: Daicel Corp., "CELLOXIDE 2021P"
Epoxy equivalent (WPE): 131 g/eq.

(52) Epoxy compound Y: bis(2,3-epoxypropyl)disulfide (hereinafter, referred to as "BEDS")
BEDS was synthesized according to the method described in JP 2002-194083 A.
Epoxy equivalent (WPE): 91 g/eq.

(53) Epoxy compound Z: 1,3-bis(3-glycidoxypropyl)-1,1,3,3-tetramethyldisiloxane (hereinafter, referred to as "BGTD")
Trade name: Shin-Etsu Chemical Co., Ltd., "LS-7970"
Epoxy equivalent (WPE): 182 g/eq.

(54) Epoxy compound AA: bis[2-(3,4-epoxycyclohexyl)ethyl]tetramethyldisiloxane (hereinafter, referred to as "BCTD")
Trade name: Gelest, Inc., "SIB 1092.0"
Epoxy equivalent (WPE): 192 g/eq.

(55) Epoxy compound AB: 1,3,5,7-tetra(3-glycidoxypropyl)tetramethylcyclotetrasiloxane (hereinafter, referred to as "TGCS")
TGCS was synthesized according to the method described in Euro. Polym. J. 2010, 46, 1545.
Epoxy equivalent (WPE): 174 g/eq.

(56) Epoxy compound AC: 1,3,5,7-tetra-[2-(3,4-epoxycyclohexylethyl)]tetramethylcyclotetrasiloxane (hereinafter, referred to as "TCCS")
TCCS was synthesized according to the method described in JP 2000-103859 A.
Epoxy equivalent (WPE): 184 g/eq.

(57) Epoxy compound AD: butadiene monoxide (manufactured by Wako Pure Chemical Industries, Ltd.; hereinafter, referred to as "BDMO")
Epoxy equivalent (WPE): 70 g/eq.

(58) Epoxy compound AE: 1,2-epoxy-5-hexene (manufactured by Wako Pure Chemical Industries, Ltd.; hereinafter, referred to as "EPHE")

Epoxy equivalent (WPE): 98 g/eq.

(59) Epoxy compound AF: allyl glycidyl ether (manufactured by Wako Pure Chemical Industries, Ltd.; hereinafter, referred to as "AGE")

Epoxy equivalent (WPE): 114 g/eq.

(60) Epoxy compound AG: 1,2-epoxy-4-vinylcyclohexane (manufactured by Sigma-Aldrich Co.; hereinafter, referred to as "EVCH")

Epoxy equivalent (WPE): 124 g/eq.

(61) Epoxy compound AH: glycidyl methacrylate (manufactured by Wako Pure Chemical Industries, Ltd.; hereinafter, referred to as "GLMT")

Epoxy equivalent: 142 g/eq.

(Thiating Agent)

(62) Thiating agent A: thiourea (manufactured by Wako Pure Chemical Industries, Ltd.; hereinafter, referred to as "TU")

(63) Thiating agent B: potassium thiocyanate (manufactured by Wako Pure Chemical Industries, Ltd.; hereinafter, referred to as "TCK")

(64) Thiating agent C: sodium thiocyanate (manufactured by Sigma-Aldrich Co.; hereinafter, referred to as "TCN")

(65) Thiating agent D: ammonium thiocyanate (manufactured by Wako Pure Chemical Industries, Ltd.; hereinafter, referred to as "TCA")

(Others)

(66) Monohydric hydroxyl compound A: methanol (manufactured by Wako Pure Chemical Industries, Ltd.; hereinafter, referred to as "MN")

(67) Monohydric hydroxyl compound B: ultrapure water (manufactured by Wako Pure Chemical Industries, Ltd.; hereinafter, referred to as "SW")

(68) Additive compound A: toluene (manufactured by Wako Pure Chemical Industries, Ltd.; hereinafter, referred to as "TOL")

(69) Additive compound B: acetonitrile (manufactured by Wako Pure Chemical Industries, Ltd.; hereinafter, referred to as "AN")

(70) Additive compound C: tetrahydrofuran (manufactured by Wako Pure Chemical Industries, Ltd.; hereinafter, referred to as "THF")

(71) Non-polar solvent A: n-hexane (manufactured by Wako Pure Chemical Industries, Ltd.; hereinafter, referred to as "NHX")

(72) Non-polar solvent B: diethyl ether (manufactured by Wako Pure Chemical Industries, Ltd.; hereinafter, referred to as "DEE")

(73) Non-polar solvent C: ethyl acetate (manufactured by Wako Pure Chemical Industries, Ltd.; hereinafter, referred to as "ACET")

Example 1

An episulfide compound was produced by the following procedure.

(1) Preparation: On a magnetic stirrer, a water bath equipped with an electric immersion type cooling-heating unit was mounted, and water and a stirrer bar were inserted therein. The electric immersion type cooling-heating unit was operated so that the water temperature was set to be 20° C.

(2) EG (polyhydric hydroxyl compound) and TU (thiating agent) were introduced into a flask containing a stirring bar according to the composition ratio of Table 1 in an atmosphere at 25° C. and were mixed and stirred. Thus, a uniform solution having the thiating agent dissolved therein was obtained.

(3) PGE (epoxy compound) was added to the solution of (2), and the mixture was mixed and stirred.

(4) The mixing indices $\alpha 1$ and $\beta 1$ in this Example are presented in Table 1.

(5) The epoxy group reaction rate and the episulfide group yield were measured according to the method described above.

(6) The time point at which the epoxy compound of (3) was added was defined as the initiation point, and the time point at which a desired epoxy group reaction rate was reached was defined as the end point. The time taken between the time points was defined as the reaction time.

An episulfide compound was produced by the method described above, and as a result, since the reaction time taken until the epoxy group reaction rate reached 100% was 4 hours as indicated in Table 4, the reaction time was considered particularly satisfactory. Furthermore, since the episulfide group yield was 86%, the episulfide group yield was considered satisfactory. From these results, an overall decision was made that the process was acceptable.

Example 2

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 93%, the episulfide group yield was considered particularly satisfactory. From these results, an overall decision was made that the process was acceptable.

Example 3

An episulfide compound was produced by the same method as that used in Example 1, according to the composition ratio of Table 1. As indicated in Table 4, since the reaction time taken until the epoxy group reaction rate reached 100% was 4 hours, the reaction time was considered particularly satisfactory. Furthermore, since the episulfide group yield was 91%, the episulfide group yield was considered particularly satisfactory. From these results, an overall decision was made that the process was acceptable.

Example 4

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 95%, the episulfide group yield was considered particularly satisfactory. From these results, an overall decision was made that the process was acceptable.

Example 5

An episulfide compound was produced by the same method as that used in Example 1, according to the composition ratio of Table 1. As indicated in Table 4, since the reaction time taken until the epoxy group reaction rate reached 100% was 4 hours, the reaction time was considered particularly satisfactory. Furthermore, since the episulfide group yield was 92%, the episulfide group yield was considered particularly satisfactory. From these results, an overall decision was made that the process was acceptable.

Example 6

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 95%, the episulfide group yield was considered particularly satisfactory. From these results, an overall decision was made that the process was acceptable.

Example 7

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 92%, the episulfide group yield was considered particularly satisfactory. From these results, an overall decision was made that the process was acceptable.

Example 8

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 93%, the episulfide group yield was considered particularly satisfactory. From these results, an overall decision was made that the process was acceptable.

Example 9

An episulfide compound was produced by the same method as that used in Example 1, according to the composition ratio of Table 1. As indicated in Table 4, since the reaction time taken until the epoxy group reaction rate reached 100% was 3 hours, the reaction time was considered particularly satisfactory. Furthermore, since the episulfide group yield was 92%, the episulfide group yield was considered particularly satisfactory. From these results, an overall decision was made that the process was acceptable.

Example 10

An episulfide compound was produced by the same method as that used in Example 1, according to the composition ratio of Table 1. As indicated in Table 4, since the reaction time taken until the epoxy group reaction rate reached 100% was 20 hours, the reaction time was considered satisfactory. Furthermore, since the episulfide group yield was 80%, the episulfide group yield was considered satisfactory. From these results, an overall decision was made that the process was acceptable.

Example 11

An episulfide compound was produced by the same method as that used in Example 1, according to the composition ratio of Table 1. As indicated in Table 4, since the reaction time taken until the epoxy group reaction rate reached 100% was 7 hours, the reaction time was considered satisfactory. Furthermore, since the episulfide group yield was 89%, the episulfide group yield was considered satisfactory. From these results, an overall decision was made that the process was acceptable.

Example 12

An episulfide compound was produced by the same method as that used in Example 1, according to the composition ratio of Table 1. As indicated in Table 4, since the reaction time taken until the epoxy group reaction rate reached 100% was 12 hours, the reaction time was considered satisfactory. Furthermore, since the episulfide group yield was 85%, the episulfide group yield was considered satisfactory. From these results, an overall decision was made that the process was acceptable.

Example 13

An episulfide compound was produced by the same method as that used in Example 1, according to the composition ratio of Table 1. As indicated in Table 4, since the reaction time taken until the epoxy group reaction rate reached 100% was 12 hours, the reaction time was considered satisfactory. Furthermore, since the episulfide group yield was 83%, the episulfide group yield was considered satisfactory. From these results, an overall decision was made that the process was acceptable.

Example 14

An episulfide compound was produced by the same method as that used in Example 1, according to the composition ratio of Table 1. As indicated in Table 4, since the reaction time taken until the epoxy group reaction rate reached 100% was 15 hours, the reaction time was considered satisfactory. Furthermore, since the episulfide group yield was 83%, the episulfide group yield was considered satisfactory. From these results, an overall decision was made that the process was acceptable.

Example 15

An episulfide compound was produced by the same method as that used in Example 1, according to the composition ratio of Table 1. As indicated in Table 4, since the reaction time taken until the epoxy group reaction rate reached 100% was 19 hours, the reaction time was considered satisfactory. Furthermore, since the episulfide group yield was 82%, the episulfide group yield was considered satisfactory. From these results, an overall decision was made that the process was acceptable.

Example 16

An episulfide compound was produced by the same method as that used in Example 1 according to the composition ratio of Table 1, except that the mixing index ϵ was used in addition to the mixing index β. As indicated in Table 4, since the reaction time taken until the epoxy group reaction rate reached 100% was 20 hours, the reaction time was considered satisfactory. Furthermore, since the episulfide group yield was 82%, the episulfide group yield was considered satisfactory. From these results, an overall decision was made that the process was acceptable.

Example 17

An episulfide compound was produced by the same method as that used in Example 1 according to the composition ratio of Table 1, except that the mixing index ε was used in addition to the mixing index β. As indicated in Table 4, since the reaction time taken until the epoxy group reaction rate reached 100% was 23 hours, the reaction time was considered satisfactory. Furthermore, since the episulfide group yield was 80%, the episulfide group yield was considered satisfactory. From these results, an overall decision was made that the process was acceptable.

Example 18

An episulfide compound was produced by the same method as that used in Example 1, according to the composition ratio of Table 1. As indicated in Table 4, since the reaction time taken until the epoxy group reaction rate reached 100% was 8 hours, the reaction time was considered satisfactory. Furthermore, since the episulfide group yield was 86%, the episulfide group yield was considered satisfactory. From these results, an overall decision was made that the process was acceptable.

Example 19

An episulfide compound was produced by the same method as that used in Example 1, according to the composition ratio of Table 1. As indicated in Table 4, since the reaction time taken until the epoxy group reaction rate reached 100% was 13 hours, the reaction time was considered satisfactory. Furthermore, since the episulfide group yield was 83%, the episulfide group yield was considered satisfactory. From these results, an overall decision was made that the process was acceptable.

Example 20

An episulfide compound was produced by the same method as that used in Example 1, according to the composition ratio of Table 1. As indicated in Table 4, since the reaction time taken until the epoxy group reaction rate reached 100% was 15 hours, the reaction time was considered satisfactory. Furthermore, since the episulfide group yield was 81%, the episulfide group yield was considered satisfactory. From these results, an overall decision was made that the process was acceptable.

Example 21

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 92%, the episulfide group yield was considered particularly satisfactory. From these results, an overall decision was made that the process was acceptable.

Example 22

An episulfide compound was produced by the same method as that used in Example 1, according to the composition ratio of Table 1. As indicated in Table 4, since the reaction time taken until the epoxy group reaction rate reached 100% was 1 hour, the reaction time was considered particularly satisfactory. Furthermore, since the episulfide group yield was 86%, the episulfide group yield was considered satisfactory. From these results, an overall decision was made that the process was acceptable.

Example 23

An episulfide compound was produced by the same method as that used in Example 1, according to the composition ratio of Table 1. As indicated in Table 4, since the reaction time taken until the epoxy group reaction rate reached 100% was 1 hour, the reaction time was considered particularly satisfactory. Furthermore, since the episulfide group yield was 80%, the episulfide group yield was considered satisfactory. From these results, an overall decision was made that the process was acceptable.

Example 24

An episulfide compound was produced by the same method as that used in Example 1, according to the composition ratio of Table 1. As indicated in Table 4, since the reaction time taken until the epoxy group reaction rate reached 100% was 3 hours, the reaction time was considered particularly satisfactory. Furthermore, since the episulfide group yield was 95%, the episulfide group yield was considered particularly satisfactory. From these results, an overall decision was made that the process was acceptable.

Example 25

An episulfide compound was produced by the same method as that used in Example 1, according to the composition ratio of Table 1. As indicated in Table 4, since the reaction time taken until the epoxy group reaction rate reached 100% was 8 hours, the reaction time was considered satisfactory. Furthermore, since the episulfide group yield was 89%, the episulfide group yield was considered satisfactory. From these results, an overall decision was made that the process was acceptable.

Example 26

An episulfide compound was produced by the same method as that used in Example 1, according to the composition ratio of Table 1. As indicated in Table 4, since the reaction time taken until the epoxy group reaction rate reached 100% was 17 hours, the reaction time was considered satisfactory. Furthermore, since the episulfide group yield was 88%, the episulfide group yield was considered satisfactory. From these results, an overall decision was made that the process was acceptable.

Example 27

An episulfide compound was produced by the same method as that used in Example 1, according to the composition ratio of Table 1. As indicated in Table 4, since the reaction time taken until the epoxy group reaction rate reached 100% was 15 hours, the reaction time was considered satisfactory. Furthermore, since the episulfide group yield was 97%, the episulfide group yield was considered particu-

Example 28

An episulfide compound was produced by the same method as that used in Example 1, according to the composition ratio of Table 1. As indicated in Table 4, since the reaction time taken until the epoxy group reaction rate reached 100% was 12 hours, the reaction time was considered satisfactory. Furthermore, since the episulfide group yield was 96%, the episulfide group yield was considered particularly satisfactory. From these results, an overall decision was made that the process was acceptable.

Example 29

An episulfide compound was produced by the same method as that used in Example 1, according to the composition ratio of Table 1. As indicated in Table 4, since the reaction time taken until the epoxy group reaction rate reached 100% was 3 hours, the reaction time was considered particularly satisfactory. Furthermore, since the episulfide group yield was 96%, the episulfide group yield was considered particularly satisfactory. From these results, an overall decision was made that the process was acceptable.

Example 30

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 87%, the episulfide group yield was considered satisfactory. From these results, an overall decision was made that the process was acceptable.

Example 31

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 90%, the episulfide group yield was considered satisfactory. From these results, an overall decision was made that the process was acceptable.

Example 32

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 90%, the episulfide group yield was considered particularly satisfactory. From these results, an overall decision was made that the process was acceptable.

Example 33

An episulfide compound was produced by the same method as that used in Example 1, according to the composition ratio of Table 1. As indicated in Table 4, since the reaction time taken until the epoxy group reaction rate reached 100% was 3 hours, the reaction time was considered particularly satisfactory. Furthermore, since the episulfide group yield was 95%, the episulfide group yield was considered particularly satisfactory. From these results, an overall decision was made that the process was acceptable.

Example 34

An episulfide compound was produced by the same method as that used in Example 1, according to the composition ratio of Table 1. As indicated in Table 4, since the reaction time taken until the epoxy group reaction rate reached 100% was 8 hours, the reaction time was considered satisfactory. Furthermore, since the episulfide group yield was 96%, the episulfide group yield was considered particularly satisfactory. From these results, an overall decision was made that the process was acceptable.

Example 35

An episulfide compound was produced by the same method as that used in Example 1, according to the composition ratio of Table 1. As indicated in Table 4, since the reaction time taken until the epoxy group reaction rate reached 100% was 15 hours, the reaction time was considered satisfactory. Furthermore, since the episulfide group yield was 97%, the episulfide group yield was considered particularly satisfactory. From these results, an overall decision was made that the process was acceptable.

Example 36

An episulfide compound was produced by the same method as that used in Example 1, according to the composition ratio of Table 1. As indicated in Table 4, since the reaction time taken until the epoxy group reaction rate reached 100% was 1 hour, the reaction time was considered particularly satisfactory. Furthermore, since the episulfide group yield was 92%, the episulfide group yield was considered particularly satisfactory. From these results, an overall decision was made that the process was acceptable.

Example 37

An episulfide compound was produced by the same method as that used in Example 1 according to the composition ratio of Table 1, except that the electric immersion type cooling-heating unit and the water bath were changed to an oil bath including oil and a stirrer, and the temperature of the oil was set to 80° C. As indicated in Table 4, since the reaction time taken until the epoxy group reaction rate reached 100% was 1 hour, the reaction time was considered particularly satisfactory. Furthermore, since the episulfide group yield was 87%, the episulfide group yield was considered satisfactory. From these results, an overall decision was made that the process was acceptable.

Example 38

An episulfide compound was produced by the same method as that used in Example 1 according to the composition ratio of Table 1, except that the electric immersion type cooling-heating unit and the water bath were changed to an oil bath including oil and a stirrer, and the temperature was set to 100° C. As indicated in Table 4, since the reaction time taken until the epoxy group reaction rate reached 100% was 1 hour, the reaction time was considered particularly satisfactory. Furthermore, since the episulfide group yield was 83%, the episulfide group yield was considered satisfactory. From these results, an overall decision was made that the process was acceptable.

Example 39

An episulfide compound was produced by the same method as that used in Example 1, according to the composition ratio of Table 1. As indicated in Table 4, since the reaction time taken until the epoxy group reaction rate reached 100% was 6 hours, the reaction time was considered particularly satisfactory. Furthermore, since the episulfide group yield was 83%, the episulfide group yield was considered satisfactory. From these results, an overall decision was made that the process was acceptable.

Example 40

An episulfide compound was produced by the same method as that used in Example 1, according to the composition ratio of Table 1. As indicated in Table 4, since the reaction time taken until the epoxy group reaction rate reached 100% was 6 hours, the reaction time was considered particularly satisfactory. Furthermore, since the episulfide group yield was 87%, the episulfide group yield was considered satisfactory. From these results, an overall decision was made that the process was acceptable.

Example 41

An episulfide compound was produced by the same method as that used in Example 1, according to the composition ratio of Table 1. As indicated in Table 4, since the reaction time taken until the epoxy group reaction rate reached 100% was 2 hours, the reaction time was considered particularly satisfactory. Furthermore, since the episulfide group yield was 87%, the episulfide group yield was considered satisfactory. From these results, an overall decision was made that the process was acceptable.

Example 42

An episulfide compound was produced by the same method as that used in Example 1, according to the composition ratio of Table 1. As indicated in Table 4, since the reaction time taken until the epoxy group reaction rate reached 100% was 3 hours, the reaction time was considered particularly satisfactory. Furthermore, since the episulfide group yield was 86%, the episulfide group yield was considered satisfactory. From these results, an overall decision was made that the process was acceptable.

Example 43

An episulfide compound was produced by the same method as that used in Example 1, according to the composition ratio of Table 1. As indicated in Table 4, since the reaction time taken until the epoxy group reaction rate reached 100% was 3 hours, the reaction time was considered particularly satisfactory. Furthermore, since the episulfide group yield was 92%, the episulfide group yield was considered satisfactory. From these results, an overall decision was made that the process was acceptable.

Example 44

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 91%, the episulfide group yield was considered particularly satisfactory. From these results, an overall decision was made that the process was acceptable.

Example 45

An episulfide compound was produced by the same method as that used in Example 1, according to the composition ratio of Table 2. As indicated in Table 5, since the reaction time taken until the epoxy group reaction rate reached 100% was 1 hour, the reaction time was considered particularly satisfactory. Furthermore, since the episulfide group yield was 94%, the episulfide group yield was considered particularly satisfactory. From these results, an overall decision was made that the process was acceptable.

Example 46

An episulfide compound was produced by the same method as that used in Example 1, according to the composition ratio of Table 2. As indicated in Table 5, since the reaction time taken until the epoxy group reaction rate reached 100% was 3 hours, the reaction time was considered particularly satisfactory. Furthermore, since the episulfide group yield was 92%, the episulfide group yield was considered particularly satisfactory. From these results, an overall decision was made that the process was acceptable.

Example 47

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 95%, the episulfide group yield was considered particularly satisfactory. From these results, an overall decision was made that the process was acceptable.

Example 48

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 91%, the episulfide group yield was considered particularly satisfactory. From these results, an overall decision was made that the process was acceptable.

Example 49

An episulfide compound was produced by the same method as that used in Example 1, according to the composition ratio of Table 2. As indicated in Table 5, since the reaction time taken until the epoxy group reaction rate reached 100% was 4 hours, the reaction time was considered

Example 50

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 94%, the episulfide group yield was considered particularly satisfactory. From these results, an overall decision was made that the process was acceptable.

Example 51

An episulfide compound was produced by the same method as that used in Example 1, according to the composition ratio of Table 2. As indicated in Table 5, since the reaction time taken until the epoxy group reaction rate reached 100% was 3 hours, the reaction time was considered particularly satisfactory. Furthermore, since the episulfide group yield was 93%, the episulfide group yield was considered particularly satisfactory. From these results, an overall decision was made that the process was acceptable.

Example 52

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 94%, the episulfide group yield was considered particularly satisfactory. From these results, an overall decision was made that the process was acceptable.

Example 53

An episulfide compound was produced by the same method as that used in Example 1, according to the composition ratio of Table 2. As indicated in Table 5, since the reaction time taken until the epoxy group reaction rate reached 100% was 4 hours, the reaction time was considered particularly satisfactory. Furthermore, since the episulfide group yield was 94%, the episulfide group yield was considered particularly satisfactory. From these results, an overall decision was made that the process was acceptable.

Example 54

An episulfide compound was produced by the same method as that used in Example 1, according to the composition ratio of Table 2. As indicated in Table 5, since the reaction time taken until the epoxy group reaction rate reached 100% was 6 hours, the reaction time was considered particularly satisfactory. Furthermore, since the episulfide group yield was 90%, the episulfide group yield was considered particularly satisfactory. From these results, an overall decision was made that the process was acceptable.

Example 55

An episulfide compound was produced by the same method as that used in Example 1, according to the composition ratio of Table 2. As indicated in Table 5, since the reaction time taken until the epoxy group reaction rate reached 100% was 5 hours, the reaction time was considered particularly satisfactory. Furthermore, since the episulfide group yield was 88%, the episulfide group yield was considered satisfactory. From these results, an overall decision was made that the process was acceptable.

Example 56

An episulfide compound was produced by the same method as that used in Example 1, according to the composition ratio of Table 2. As indicated in Table 5, since the reaction time taken until the epoxy group reaction rate reached 100% was 6 hours, the reaction time was considered particularly satisfactory. Furthermore, since the episulfide group yield was 83%, the episulfide group yield was considered satisfactory. From these results, an overall decision was made that the process was acceptable.

Example 57

An episulfide compound was produced by the same method as that used in Example 1, according to the composition ratio of Table 2. As indicated in Table 5, since the reaction time taken until the epoxy group reaction rate reached 100% was 4 hours, the reaction time was considered particularly satisfactory. Furthermore, since the episulfide group yield was 87%, the episulfide group yield was considered satisfactory. From these results, an overall decision was made that the process was acceptable.

Example 58

An episulfide compound was produced by the same method as that used in Example 1, according to the composition ratio of Table 2. As indicated in Table 5, since the reaction time taken until the epoxy group reaction rate reached 100% was 4 hours, the reaction time was considered particularly satisfactory. Furthermore, since the episulfide group yield was 88%, the episulfide group yield was considered satisfactory. From these results, an overall decision was made that the process was acceptable.

Example 59

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 87%, the episulfide group yield was considered satisfactory. From these results, an overall decision was made that the process was acceptable.

Example 60

An episulfide compound was produced by the same method as that used in Example 1 according to the composition ratio of Table 2, except that the mixing index $\epsilon$ was used in addition to the mixing index $\beta$. As indicated in Table 5, since the reaction time taken until the epoxy group reaction rate reached 100% was 6 hours, the reaction time was considered particularly satisfactory. Furthermore, since the episulfide group yield was 94%, the episulfide group yield

Example 61

An episulfide compound was produced by the same method as that used in Example 1, according to the composition ratio of Table 2. As indicated in Table 5, since the reaction time taken until the epoxy group reaction rate reached 100% was 5 hours, the reaction time was considered particularly satisfactory. Furthermore, since the episulfide group yield was 90%, the episulfide group yield was considered particularly satisfactory. From these results, an overall decision was made that the process was acceptable.

Example 62

An episulfide compound was produced by the same method as that used in Example 1, according to the composition ratio of Table 2. As indicated in Table 5, since the reaction time taken until the epoxy group reaction rate reached 100% was 5 hours, the reaction time was considered particularly satisfactory. Furthermore, since the episulfide group yield was 91%, the episulfide group yield was considered particularly satisfactory. From these results, an overall decision was made that the process was acceptable.

Example 63

An episulfide compound was produced by the same method as that used in Example 1, according to the composition ratio of Table 2. As indicated in Table 5, since the reaction time taken until the epoxy group reaction rate reached 100% was 5 hours, the reaction time was considered particularly satisfactory. Furthermore, since the episulfide group yield was 90%, the episulfide group yield was considered particularly satisfactory. From these results, an overall decision was made that the process was acceptable.

Example 64

An episulfide compound was produced by the same method as that used in Example 1 according to the composition ratio of Table 2, except that the mixing index $\epsilon$ was used in addition to the mixing index $\beta$. As indicated in Table 5, since the reaction time taken until the epoxy group reaction rate reached 100% was 4 hours, the reaction time was considered particularly satisfactory. Furthermore, since the episulfide group yield was 92%, the episulfide group yield was considered particularly satisfactory. From these results, an overall decision was made that the process was acceptable.

Example 65

An episulfide compound was produced by the same method as that used in Example 1, according to the composition ratio of Table 2. As indicated in Table 5, since the reaction time taken until the epoxy group reaction rate reached 100% was 12 hours, the reaction time was considered satisfactory. Furthermore, since the episulfide group yield was 83%, the episulfide group yield was considered satisfactory. From these results, an overall decision was made that the process was acceptable.

Example 66

An episulfide compound was produced by the same method as that used in Example 1, according to the composition ratio of Table 2. As indicated in Table 5, since the reaction time taken until the epoxy group reaction rate reached 100% was 8 hours, the reaction time was considered satisfactory. Furthermore, since the episulfide group yield was 91%, the episulfide group yield was considered particularly satisfactory. From these results, an overall decision was made that the process was acceptable.

Example 67

An episulfide compound was produced by the same method as that used in Example 1, according to the composition ratio of Table 2. As indicated in Table 5, since the reaction time taken until the epoxy group reaction rate reached 100% was 18 hours, the reaction time was considered satisfactory. Furthermore, since the episulfide group yield was 81%, the episulfide group yield was considered satisfactory. From these results, an overall decision was made that the process was acceptable.

Example 68

An episulfide compound was produced by the same method as that used in Example 1, according to the composition ratio of Table 2. As indicated in Table 5, since the reaction time taken until the epoxy group reaction rate reached 100% was 22 hours, the reaction time was considered satisfactory. Furthermore, since the episulfide group yield was 84%, the episulfide group yield was considered satisfactory. From these results, an overall decision was made that the process was acceptable.

Example 69

An episulfide compound was produced by the same method as that used in Example 1, according to the composition ratio of Table 2. As indicated in Table 5, since the reaction time taken until the epoxy group reaction rate reached 100% was 15 hours, the reaction time was considered satisfactory. Furthermore, since the episulfide group yield was 93%, the episulfide group yield was considered particularly satisfactory. From these results, an overall decision was made that the process was acceptable.

Example 70

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 94%, the episulfide group yield was considered particularly satisfactory. From these results, an overall decision was made that the process was acceptable.

Example 71

An episulfide compound was produced by the same method as that used in Example 1, according to the composition ratio of Table 2. As indicated in Table 5, since the reaction time taken until the epoxy group reaction rate reached 100% was 1 hour, the reaction time was considered particularly satisfactory. Furthermore, since the episulfide group yield was 96%, the episulfide group yield was consid-

Example 72

An episulfide compound was produced by the same method as that used in Example 1, according to the composition ratio of Table 2. As indicated in Table 5, since the reaction time taken until the epoxy group reaction rate reached 100% was 15 hours, the reaction time was considered satisfactory. Furthermore, since the episulfide group yield was 90%, the episulfide group yield was considered particularly satisfactory. From these results, an overall decision was made that the process was acceptable.

Example 73

An episulfide compound was produced by the same method as that used in Example 1, according to the composition ratio of Table 2. As indicated in Table 5, since the reaction time taken until the epoxy group reaction rate reached 100% was 1 hour, the reaction time was considered particularly satisfactory. Furthermore, since the episulfide group yield was 95%, the episulfide group yield was considered particularly satisfactory. From these results, an overall decision was made that the process was acceptable.

Example 74

An episulfide compound was produced by the same method as that used in Example 1, according to the composition ratio of Table 2. As indicated in Table 5, since the reaction time taken until the epoxy group reaction rate reached 100% was 18 hours, the reaction time was considered satisfactory. Furthermore, since the episulfide group yield was 90%, the episulfide group yield was considered particularly satisfactory. From these results, an overall decision was made that the process was acceptable.

Example 75

An episulfide compound was produced by the same method as that used in Example 1, according to the composition ratio of Table 2. As indicated in Table 5, since the reaction time taken until the epoxy group reaction rate reached 100% was 4 hours, the reaction time was considered particularly satisfactory. Furthermore, since the episulfide group yield was 83%, the episulfide group yield was considered satisfactory. From these results, an overall decision was made that the process was acceptable.

Example 76

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 92%, the episulfide group yield was considered particularly satisfactory. From these results, an overall decision was made that the process was acceptable.

Example 77

An episulfide compound was produced by the same method as that used in Example 1, according to the composition ratio of Table 2. As indicated in Table 5, since the reaction time taken until the epoxy group reaction rate reached 100% was 1 hour, the reaction time was considered particularly satisfactory. Furthermore, since the episulfide group yield was 94%, the episulfide group yield was considered particularly satisfactory. From these results, an overall decision was made that the process was acceptable.

Example 78

An episulfide compound was produced by the same method as that used in Example 1, according to the composition ratio of Table 2. As indicated in Table 5, since the reaction time taken until the epoxy group reaction rate reached 100% was 20 hours, the reaction time was considered satisfactory. Furthermore, since the episulfide group yield was 91%, the episulfide group yield was considered particularly satisfactory. From these results, an overall decision was made that the process was acceptable.

Example 79

An episulfide compound was produced by the same method as that used in Example 1, according to the composition ratio of Table 2. As indicated in Table 5, since the reaction time taken until the epoxy group reaction rate reached 100% was 2 hours, the reaction time was considered particularly satisfactory. Furthermore, since the episulfide group yield was 92%, the episulfide group yield was considered particularly satisfactory. From these results, an overall decision was made that the process was acceptable.

Example 80

An episulfide compound was produced by the same method as that used in Example 1, according to the composition ratio of Table 2. As indicated in Table 5, since the reaction time taken until the epoxy group reaction rate reached 100% was 9 hours, the reaction time was considered satisfactory. Furthermore, since the episulfide group yield was 88%, the episulfide group yield was considered satisfactory. From these results, an overall decision was made that the process was acceptable.

Example 81

An episulfide compound was produced by the same method as that used in Example 1, according to the composition ratio of Table 2. As indicated in Table 5, since the reaction time taken until the epoxy group reaction rate reached 100% was 12 hours, the reaction time was considered satisfactory. Furthermore, since the episulfide group yield was 85%, the episulfide group yield was considered satisfactory. From these results, an overall decision was made that the process was acceptable.

Example 82

An episulfide compound was produced by the same method as that used in Example 1, according to the composition ratio of Table 2. As indicated in Table 5, since the reaction time taken until the epoxy group reaction rate reached 100% was 12 hours, the reaction time was considered satisfactory. Furthermore, since the episulfide group yield was 85%, the episulfide group yield was considered satisfactory. From these results, an overall decision was made that the process was acceptable.

Example 83

An episulfide compound was produced by the same method as that used in Example 1, according to the composition ratio of Table 2. As indicated in Table 5, since the reaction time taken until the epoxy group reaction rate reached 100% was 16 hours, the reaction time was considered satisfactory. Furthermore, since the episulfide group yield was 82%, the episulfide group yield was considered satisfactory. From these results, an overall decision was made that the process was acceptable.

Example 84

An episulfide compound was produced by the same method as that used in Example 1, according to the composition ratio of Table 2. As indicated in Table 5, since the reaction time taken until the epoxy group reaction rate reached 100% was 20 hours, the reaction time was considered satisfactory. Furthermore, since the episulfide group yield was 82%, the episulfide group yield was considered satisfactory. From these results, an overall decision was made that the process was acceptable.

Example 85

An episulfide compound was produced by the same method as that used in Example 1, according to the composition ratio of Table 2. As indicated in Table 5, since the reaction time taken until the epoxy group reaction rate reached 100% was 23 hours, the reaction time was considered satisfactory. Furthermore, since the episulfide group yield was 80%, the episulfide group yield was considered satisfactory. From these results, an overall decision was made that the process was acceptable.

Example 86

An episulfide compound was produced by the same method as that used in Example 1, according to the composition ratio of Table 2. As indicated in Table 5, since the reaction time taken until the epoxy group reaction rate reached 100% was 22 hours, the reaction time was considered satisfactory. Furthermore, since the episulfide group yield was 81%, the episulfide group yield was considered satisfactory. From these results, an overall decision was made that the process was acceptable.

Comparative Example 1

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 32 hours, the reaction time was considered poor. Furthermore, since the episulfide group yield was 72%, the episulfide group yield was considered poor. From these results, an overall decision was made that the process was unacceptable.

Comparative Example 2

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 150 hours, the reaction time was considered poor. Furthermore, since the episulfide group yield was 69%, the episulfide group yield was considered poor. From these results, an overall decision was made that the process was unacceptable.

Comparative Example 3

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 4 hours, the reaction time was considered particularly satisfactory. Furthermore, since the episulfide group yield was 60%, the episulfide group yield was considered poor. From these results, an overall decision was made that the process was unacceptable.

Comparative Example 4

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 130 hours, the reaction time was considered poor. Furthermore, since the episulfide group yield was 74%, the episulfide group yield was considered poor. From these results, an overall decision was made that the process was unacceptable.

Comparative Example 5

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 4 hours, the reaction time was considered particularly satisfactory. Furthermore, since the episulfide group yield was 53%, the episulfide group yield was considered poor. From these results, an overall decision was made that the process was unacceptable. In this Comparative Example, it was confirmed that thiourea remained undissolved in the reaction liquid.

Comparative Example 6

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 400 hours, the reaction time was considered poor. Furthermore, since the episulfide group yield was 76%, the episulfide group yield was considered poor. From these results, an overall decision was made that the process was unacceptable.

Comparative Example 7

An episulfide compound was produced by the same method as that used in Example 1 according to the composition ratio of Table 3, except that the mixing index $\epsilon$ was used instead of the mixing index $\beta$, the electric immersion cooling-heating unit and the water bath were changed to an oil bath including oil and a stirrer, and the temperature of the oil was set to 100° C. As indicated in Table 6, since the reaction time taken until the epoxy group reaction rate reached 100% was 8 hours, the reaction time was considered satisfactory. Furthermore, since the episulfide group yield was 58%, the episulfide group yield was considered poor. From these results, an overall decision was made that the process was unacceptable.

Comparative Example 8

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 25 hours, the reaction time was considered poor. Furthermore, since the episulfide group yield was 62%, the episulfide group yield was considered poor. From these results, an overall decision was made that the process was unacceptable.

Comparative Example 9

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 30 hours, the reaction time was considered poor. Furthermore, since the episulfide group yield was 55%, the episulfide group yield was considered poor. From these results, an overall decision was made that the process was unacceptable.

Comparative Example 10

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 28 hours, the reaction time was considered poor. Furthermore, since the episulfide group yield was 50%, the episulfide group yield was considered poor. From these results, an overall decision was made that the process was unacceptable.

Comparative Example 11

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 33 hours, the reaction time was considered poor. Furthermore, since the episulfide group yield was 57%, the episulfide group yield was considered poor. From these results, an overall decision was made that the process was unacceptable.

Comparative Example 12

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 40 hours, the reaction time was considered poor. Furthermore, since the episulfide group yield was 60%, the episulfide group yield was considered poor. From these results, an overall decision was made that the process was unacceptable.

Comparative Example 13

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 28 hours, the reaction time was considered poor. Furthermore, since the episulfide group yield was 54%, the episulfide group yield was considered poor. From these results, an overall decision was made that the process was unacceptable.

Comparative Example 14

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 30 hours, the reaction time was considered poor. Furthermore, since the episulfide group yield was 54%, the episulfide group yield was considered poor. From these results, an overall decision was made that the process was unacceptable.

Comparative Example 15

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 32 hours, the reaction time was considered poor. Furthermore, since the episulfide group yield was 58%, the episulfide group yield was considered poor. From these results, an overall decision was made that the process was unacceptable.

Comparative Example 16

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 29 hours, the reaction time was considered poor. Furthermore, since the episulfide group yield was 52%, the episulfide group yield was considered poor. From these results, an overall decision was made that the process was unacceptable.

Comparative Example 17

An episulfide compound was produced by the same method as that used in Example 1 according to the composition ratio of Table 3, except that the mixing index $\epsilon$ was used instead of the mixing index $\beta$. As indicated in Table 6, since the reaction time taken until the epoxy group reaction rate reached 100% was 34 hours, the reaction time was considered poor. Furthermore, since the episulfide group yield was 55%, the episulfide group yield was considered poor. From these results, an overall decision was made that the process was unacceptable.

Comparative Example 18

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 40 hours, the reaction time was considered poor. Furthermore, since the episulfide group yield was 57%, the episulfide group yield was considered poor. From these results, an overall decision was made that the process was unacceptable.

Comparative Example 19

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 26 hours, the reaction time was considered poor. Furthermore, since the episulfide group yield was 49%, the episulfide group yield was considered poor. From these results, an overall decision was made that the process was unacceptable.

Comparative Example 20

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 28 hours, the reaction time was considered poor. Furthermore, since the episulfide group yield was 50%, the episulfide group yield was considered poor. From these results, an overall decision was made that the process was unacceptable.

Comparative Example 21

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 55 hours, the reaction time was considered poor. Furthermore, since the episulfide group yield was 60%, the episulfide group yield was considered poor. From these results, an overall decision was made that the process was unacceptable.

Comparative Example 22

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 60 hours, the reaction time was considered poor. Furthermore, since the episulfide group yield was 62%, the episulfide group yield was considered poor. From these results, an overall decision was made that the process was unacceptable.

Comparative Example 23

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 17 hours, the reaction time was considered satisfactory. Furthermore, since the episulfide group yield was 62%, the episulfide group yield was considered poor. From these results, an overall decision was made that the process was unacceptable.

Comparative Example 24

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 12 hours, the reaction time was considered satisfactory. Furthermore, since the episulfide group yield was 53%, the episulfide group yield was considered poor. From these results, an overall decision was made that the process was unacceptable.

Comparative Example 25

An episulfide compound was produced by the same method as that used in Example 1 according to the composition ratio of Table 3, except that the mixing index ϵ was used instead of the mixing index β, the electric immersion type cooling-heating unit and the water bath were changed to an oil bath including oil and a stirrer, and the temperature was set to 80° C. As indicated in Table 6, since the reaction time taken until the epoxy group reaction rate reached 100% was 8 hours, the reaction time was considered satisfactory. Furthermore, since the episulfide group yield was 66%, the episulfide group yield was considered poor. From these results, an overall decision was made that the process was unacceptable.

Comparative Example 26

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 15 hours, the reaction time was considered satisfactory. Furthermore, since the episulfide group yield was 62%, the episulfide group yield was considered poor. From these results, an overall decision was made that the process was unacceptable.

Comparative Example 27

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 100 hours, the reaction time was considered poor. Furthermore, since the episulfide group yield was 66%, the episulfide group yield was considered poor. From these results, an overall decision was made that the process was unacceptable.

Comparative Example 28

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 30 hours, the reaction time was considered poor. Furthermore, since the episulfide group yield was 60%, the episulfide group yield was considered poor. From these results, an overall decision was made that the process was unacceptable.

Comparative Example 29

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 35 hours, the reaction time was considered poor. Furthermore, since the episulfide group yield was 55%, the episulfide group yield was considered poor. From these results, an overall decision was made that the process was unacceptable.

Comparative Example 30

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 60 hours, the reaction time was considered poor. Furthermore, since the episulfide group yield was 50%, the episulfide group yield was considered poor. From these results, an overall decision was made that the process was unacceptable.

Comparative Example 31

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 48 hours, the reaction time was considered poor. Furthermore, since the episulfide group yield was 58%, the episulfide group yield was considered poor. From these results, an overall decision was made that the process was unacceptable.

Comparative Example 32

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 90 hours, the reaction time was considered poor. Furthermore, since the episulfide group yield was 52%, the episulfide group yield was considered poor. From these results, an overall decision was made that the process was unacceptable.

Comparative Example 33

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 84 hours, the reaction time was considered poor. Furthermore, since the episulfide group yield was 55%, the episulfide group yield was considered poor. From these results, an overall decision was made that the process was unacceptable.

Comparative Example 34

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 76 hours, the reaction time was considered poor. Furthermore, since the episulfide group yield was 60%, the episulfide group yield was considered poor. From these results, an overall decision was made that the process was unacceptable.

Comparative Example 35

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 5 hours, the reaction time was considered particularly satisfactory. Furthermore, since the episulfide group yield was 63%, the episulfide group yield was considered poor. From these results, an overall decision was made that the process was unacceptable.

Comparative Example 36

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 7 hours, the reaction time was considered satisfactory. Furthermore, since the episulfide group yield was 56%, the episulfide group yield was considered poor. From these results, an overall decision was made that the process was unacceptable.

Comparative Example 37

An episulfide compound was produced by the same method as that used in Example 1 according to the composition ratio of Table 3, except that the mixing index ε was used instead of the mixing index β. As indicated in Table 6, since the reaction time taken until the epoxy group reaction rate reached 100% was 48 hours, the reaction time was considered poor. Furthermore, since the episulfide group yield was 50%, the episulfide group yield was considered poor. From these results, an overall decision was made that the process was unacceptable.

Comparative Example 38

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 8 hours, the reaction time was considered satisfactory. Furthermore, since the episulfide group yield was 52%, the episulfide group yield was considered poor. From these results, an overall decision was made that the process was unacceptable.

Comparative Example 39

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 38 hours, the reaction time was considered poor. Furthermore, since the episulfide group yield was 50%, the episulfide group yield was considered poor. From these results, since the reaction time and the episulfide group yield were both poor, an overall decision was made that the process was unacceptable.

Comparative Example 40

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 10 hours, the reaction time was considered satisfactory. Furthermore, since the episulfide group yield was 52%, the episulfide group yield was considered poor. From these results, an overall decision was made that the process was unacceptable.

Comparative Example 41

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 16 hours, the reaction time was considered satisfactory. Furthermore, since the episulfide group yield was 60%, the episulfide group yield was considered poor. From these results, an overall decision was made that the process was unacceptable.

Comparative Example 42

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 8 hours, the reaction time was considered satisfactory. Furthermore, since the episulfide group yield was 54%, the episulfide group yield was considered poor. From these results, an overall decision was made that the process was unacceptable.

Comparative Example 43

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 60 hours, the reaction time was considered poor. Furthermore, since the episulfide group yield was 44%, the episulfide group yield was considered poor. From these results, an overall decision was made that the process was unacceptable.

Comparative Example 44

An episulfide compound was produced by the same method as that used in Example 1 according to the composition ratio of Table 3, except that the mixing index ϵ was used instead of the mixing index β. As indicated in Table 6, since the reaction time taken until the epoxy group reaction rate reached 100% was 12 hours, the reaction time was considered satisfactory. Furthermore, since the episulfide group yield was 52%, the episulfide group yield was considered poor. From these results, an overall decision was made that the process was unacceptable.

TABLE 1

| | Polyhydric hydroxyl compound | | Monohydric hydroxyl | | Epoxy compound | | Thiating agent | | Additive compound | |
|---|---|---|---|---|---|---|---|---|---|---|
| | Name | mass % | Name | mass % | Name | mass % | Name | mass % | Name | mass % |
| Example 1 | EG | 63 | — | — | PGE | 18 | TU | 18 | — | — |
| Example 2 | 12PG | 63 | — | — | PGE | 18 | TU | 18 | — | — |
| Example 3 | 13PG | 63 | — | — | PGE | 18 | TU | 18 | — | — |
| Example 4 | 12BD | 64 | — | — | PGE | 18 | TU | 18 | — | — |
| Example 5 | 13BD | 68 | — | — | PGE | 16 | TU | 16 | — | — |
| Example 6 | 14BD | 66 | — | — | PGE | 17 | TU | 17 | — | — |
| Example 7 | 12PD | 72 | — | — | PGE | 14 | TU | 14 | — | — |
| Example 8 | 12HD | 81 | — | — | PGE | 10 | TU | 10 | — | — |
| Example 9 | 12OD | 86 | — | — | PGE | 7 | TU | 7 | — | — |
| Example 10 | GL | 81 | — | — | PGE | 10 | TU | 10 | — | — |
| Example 11 | DEG | 72 | — | — | PGE | 14 | TU | 14 | — | — |
| Example 12 | TEG | 75 | — | — | PGE | 13 | TU | 13 | — | — |
| Example 13 | TEEG | 75 | — | — | PGE | 13 | TU | 13 | — | — |
| Example 14 | PEEG | 77 | — | — | PGE | 11 | TU | 12 | — | — |

TABLE 1-continued

| | Polyhydric hydroxyl compound | | Monohydric hydroxyl | | Epoxy compound | | Thiating agent | | Additive compound | |
|---|---|---|---|---|---|---|---|---|---|---|
| | Name | mass % | Name | mass % | Name | mass % | Name | mass % | Name | mass % |
| Example 15 | HEEG | 79 | — | — | PGE | 10 | TU | 10 | — | — |
| Example 16 | OCEG | 70 | SW | 14 | PGE | 8 | TU | 8 | — | — |
| Example 17 | DDEG | 71 | SW | 14 | PGE | 7 | TU | 7 | — | — |
| Example 18 | PEG200 | 75 | — | — | PGE | 13 | TU | 13 | — | — |
| Example 19 | PEG300 | 76 | — | — | PGE | 12 | TU | 12 | — | — |
| Example 20 | PEG400 | 77 | — | — | PGE | 11 | TU | 12 | — | — |
| Example 21 | 12BD | 84 | — | — | PGE | 5 | TU | 11 | — | — |
| Example 22 | 12BD | 73 | — | — | PGE | 7 | TU | 20 | — | — |
| Example 23 | 12BD | 87 | — | — | PGE | 2 | TU | 10 | — | — |
| Example 24 | 12BD | 61 | — | — | PGE | 22 | TU | 17 | — | — |
| Example 25 | 12BD | 63 | — | — | PGE | 23 | TU | 14 | — | — |
| Example 26 | 12BD | 55 | — | — | PGE | 30 | TU | 15 | — | — |
| Example 27 | 12PG | 98 | — | — | PGE | 1 | TU | 1 | — | — |
| Example 28 | 12PG | 97 | — | — | PGE | 1 | TU | 1 | — | — |
| Example 29 | 12PG | 96 | — | — | PGE | 2 | TU | 2 | — | — |
| Example 30 | 12PG | 50 | — | — | PGE | 25 | TU | 25 | — | — |
| Example 31 | 12PG | 53 | — | — | PGE | 23 | TU | 24 | — | — |
| Example 32 | 12PG | 55 | — | — | PGE | 23 | TU | 23 | — | — |
| Example 33 | 12BD | 64 | — | — | PGE | 18 | TU | 18 | — | — |
| Example 34 | 12BD | 64 | — | — | PGE | 18 | TU | 18 | — | — |
| Example 35 | 12BD | 64 | — | — | PGE | 18 | TU | 18 | — | — |
| Example 36 | 12BD | 64 | — | — | PGE | 18 | TU | 18 | — | — |
| Example 37 | 12BD | 64 | — | — | PGE | 18 | TU | 18 | — | — |
| Example 38 | 12BD | 64 | — | — | PGE | 18 | TU | 18 | — | — |
| Example 39 | 12PD | 89 | — | — | EO | 3 | TU | 9 | — | — |
| Example 40 | 12BD | 72 | — | — | PO | 8 | TU | 20 | — | — |
| Example 41 | 13PG | 73 | — | — | 12EB | 9 | TU | 18 | — | — |
| Example 42 | 12BD | 70 | — | — | 12EP | 11 | TU | 19 | — | — |
| Example 43 | 12PG | 68 | — | — | 12EH | 13 | TU | 20 | — | — |

TABLE 2

| | Polyhydric hydroxyl compound | | Monohydric hydroxyl compound | | Epoxy compound | | Thiating agent | | Additive compound | |
|---|---|---|---|---|---|---|---|---|---|---|
| | Name | mass % | Name | mass % | Name | mass % | Name | mass % | Name | mass % |
| Example 44 | 12BD | 67 | — | — | 12EHP | 14 | TU | 19 | — | — |
| Example 45 | 12BD | 66 | — | — | 12EO | 16 | TU | 18 | — | — |
| Example 46 | 12BD | 64 | — | — | 12ED | 18 | TU | 18 | — | — |
| Example 47 | 12BD | 62 | — | — | 12EDD | 21 | TU | 17 | — | — |
| Example 48 | 12BD | 60 | — | — | 12ETD | 23 | TU | 17 | — | — |
| Example 49 | 12BD | 58 | — | — | 12EHD | 26 | TU | 16 | — | — |
| Example 50 | 12BD | 56 | — | — | 12EOD | 28 | TU | 16 | — | — |
| Example 51 | 12BD | 55 | — | — | 12EEC | 30 | TU | 15 | — | — |
| Example 52 | 13BD | 68 | — | — | Bis-A-1 | 18 | TU | 14 | — | — |
| Example 53 | 13BD | 67 | — | — | Hydrogenated Bis-A | 19 | TU | 14 | — | — |
| Example 54 | 12BD | 75 | — | — | Bis-A-2 | 19 | TU | 6 | — | — |
| Example 55 | 12BD | 81 | — | — | Bis-A-3 | 15 | TU | 4 | — | — |
| Example 56 | 12BD | 83 | — | — | Bis-A-4 | 14 | TU | 3 | — | — |
| Example 57 | 12BD | 67 | — | — | PGE | 14 | TCK | 19 | — | — |
| Example 58 | 12BD | 65 | — | — | PGE | 17 | TCN | 18 | — | — |
| Example 59 | 12BD | 55 | — | — | PGE | 22 | TCA | 23 | — | — |
| Example 60 | 12BD | 60 | MN | 6 | PGE | 17 | TU | 17 | — | — |
| Example 61 | 12BD | 60 | — | — | PGE | 17 | TU | 17 | TOL | 6 |
| Example 62 | 12BD | 60 | — | — | PGE | 17 | TU | 17 | AN | 6 |
| Example 63 | 12BD | 60 | — | — | PGE | 17 | TU | 17 | THF | 6 |
| Example 64 | 12BD | 60 | SW | 6 | PGE | 17 | TU | 17 | — | — |
| Example 65 | 12BD | 70 | — | — | C50 | 11 | TU | 20 | — | — |
| Example 66 | 12BD | 68 | — | — | C60 | 12 | TU | 19 | — | — |
| Example 67 | 12BD | 67 | — | — | C70 | 14 | TU | 19 | — | — |
| Example 68 | 12BD | 66 | — | — | C80 | 15 | TU | 19 | — | — |
| Example 69 | 12BD | 66 | — | — | CEL | 16 | TU | 18 | — | — |
| Example 70 | 12BD | 69 | — | — | BEDS | 12 | TU | 19 | — | — |
| Example 71 | 12BD | 62 | — | — | BGTD | 21 | TU | 17 | — | — |
| Example 72 | 12BD | 61 | — | — | BCTD | 22 | TU | 17 | — | — |
| Example 73 | 12BD | 62 | — | — | TGCS | 20 | TU | 17 | — | — |
| Example 74 | 12BD | 62 | — | — | TCCS | 21 | TU | 17 | — | — |

TABLE 2-continued

|  | Polyhydric hydroxyl compound | | Monohydric hydroxyl compound | | Epoxy compound | | Thiating agent | | Additive compound | |
|---|---|---|---|---|---|---|---|---|---|---|
|  | Name | mass % | Name | mass % | Name | mass % | Name | mass % | Name | mass % |
| Example 75 | 12BD | 71 | — | — | BDMO | 9 | TU | 20 | — | — |
| Example 76 | 12BD | 68 | — | — | EPHE | 12 | TU | 19 | — | — |
| Example 77 | 12BD | 67 | — | — | AGE | 14 | TU | 19 | — | — |
| Example 78 | 12BD | 66 | — | — | EVCH | 15 | TU | 19 | — | — |
| Example 79 | 12BD | 65 | — | — | GLMT | 17 | TU | 18 | — | — |
| Example 80 | ETT | 15 | SW | 74 | PGE | 6 | TU | 6 | — | — |
| Example 81 | XT | 15 | SW | 74 | PGE | 6 | TU | 6 | — | — |
| Example 82 | DMT | 15 | SW | 74 | PGE | 6 | TU | 6 | — | — |
| Example 83 | VLT | 12 | SW | 78 | PGE | 5 | TU | 5 | — | — |
| Example 84 | DLC | 13 | SW | 76 | PGE | 5 | TU | 5 | — | — |
| Example 85 | SCR | 12 | SW | 77 | PGE | 5 | TU | 5 | — | — |
| Example 86 | MEOS | 96 | — | — | PGE | 2 | TU | 2 | — | — |

TABLE 3

|  | Polyhydric hydroxyl compound | | Monohydric hydroxyl | | Epoxy compound | | Thiating agent | | Additive compound | |
|---|---|---|---|---|---|---|---|---|---|---|
|  | Name | mass % | Name | mass % | Name | mass % | Name | mass % | Name | mass % |
| Comp. Example 1 | — | — | MN | 93 | PGE | 4 | TU | 4 | — | — |
| Comp. Example 2 | — | — | MN | 89 | PGE | 7 | TU | 4 | — | — |
| Comp. Example 3 | — | — | MN | 95 | PGE | 1 | TU | 4 | — | — |
| Comp. Example 4 | — | — | MN | 98 | PGE | 1 | TU | 1 | — | — |
| Comp. Example 5 | — | — | MN | 56 | PGE | 22 | TU | 22 | — | — |
| Comp. Example 6 | — | — | MN | 93 | PGE | 4 | TU | 4 | — | — |
| Comp. Example 7 | — | — | MN | 93 | PGE | 4 | TU | 4 | — | — |
| Comp. Example 8 | — | — | MN | 95 | EO | 1 | TU | 4 | — | — |
| Comp. Example 9 | — | — | MN | 95 | PO | 1 | TU | 4 | — | — |
| Comp. Example 10 | — | — | MN | 94 | 12EB | 2 | TU | 4 | — | — |
| Comp. Example 11 | — | — | MN | 94 | 12EP | 2 | TU | 4 | — | — |
| Comp. Example 12 | — | — | MN | 94 | 12EH | 2 | TU | 4 | — | — |
| Comp. Example 13 | — | — | MN | 93 | 12EHP | 3 | TU | 4 | — | — |
| Comp. Example 14 | — | — | MN | 93 | 12EO | 3 | TU | 4 | — | — |
| Comp. Example 15 | — | — | MN | 93 | 12ED | 4 | TU | 4 | — | — |
| Comp. Example 16 | — | — | MN | 92 | 12EDD | 4 | TU | 4 | — | — |
| Comp. Example 17 | — | — | MN | 91 | 12ETD | 5 | TU | 4 | — | — |
| Comp. Example 18 | — | — | MN | 91 | 12EHD | 6 | TU | 4 | — | — |
| Comp. Example 19 | — | — | MN | 90 | 12EOD | 6 | TU | 4 | — | — |
| Comp. Example 20 | — | — | MN | 89 | 12EEC | 7 | TU | 4 | — | — |
| Comp. Example 21 | — | — | MN | 92 | Bis-A-1 | 5 | TU | 4 | — | — |
| Comp. Example 22 | — | — | MN | 91 | Hydrogenated Bis-A | 5 | TU | 4 | — | — |
| Comp. Example 23 | — | — | MN | 86 | Bis-A-2 | 11 | TU | 3 | — | — |
| Comp. Example 24 | — | — | MN | 84 | Bis-A-3 | 12 | TU | 3 | — | — |
| Comp. Example 25 | — | — | MN | 83 | Bis-A-4 | 14 | TU | 3 | — | — |
| Comp. Example 26 | — | — | MN | 55 | PGE | 22 | TCA | 23 | — | — |
| Comp. Example 27 | — | — | SW | 88 | PGE | 5 | TCA | 7 | — | — |
| Comp. Example 28 | — | — | MN | 65 | PGE | 17 | TCK | 18 | — | — |
| Comp. Example 29 | — | — | MN | 66 | PGE | 16 | TCN | 18 | — | — |
| Comp. Example 30 | — | — | MN | 94 | C50 | 2 | TU | 4 | — | — |
| Comp. Example 31 | — | — | MN | 94 | C60 | 2 | TU | 4 | — | — |
| Comp. Example 32 | — | — | MN | 94 | C70 | 3 | TU | 4 | — | — |
| Comp. Example 33 | — | — | MN | 93 | C80 | 3 | TU | 4 | — | — |
| Comp. Example 34 | — | — | MN | 93 | CEL | 3 | TU | 4 | — | — |
| Comp. Example 35 | — | — | MN | 94 | BEDS | 2 | TU | 4 | — | — |
| Comp. Example 36 | — | — | MN | 92 | BGTD | 4 | TU | 4 | — | — |
| Comp. Example 37 | — | — | MN | 92 | BCTD | 5 | TU | 4 | — | — |
| Comp. Example 38 | — | — | MN | 92 | TGCS | 4 | TU | 4 | — | — |
| Comp. Example 39 | — | — | MN | 92 | TCCS | 4 | TU | 4 | — | — |
| Comp. Example 40 | — | — | MN | 94 | BDMO | 2 | TU | 4 | — | — |
| Comp. Example 41 | — | — | MN | 94 | EPHE | 2 | TU | 4 | — | — |
| Comp. Example 42 | — | — | MN | 93 | AGE | 3 | TU | 4 | — | — |
| Comp. Example 43 | — | — | MN | 93 | EVCH | 3 | TU | 4 | — | — |
| Comp. Example 44 | — | — | MN | 93 | GLMT | 3 | TU | 4 | — | — |

TABLE 4

<Decision> AA: particularly satisfactory, A: satisfactory, C: poor,
<Overall decision> AA, A: acceptable, c: unacceptable

| | HV (mg/g) | WPE (g/eq) | α | β | ε | Reaction temperature (° C.) | Epoxy group reaction rate (%) | Episulfide group yield (%) | Decision | Reaction time HR | Decision | Overall decision |
|---|---|---|---|---|---|---|---|---|---|---|---|---|
| Example 1 | 1808 | 150 | 2 | 0.29 | — | 20 | 100 | 86 | A | 4 | AA | A |
| Example 2 | 1475 | 150 | 2 | 0.29 | — | 20 | 100 | 93 | AA | 2 | AA | AA |
| Example 3 | 1475 | 150 | 2 | 0.29 | — | 20 | 100 | 91 | AA | 4 | AA | AA |
| Example 4 | 1245 | 150 | 2 | 0.28 | — | 20 | 100 | 95 | AA | 2 | AA | AA |
| Example 5 | 1245 | 150 | 2 | 0.24 | — | 20 | 100 | 92 | AA | 4 | AA | AA |
| Example 6 | 1245 | 150 | 2 | 0.26 | — | 20 | 100 | 95 | AA | 2 | AA | AA |
| Example 7 | 1078 | 150 | 2 | 0.20 | — | 20 | 100 | 92 | AA | 2 | AA | AA |
| Example 8 | 950 | 150 | 2 | 0.12 | — | 20 | 100 | 93 | AA | 2 | AA | AA |
| Example 9 | 767 | 150 | 2 | 0.08 | — | 20 | 100 | 92 | AA | 3 | AA | AA |
| Example 10 | 1828 | 150 | 2 | 0.12 | — | 20 | 100 | 80 | A | 20 | A | A |
| Example 11 | 1057 | 150 | 2 | 0.2 | — | 20 | 100 | 89 | A | 7 | A | A |
| Example 12 | 747 | 150 | 2 | 0.17 | — | 20 | 100 | 85 | A | 12 | A | A |
| Example 13 | 578 | 150 | 2 | 0.17 | — | 20 | 100 | 83 | A | 12 | A | A |
| Example 14 | 471 | 150 | 2 | 0.15 | — | 20 | 100 | 83 | A | 15 | A | A |
| Example 15 | 397 | 150 | 2 | 0.13 | — | 20 | 100 | 82 | A | 19 | A | A |
| Example 16 | 303 | 150 | 2 | 0.11 | 0.55 | 20 | 100 | 82 | A | 20 | A | A |
| Example 17 | 205 | 150 | 2 | 0.1 | 0.50 | 20 | 100 | 80 | A | 23 | A | A |
| Example 18 | 561 | 150 | 2 | 0.17 | — | 20 | 100 | 86 | A | 8 | A | A |
| Example 19 | 374 | 150 | 2 | 0.16 | — | 20 | 100 | 83 | A | 13 | A | A |
| Example 20 | 281 | 150 | 2 | 0.15 | — | 20 | 100 | 81 | A | 15 | A | A |
| Example 21 | 1245 | 150 | 4 | 0.13 | — | 20 | 100 | 92 | AA | 2 | AA | AA |
| Example 22 | 1245 | 150 | 6 | 0.28 | — | 20 | 100 | 86 | A | 1 | AA | A |
| Example 23 | 1245 | 150 | 10 | 0.12 | — | 20 | 100 | 80 | A | 1 | AA | A |
| Example 24 | 1245 | 150 | 1.5 | 0.28 | — | 20 | 100 | 95 | AA | 3 | AA | AA |
| Example 25 | 1245 | 150 | 1.2 | 0.22 | — | 20 | 100 | 89 | A | 8 | A | A |
| Example 26 | 1245 | 150 | 1 | 0.28 | — | 20 | 100 | 88 | A | 17 | A | A |
| Example 27 | 1475 | 150 | 2 | 0.01 | — | 20 | 100 | 97 | AA | 15 | A | A |
| Example 28 | 1475 | 150 | 2 | 0.015 | — | 20 | 100 | 96 | AA | 12 | A | A |
| Example 29 | 1475 | 150 | 2 | 0.02 | — | 20 | 100 | 96 | AA | 3 | AA | AA |
| Example 30 | 1475 | 150 | 2 | 0.5 | — | 20 | 100 | 87 | A | 2 | AA | A |
| Example 31 | 1475 | 150 | 2 | 0.45 | — | 20 | 100 | 90 | A | 2 | AA | A |
| Example 32 | 1475 | 150 | 2 | 0.42 | — | 20 | 100 | 90 | AA | 2 | AA | AA |
| Example 33 | 1245 | 150 | 2 | 0.28 | — | 10 | 100 | 95 | AA | 3 | AA | AA |
| Example 34 | 1245 | 150 | 2 | 0.28 | — | 5 | 100 | 96 | AA | 8 | A | A |
| Example 35 | 1245 | 150 | 2 | 0.28 | — | 0 | 100 | 97 | AA | 15 | A | A |
| Example 36 | 1245 | 150 | 2 | 0.28 | — | 60 | 100 | 92 | AA | 1 | AA | AA |
| Example 37 | 1245 | 150 | 2 | 0.28 | — | 80 | 100 | 87 | A | 1 | AA | A |
| Example 38 | 1245 | 150 | 2 | 0.28 | — | 100 | 100 | 83 | A | 1 | AA | A |
| Example 39 | 1078 | 44 | 2 | 0.1 | — | 0 | 100 | 83 | A | 6 | AA | A |
| Example 40 | 1245 | 58 | 2 | 0.28 | — | 20 | 100 | 87 | A | 6 | AA | A |
| Example 41 | 1475 | 72 | 2 | 0.25 | — | 20 | 100 | 87 | A | 2 | AA | A |
| Example 42 | 1245 | 86 | 2 | 0.28 | — | 20 | 100 | 86 | A | 3 | AA | A |
| Example 43 | 1475 | 100 | 2 | 0.29 | — | 20 | 100 | 92 | AA | 3 | AA | AA |

TABLE 5

<Decision> AA: particularly satisfactory, A: satisfactory, C: poor,
<Overall decision> AA, A: acceptable, C: unacceptable

| | HV (mg/g) | WPE (g/eq) | α | β | ε | Reaction temperature (° C.) | Epoxy group reaction rate (%) | Episulfide group yield (%) | Decision | Reaction time HR | Decision | Overall decision |
|---|---|---|---|---|---|---|---|---|---|---|---|---|
| Example 44 | 1245 | 114 | 2 | 0.28 | — | 20 | 100 | 91 | AA | 2 | AA | AA |
| Example 45 | 1245 | 128 | 2 | 0.28 | — | 20 | 100 | 94 | AA | 1 | AA | AA |
| Example 46 | 1245 | 156 | 2 | 0.28 | — | 20 | 100 | 92 | AA | 3 | AA | AA |
| Example 47 | 1245 | 184 | 2 | 0.28 | — | 20 | 100 | 95 | AA | 2 | AA | AA |
| Example 48 | 1245 | 212 | 2 | 0.28 | — | 20 | 100 | 91 | AA | 2 | AA | AA |
| Example 49 | 1245 | 240 | 2 | 0.28 | — | 20 | 100 | 94 | AA | 4 | AA | AA |
| Example 50 | 1245 | 268 | 2 | 0.28 | — | 20 | 100 | 94 | AA | 2 | AA | AA |
| Example 51 | 1245 | 297 | 2 | 0.28 | — | 20 | 100 | 93 | AA | 3 | AA | AA |
| Example 52 | 1245 | 189 | 2 | 0.21 | — | 20 | 100 | 94 | AA | 2 | AA | AA |
| Example 53 | 1245 | 205 | 2 | 0.21 | — | 20 | 100 | 94 | AA | 4 | AA | AA |
| Example 54 | 1245 | 480 | 2 | 0.08 | — | 60 | 100 | 90 | AA | 6 | AA | AA |
| Example 55 | 1245 | 560 | 2 | 0.05 | — | 80 | 100 | 88 | A | 5 | AA | A |

TABLE 5-continued

<Decision> AA: particularly satisfactory, A: satisfactory, C: poor,
<Overall decision> AA, A: acceptable, C: unacceptable

| | HV (mg/g) | WPE (g/eq) | α | β | ε | Reaction temperature (°C.) | Epoxy group reaction rate (%) | Episulfide group yield (%) | Decision | Reaction time HR | Decision | Overall decision |
|---|---|---|---|---|---|---|---|---|---|---|---|---|
| Example 56 | 1245 | 650 | 2 | 0.04 | — | 80 | 100 | 83 | A | 6 | AA | A |
| Example 57 | 1245 | 150 | 2 | 0.28 | — | 20 | 100 | 87 | A | 4 | AA | A |
| Example 58 | 1245 | 150 | 2 | 0.28 | — | 20 | 100 | 88 | A | 4 | AA | A |
| Example 59 | 1245 | 150 | 2 | 0.41 | — | 20 | 100 | 87 | A | 2 | AA | A |
| Example 60 | 1245 | 150 | 2 | 0.28 | 2.8 | 20 | 100 | 94 | AA | 6 | AA | AA |
| Example 61 | 1245 | 150 | 2 | 0.28 | — | 20 | 100 | 90 | AA | 5 | AA | AA |
| Example 62 | 1245 | 150 | 2 | 0.28 | — | 20 | 100 | 91 | AA | 5 | AA | AA |
| Example 63 | 1245 | 150 | 2 | 0.28 | — | 20 | 100 | 90 | AA | 5 | AA | AA |
| Example 64 | 1245 | 150 | 2 | 0.28 | 2.8 | 20 | 100 | 92 | AA | 4 | AA | AA |
| Example 65 | 1245 | 84 | 2 | 0.28 | — | 20 | 100 | 83 | A | 12 | A | A |
| Example 66 | 1245 | 98 | 2 | 0.28 | — | 20 | 100 | 91 | AA | 8 | A | A |
| Example 67 | 1245 | 112 | 2 | 0.28 | — | 20 | 100 | 81 | A | 18 | A | A |
| Example 68 | 1245 | 126 | 2 | 0.28 | — | 20 | 100 | 84 | A | 22 | A | A |
| Example 69 | 1245 | 131 | 2 | 0.28 | — | 20 | 100 | 93 | AA | 15 | A | A |
| Example 70 | 1245 | 91 | 2 | 0.28 | — | 20 | 100 | 94 | AA | 2 | AA | AA |
| Example 71 | 1245 | 181 | 2 | 0.28 | — | 20 | 100 | 96 | AA | 1 | AA | AA |
| Example 72 | 1245 | 191 | 2 | 0.28 | — | 20 | 100 | 90 | AA | 15 | A | A |
| Example 73 | 1245 | 174 | 2 | 0.28 | — | 20 | 100 | 95 | AA | 1 | AA | AA |
| Example 74 | 1245 | 184 | 2 | 0.28 | — | 20 | 100 | 90 | AA | 18 | A | A |
| Example 75 | 1245 | 70 | 2 | 0.28 | — | 20 | 100 | 83 | A | 4 | AA | A |
| Example 76 | 1245 | 98 | 2 | 0.28 | — | 20 | 100 | 92 | AA | 2 | AA | AA |
| Example 77 | 1245 | 114 | 2 | 0.28 | — | 20 | 100 | 94 | AA | 1 | AA | AA |
| Example 78 | 1245 | 124 | 2 | 0.28 | — | 20 | 100 | 91 | AA | 20 | A | A |
| Example 79 | 1245 | 142 | 2 | 0.28 | — | 20 | 100 | 92 | AA | 2 | AA | AA |
| Example 80 | 1838 | 150 | 2 | 0.38 | 0.08 | 20 | 100 | 88 | A | 9 | A | A |
| Example 81 | 1844 | 150 | 2 | 0.4 | 0.08 | 20 | 100 | 85 | A | 12 | A | A |
| Example 82 | 1848 | 150 | 2 | 0.38 | 0.08 | 20 | 100 | 85 | A | 12 | A | A |
| Example 83 | 1851 | 150 | 2 | 0.42 | 0.06 | 20 | 100 | 82 | A | 16 | A | A |
| Example 84 | 1557 | 150 | 2 | 0.4 | 0.07 | 20 | 100 | 82 | A | 20 | A | A |
| Example 85 | 1311 | 150 | 2 | 0.42 | 0.07 | 20 | 100 | 80 | A | 23 | A | A |
| Example 86 | 2336 | 150 | 2 | 0.5 | — | 20 | 100 | 81 | A | 22 | A | A |

TABLE 6

<Decision> AA: particularly satisfactory, A: satisfactory, C: poor,
<Overall decision> AA, A: acceptable, C: unacceptable

| | WPE (g/eq) | α | β | ε | Reaction temperature (°C.) | Epoxy group reaction rate (%) | Episulfide group yield (%) | Decision | Reaction time HR | Decision | Overall decision |
|---|---|---|---|---|---|---|---|---|---|---|---|
| Comp. Example 1 | 150 | 2 | — | 0.04 | 20 | 100 | 72 | C | 32 | C | C |
| Comp. Example 2 | 150 | 1 | — | 0.04 | 20 | 100 | 69 | C | 150 | C | C |
| Comp. Example 3 | 150 | 10 | — | 0.04 | 20 | 100 | 60 | C | 4 | AA | C |
| Comp. Example 4 | 150 | 2 | — | 0.01 | 20 | 100 | 74 | C | 130 | C | C |
| Comp. Example 5 | 150 | 2 | — | 0.4 | 20 | 100 | 53 | C | 4 | AA | C |
| Comp. Example 6 | 150 | 2 | — | 0.04 | 0 | 100 | 76 | C | 400 | C | C |
| Comp. Example 7 | 150 | 2 | — | 0.04 | 100 | 100 | 58 | C | 8 | A | C |
| Comp. Example 8 | 44 | 2 | — | 0.04 | 20 | 100 | 62 | C | 25 | C | C |
| Comp. Example 9 | 58 | 2 | — | 0.04 | 20 | 100 | 55 | C | 30 | C | C |
| Comp. Example 10 | 72 | 2 | — | 0.04 | 20 | 100 | 50 | C | 28 | C | C |
| Comp. Example 11 | 86 | 2 | — | 0.04 | 20 | 100 | 57 | C | 33 | C | C |
| Comp. Example 12 | 100 | 2 | — | 0.04 | 20 | 100 | 60 | C | 40 | C | C |
| Comp. Example 13 | 114 | 2 | — | 0.04 | 20 | 100 | 54 | C | 28 | C | C |
| Comp. Example 14 | 128 | 2 | — | 0.04 | 20 | 100 | 54 | C | 30 | C | C |
| Comp. Example 15 | 156 | 2 | — | 0.04 | 20 | 100 | 58 | C | 32 | C | C |
| Comp. Example 16 | 184 | 2 | — | 0.04 | 20 | 100 | 52 | C | 29 | C | C |
| Comp. Example 17 | 212 | 2 | — | 0.04 | 20 | 100 | 55 | C | 34 | C | C |
| Comp. Example 18 | 240 | 2 | — | 0.04 | 20 | 100 | 57 | C | 40 | C | C |
| Comp. Example 19 | 268 | 2 | — | 0.04 | 20 | 100 | 49 | C | 26 | C | C |
| Comp. Example 20 | 297 | 2 | — | 0.04 | 20 | 100 | 50 | C | 28 | C | C |
| Comp. Example 21 | 189 | 2 | — | 0.04 | 20 | 100 | 60 | C | 55 | C | C |
| Comp. Example 22 | 205 | 2 | — | 0.04 | 20 | 100 | 62 | C | 60 | C | C |
| Comp. Example 23 | 480 | 2 | — | 0.04 | 60 | 100 | 60 | C | 17 | A | C |
| Comp. Example 24 | 560 | 2 | — | 0.04 | 80 | 100 | 53 | C | 12 | A | C |

TABLE 6-continued

<Decision> AA: particularly satisfactory, A: satisfactory, C: poor,
<Overall decision> AA, A: acceptable, C: unacceptable

| | WPE (g/eq) | α | β | ε | Reaction temperature (°C.) | Epoxy group reaction rate (%) | Episulfide group yield (%) | Decision | Reaction time HR | Decision | Overall decision |
|---|---|---|---|---|---|---|---|---|---|---|---|
| Comp. Example 25 | 650 | 2 | — | 0.04 | 80 | 100 | 66 | C | 8 | A | C |
| Comp. Example 26 | 150 | 2 | — | 0.41 | 20 | 100 | 62 | C | 15 | A | C |
| Comp. Example 27 | 150 | 2 | — | 0.08 | 20 | 100 | 66 | C | 100 | C | C |
| Comp. Example 28 | 150 | 2 | — | 0.27 | 20 | 100 | 60 | C | 30 | C | C |
| Comp. Example 29 | 150 | 2 | — | 0.27 | 20 | 100 | 55 | C | 35 | C | C |
| Comp. Example 30 | 84 | 2 | — | 0.04 | 20 | 100 | 50 | C | 60 | C | C |
| Comp. Example 31 | 98 | 2 | — | 0.04 | 20 | 100 | 58 | C | 48 | C | C |
| Comp. Example 32 | 112 | 2 | — | 0.04 | 20 | 100 | 52 | C | 90 | C | C |
| Comp. Example 33 | 126 | 2 | — | 0.04 | 20 | 100 | 55 | C | 84 | C | C |
| Comp. Example 34 | 131 | 2 | — | 0.04 | 20 | 100 | 60 | C | 76 | C | C |
| Comp. Example 35 | 91 | 2 | — | 0.04 | 20 | 100 | 63 | C | 5 | AA | C |
| Comp. Example 36 | 181 | 2 | — | 0.04 | 20 | 100 | 56 | C | 7 | A | C |
| Comp. Example 37 | 191 | 2 | — | 0.04 | 20 | 100 | 48 | C | 50 | C | C |
| Comp. Example 38 | 174 | 2 | — | 0.04 | 20 | 100 | 52 | C | 8 | A | C |
| Comp. Example 39 | 184 | 2 | — | 0.04 | 20 | 100 | 50 | C | 38 | C | C |
| Comp. Example 40 | 70 | 2 | — | 0.04 | 20 | 100 | 52 | C | 10 | A | C |
| Comp. Example 41 | 98 | 2 | — | 0.04 | 20 | 100 | 60 | C | 16 | A | C |
| Comp. Example 42 | 114 | 2 | — | 0.04 | 20 | 100 | 54 | C | 8 | A | C |
| Comp. Example 43 | 124 | 2 | — | 0.04 | 20 | 100 | 44 | C | 60 | C | C |
| Comp. Example 44 | 142 | 2 | — | 0.04 | 20 | 100 | 52 | C | 12 | A | C |

As listed in Tables 1 to 6, it was verified that the method for producing an episulfide compound according to the present exemplary embodiment, which includes a process of thiating epoxy groups of (B) an epoxy compound through a reaction with (C) a thiating agent in the presence of (A) a polyhydric hydroxyl compound having two or more hydroxyl groups, is an excellent method that takes a short reaction time, gives a high episulfide group yield, and imposes less environmental load since a metal catalyst and the like are not used. On the contrary, according to the Comparative Examples in which a reaction was carried out in the presence of an alcohol having one hydroxyl group or water, the yield of the episulfide group was not sufficient, and the reaction time was also long in many cases.

Example 87

A reaction product containing an episulfide compound was separated from the reaction liquid obtained after completion of the reaction of Example 1, by the following procedure.

(1) NHX (non-polar solvent) and SW (hydroxyl compound) were added to the reaction liquid, and the mixture was mixed and stirred. Subsequently, stirring was stopped, and the mixture was left to stand still until separation of an NHX layer containing the episulfide compound and an SW layer occurred.

(2) Only the NHX layer was collected.

(3) Saturated brine was added to the NHX layer obtained in step (2), and the mixture was mixed and stirred. Subsequently, stirring was stopped, and the mixture was left to stand still until separation of an NHX layer and a saturated brine layer occurred. Only the NHX layer was collected.

(4) Anhydrous magnesium sulfate (manufactured by Wako Pure Chemical Industries, Ltd.) was added to the NHX layer obtained in step (3), and the mixture was mixed and stirred. Anhydrous magnesium sulfate was removed by filtration, and an NHX layer was obtained.

(5) Low boiling point compounds (including NHX) that were contained in the NHX layer obtained in step (4) were distilled off using a rotary evaporator, and a reaction product containing the episulfide compound was obtained.

Meanwhile, the operations of the steps (3) and (4) are operations that were carried out in order to shorten the time taken until water was distilled off, when the low boiling point compounds (including NHX) that were contained in the NHX layer obtained in step (2) were distilled off using a rotary evaporator. If the relevant operations are not necessary, the operations of steps (3) and (4) may not be performed.

(6) The episulfide compound content in the reaction product thus obtained was measured according to the method described above. Storage stability of the reaction product was evaluated by the method described above, and as a result, the degeneration ratio was found to be 18%, which was considered satisfactory.

Examples 88 to 146

A reaction product containing an episulfide compound was separated by the same method as that used in Example 87, except that each of the reaction liquids obtained in Examples 2 to 86 was used. The results of evaluating the storage stability of the reaction products thus obtained are presented in Table 7.

A reaction product containing an episulfide compound was separated by the same method as that used in Example 87, except that each of the reaction liquids obtained in Examples 2 to 86, and the non-polar solvent indicated in Table 7 were used. The results of evaluating the storage stability of the reaction products thus obtained are presented in Table 7.

Comparative Examples 45 to 78

A reaction product containing an episulfide compound was separated by the same method as that used in Example 87, except that each of the reaction liquids obtained in Comparative Examples 1 to 44 was used. The results of evaluating the storage stability of the reaction products thus obtained are presented in Table 8.

A reaction product containing an episulfide compound was separated by the same method as that used in Example 87, except that each of the reaction liquids obtained in Examples 1 to 44, and the non-polar solvent indicated in Table 8 were used. The results of evaluating the storage stability of the reaction products thus obtained are presented in Table 8.

TABLE 7

<Decision> AA: particularly satisfactory, A: satisfactory, C: poor

|  | Non-polar solvent | Episulfide compound content Before retention (%) | Episulfide compound content After one-year retention (%) | Degeneration ratio % | Storage stability Decision |
|---|---|---|---|---|---|
| Example 87 | HNX | 88 | 78 | 11 | A |
| Example 88 | HNX | 93 | 86 | 8 | AA |
| Example 89 | HNX | 92 | 86 | 7 | AA |
| Example 90 | HNX | 96 | 92 | 4 | AA |
| Example 91 | HNX | 94 | 89 | 5 | AA |
| Example 92 | HNX | 96 | 91 | 5 | AA |
| Example 93 | HNX | 93 | 86 | 7 | AA |
| Example 94 | HNX | 94 | 87 | 7 | AA |
| Example 95 | HNX | 93 | 83 | 11 | A |
| Example 96 | HNX | 82 | 67 | 18 | A |
| Example 97 | HNX | 89 | 79 | 11 | A |
| Example 98 | HNX | 85 | 74 | 13 | A |
| Example 99 | HNX | 85 | 74 | 13 | A |
| Example 100 | HNX | 83 | 69 | 17 | A |
| Example 101 | HNX | 84 | 71 | 16 | A |
| Example 102 | HNX | 85 | 70 | 18 | A |
| Example 103 | HNX | 83 | 67 | 19 | A |
| Example 104 | HNX | 88 | 77 | 12 | A |
| Example 105 | HNX | 85 | 72 | 15 | A |
| Example 106 | HNX | 81 | 67 | 18 | A |
| Example 107 | DEE | 85 | 69 | 19 | A |
| Example 108 | DEE | 89 | 74 | 17 | A |
| Example 109 | HNX | 87 | 75 | 14 | A |
| Example 110 | HNX | 87 | 77 | 12 | A |
| Example 111 | HNX | 93 | 87 | 6 | AA |
| Example 112 | HNX | 93 | 86 | 7 | AA |
| Example 113 | HNX | 94 | 89 | 5 | AA |
| Example 114 | HNX | 94 | 88 | 6 | AA |
| Example 115 | HNX | 95 | 91 | 4 | AA |
| Example 116 | HNX | 92 | 87 | 5 | AA |
| Example 117 | HNX | 94 | 88 | 6 | AA |
| Example 118 | HNX | 95 | 91 | 4 | AA |
| Example 119 | HNX | 94 | 87 | 7 | AA |
| Example 120 | ACET | 94 | 91 | 4 | AA |
| Example 121 | ACET | 95 | 89 | 6 | AA |
| Example 122 | ACET | 92 | 87 | 5 | AA |
| Example 123 | ACET | 89 | 78 | 12 | A |
| Example 124 | ACET | 83 | 71 | 15 | A |
| Example 125 | HNX | 95 | 78 | 18 | A |
| Example 126 | HNX | 92 | 75 | 18 | A |
| Example 127 | HNX | 83 | 70 | 16 | A |
| Example 128 | HNX | 85 | 72 | 15 | A |
| Example 129 | ACET | 93 | 77 | 17 | A |
| Example 130 | ACET | 94 | 89 | 5 | AA |
| Example 131 | HNX | 96 | 90 | 6 | AA |
| Example 132 | HNX | 92 | 80 | 13 | A |
| Example 133 | HNX | 96 | 91 | 5 | AA |
| Example 134 | HNX | 92 | 79 | 14 | A |
| Example 135 | HNX | 84 | 70 | 17 | A |
| Example 136 | HNX | 93 | 86 | 7 | AA |
| Example 137 | HNX | 95 | 90 | 5 | AA |
| Example 138 | HNX | 92 | 76 | 17 | A |
| Example 139 | HNX | 92 | 85 | 8 | AA |
| Example 140 | HNX | 88 | 77 | 12 | A |
| Example 141 | HNX | 86 | 76 | 12 | A |
| Example 142 | HNX | 87 | 74 | 15 | A |
| Example 143 | HNX | 85 | 71 | 16 | A |
| Example 144 | HNX | 85 | 70 | 18 | A |
| Example 145 | HNX | 83 | 67 | 19 | A |
| Example 146 | HNX | 83 | 68 | 18 | A |

TABLE 8

<Decision> AA: particularly satisfactory, A: satisfactory, C: poor

|  | Non-polar solvent | Episulfide compound content Before retention (%) | Episulfide compound content After one-year retention (%) | Degeneration ratio (%) | Storage stability Decision |
|---|---|---|---|---|---|
| Comp. Example 45 | HNX | 74 | 36 | 52 | C |
| Comp. Example 46 | DEE | 65 | 26 | 60 | C |
| Comp. Example 47 | DEE | 56 | 21 | 62 | C |
| Comp. Example 48 | HNX | 55 | 28 | 50 | C |
| Comp. Example 49 | HNX | 57 | 30 | 48 | C |
| Comp. Example 50 | HNX | 62 | 28 | 55 | C |
| Comp. Example 51 | HNX | 56 | 25 | 56 | C |
| Comp. Example 52 | HNX | 56 | 26 | 54 | C |
| Comp. Example 53 | HNX | 60 | 29 | 52 | C |
| Comp. Example 54 | HNX | 55 | 23 | 58 | C |
| Comp. Example 55 | HNX | 56 | 29 | 48 | C |
| Comp. Example 56 | HNX | 57 | 25 | 56 | C |
| Comp. Example 57 | HNX | 51 | 24 | 52 | C |
| Comp. Example 58 | HNX | 55 | 26 | 52 | C |
| Comp. Example 59 | ACET | 63 | 20 | 68 | C |
| Comp. Example 60 | ACET | 64 | 22 | 66 | C |
| Comp. Example 61 | ACET | 62 | 19 | 70 | C |
| Comp. Example 62 | ACET | 55 | 20 | 64 | C |
| Comp. Example 63 | ACET | 66 | 22 | 66 | C |
| Comp. Example 64 | HNX | 53 | 15 | 72 | C |
| Comp. Example 65 | HNX | 58 | 17 | 70 | C |
| Comp. Example 66 | HNX | 55 | 19 | 65 | C |
| Comp. Example 67 | HNX | 60 | 19 | 68 | C |
| Comp. Example 68 | HNX | 62 | 21 | 66 | C |
| Comp. Example 69 | HNX | 63 | 30 | 52 | C |
| Comp. Example 70 | HNX | 58 | 30 | 48 | C |
| Comp. Example 71 | HNX | 52 | 20 | 62 | C |
| Comp. Example 72 | HNX | 52 | 26 | 50 | C |
| Comp. Example 73 | HNX | 54 | 17 | 68 | C |
| Comp. Example 74 | HNX | 54 | 18 | 66 | C |
| Comp. Example 75 | HNX | 64 | 18 | 72 | C |
| Comp. Example 76 | HNX | 56 | 24 | 58 | C |
| Comp. Example 77 | HNX | 48 | 24 | 50 | C |
| Comp. Example 78 | HNX | 56 | 18 | 68 | C |

Example 148

A reaction product containing an episulfide compound was separated by distilling the reaction liquid obtained after completion of the reaction of Example 39 by making reference to the methods illustrated in Shin Jikken Kagaku Kouza (New Lectures on Experimental Science) (Maruzen Co., Ltd.) and Kagaku Jikken Manyuaru (Manual for Chemical Experiments) (Gihodo Shuppan Co., Ltd.).

Regarding the conditions for the distillation operation, the pressure may be normal pressure, a reduced pressure, or an increased pressure, and a temperature which exceeds the boiling point of the episulfide compound under the given pressure conditions may be employed. For example, in the present Example, conditions of 60° C. at normal pressure, and conditions of 20° C. at 20 kPa may be used. In order to increase the yield of the reaction product obtainable after distillation, it is preferable to perform the distillation at a low temperature. The episulfide compound content in the reaction product thus obtained was measured, and the content was found to be 99%.

Example 149

A reaction product containing an episulfide compound was separated by the same method as that used in Example 148, except that the reaction liquid obtained after completion of the reaction of Example 40 was used. The episulfide compound content in the reaction product thus obtained was measured, and the content was found to be 99%.

Example 150

A reaction product containing an episulfide compound was separated by the same method as that used in Example 148, except that the reaction liquid obtained after completion of the reaction of Example 41 was used. The episulfide compound content in the reaction product thus obtained was measured, and the content was found to be 99%.

Example 151

A reaction product containing an episulfide compound was separated by the same method as that used in Example 148, except that the reaction product obtained after the separation operation of Example 87 was used. The episulfide compound content in the reaction product thus obtained was measured, and the content was found to be 99%.

Example 152

A reaction product containing an episulfide compound was separated by the same method as that used in Example 148, except that the reaction product obtained after the separation operation of Example 107 was used. The episulfide compound content in the reaction product thus obtained was measured, and the content was found to be 99%.

Example 153

A reaction product containing an episulfide compound was separated by the same method as that used in Example 148, except that the reaction product obtained after the separation operation of Example 108 was used. The episulfide compound content in the reaction product thus obtained was measured, and the content was found to be 99%.

Example 154

A reaction product containing an episulfide compound was separated by the same method as that used in Example 148, except that the reaction product obtained after the separation operation of Example 109 was used. The episulfide compound content in the reaction product thus obtained was measured, and the content was found to be 99%.

Example 155

A reaction product containing an episulfide compound was separated by the same method as that used in Example 148, except that the reaction product obtained after the separation operation of Example 110 was used. The episulfide compound content in the reaction product thus obtained was measured, and the content was found to be 99%.

Example 156

A reaction product containing an episulfide compound was separated by the same method as that used in Example 148, except that the reaction product obtained after the separation operation of Example 111 was used. The episulfide compound content in the reaction product thus obtained was measured, and the content was found to be 99%.

Example 157

A reaction product containing an episulfide compound was separated by the same method as that used in Example 148, except that the reaction product obtained after the separation operation of Example 112 was used. The episulfide compound content in the reaction product thus obtained was measured, and the content was found to be 99%.

Example 158

A reaction product containing an episulfide compound was separated by the same method as that used in Example 148, except that the reaction product obtained after the separation operation of Example 113 was used. The episulfide compound content in the reaction product thus obtained was measured, and the content was found to be 99%.

Example 159

A reaction product containing an episulfide compound was separated by the same method as that used in Example 148, except that the reaction product obtained after the separation operation of Example 125 was used. The episulfide compound content in the reaction product thus obtained was measured, and the content was found to be 99%.

Example 160

A reaction product containing an episulfide compound was separated by the same method as that used in Example 148, except that the reaction product obtained after the separation operation of Example 126 was used. The episulfide compound content in the reaction product thus obtained was measured, and the content was found to be 99%.

Example 161

A reaction product containing an episulfide compound was separated by the same method as that used in Example 148, except that the reaction product obtained after the separation operation of Example 127 was used. The episulfide compound content in the reaction product thus obtained was measured, and the content was found to be 99%.

Example 162

A reaction product containing an episulfide compound was separated by the same method as that used in Example 148, except that the reaction product obtained after the separation operation of Example 128 was used. The episulfide compound content in the reaction product thus obtained was measured, and the content was found to be 99%.

Example 163

A reaction product containing an episulfide compound was separated by the same method as that used in Example 148, except that the reaction product obtained after the separation operation of Example 135 was used. The episulfide compound content in the reaction product thus obtained was measured, and the content was found to be 99%.

Example 164

A reaction product containing an episulfide compound was separated by the same method as that used in Example 148, except that the reaction product obtained after the separation operation of Example 136 was used. The episulfide compound content in the reaction product thus obtained was measured, and the content was found to be 99%.

Example 165

A reaction product containing an episulfide compound was separated by the same method as that used in Example 148, except that the reaction product obtained after the separation operation of Example 137 was used. The episulfide compound content in the reaction product thus obtained was measured, and the content was found to be 99%.

Example 166

A reaction product containing an episulfide compound was separated by the same method as that used in Example 148, except that the reaction product obtained after the separation operation of Example 138 was used. The episulfide compound content in the reaction product thus obtained was measured, and the content was found to be 99%.

Example 167

A reaction product containing an episulfide compound was separated by the same method as that used in Example 148, except that the reaction product obtained after the separation operation of Example 139 was used. The episulfide compound content in the reaction product thus obtained was measured, and the content was found to be 99%.

Example 168

A reaction product containing an episulfide compound was purified by separating the reaction liquid obtained after completion of the reaction of Example 1 by column chromatography by making reference to the methods illustrated in Shin Jikken Kagaku Kouza (New Lectures on Experimental Science) (Maruzen Co., Ltd.) and Kagaku Jikken Manyuaru (Manual for Chemical Experiments) (Gihodo Shuppan Co., Ltd.), and distilling off the eluent used therein.

Meanwhile, regarding the conditions for column chromatography, the packing agent and the eluent may be selected in accordance with the properties of the episulfide compound. For example, in the present Example, conditions of using silica gel 60N (spherical, neutral) (manufactured by Kanto Chemical Co., Ltd.) or activated alumina (manufactured by Wako Pure Chemical Industries, Ltd.) as the packing agent, and using a mixed solvent of n-hexane with a gradually increasing content of ethyl acetate as the eluent, may be used.

The episulfide compound content in the reaction product obtained after purification was measured, and the content was found to be 99%.

Example 169

A reaction product containing an episulfide compound was purified by the same method as that used in Example 168, except that the reaction product obtained after the separation operation of Example 111 was used. The episulfide compound content in the reaction product obtained after purification was measured, and the content was found to be 99%.

Example 170

A reaction product containing an episulfide compound was purified by the same method as that used in Example 168, except that the reaction product liquid obtained after the separation operation of Example 112 was used. The episulfide compound content in the reaction product obtained after purification was measured, and the content was found to be 99%.

Example 171

A reaction product containing an episulfide compound was purified by the same method as that used in Example 168, except that the reaction product obtained after the separation operation of Example 113 was used. The episulfide compound content in the reaction product obtained after purification was measured, and the content was found to be 99%.

Example 172

A reaction product containing an episulfide compound was purified by the same method as that used in Example 168, except that the reaction product obtained after the separation operation of Example 114 was used. The episulfide compound content in the reaction product obtained after purification was measured, and the content was found to be 99%.

Example 173

A reaction product containing an episulfide compound was purified by the same method as that used in Example 168, except that the reaction product obtained after the separation operation of Example 115 was used. The episulfide compound content in the reaction product obtained after purification was measured, and the content was found to be 99%.

Example 174

A reaction product containing an episulfide compound was purified by the same method as that used in Example 168, except that the reaction product obtained after the separation operation of Example 116 was used. The episulfide compound content in the reaction product obtained after purification was measured, and the content was found to be 99%.

Example 175

A reaction product containing an episulfide compound was purified by the same method as that used in Example 168, except that the reaction product obtained after the separation operation of Example 117 was used. The episulfide compound content in the reaction product obtained after purification was measured, and the content was found to be 99%.

Example 176

A reaction product containing an episulfide compound was purified by the same method as that used in Example 168, except that the reaction product obtained after the separation operation of Example 118 was used. The episulfide compound content in the reaction product obtained after purification was measured, and the content was found to be 99%.

Example 177

A reaction product containing an episulfide compound was purified by the same method as that used in Example 168, except that the reaction product obtained after the separation operation of Example 119 was used. The episulfide compound content in the reaction product obtained after purification was measured, and the content was found to be 99%.

Example 178

A reaction product containing an episulfide compound was purified by the same method as that used in Example 168, except that the reaction product obtained after the separation operation of Example 120 was used. The episulfide compound content in the reaction product obtained after purification was measured, and the content was found to be 99%.

Example 179

A reaction product containing an episulfide compound was purified by the same method as that used in Example 168, except that the reaction product obtained after the separation operation of Example 121 was used. The episulfide compound content in the reaction product obtained after purification was measured, and the content was found to be 99%.

Example 180

A reaction product containing an episulfide compound was purified by the same method as that used in Example 168, except that the reaction product obtained after the separation operation of Example 122 was used. The episulfide compound content in the reaction product obtained after purification was measured, and the content was found to be 99%.

Example 181

A reaction product containing an episulfide compound was purified by the same method as that used in Example 168, except that the reaction product obtained after the separation operation of Example 123 was used. The episulfide compound content in the reaction product obtained after purification was measured, and the content was found to be 99%.

Example 182

A reaction product containing an episulfide compound was purified by the same method as that used in Example 168, except that the reaction product obtained after the separation operation of Example 124 was used. The episulfide compound content in the reaction product obtained after purification was measured, and the content was found to be 99%.

Example 183

A reaction product containing an episulfide compound was purified by the same method as that used in Example 168, except that the reaction product obtained after the separation operation of Example 126 was used. The episulfide compound content in the reaction product obtained after purification was measured, and the content was found to be 99%.

Example 184

A reaction product containing an episulfide compound was purified by the same method as that used in Example 168, except that the reaction product obtained after the separation operation of Example 127 was used. The episulfide compound content in the reaction product obtained after purification was measured, and the content was found to be 99%.

Example 185

A reaction product containing an episulfide compound was purified by the same method as that used in Example 168, except that the reaction product obtained after the separation operation of Example 128 was used. The episulfide compound content in the reaction product obtained after purification was measured, and the content was found to be 99%.

Example 186

A reaction product containing an episulfide compound was purified by the same method as that used in Example 168, except that the reaction product obtained after the separation operation of Example 129 was used. The episulfide compound content in the reaction product obtained after purification was measured, and the content was found to be 99%.

Example 187

A reaction product containing an episulfide compound was purified by the same method as that used in Example 168, except that the reaction product obtained after the separation operation of Example 130 was used. The episulfide compound content in the reaction product obtained after purification was measured, and the content was found to be 99%.

Example 188

A reaction product containing an episulfide compound was purified by the same method as that used in Example 168, except that the reaction product obtained after the separation operation of Example 131 was used. The episulfide compound content in the reaction product obtained after purification was measured, and the content was found to be 99%.

Example 189

A reaction product containing an episulfide compound was purified by the same method as that used in Example 168, except that the reaction product obtained after the separation operation of Example 132 was used. The episulfide com- Example 190

A reaction product containing an episulfide compound was purified by the same method as that used in Example 168, except that the reaction product obtained after the separation operation of Example 133 was used. The episulfide compound content in the reaction product obtained after purification was measured, and the content was found to be 99%.

Example 191

A reaction product containing an episulfide compound was purified by the same method as that used in Example 168, except that the reaction product obtained after the separation operation of Example 134 was used. The episulfide compound content in the reaction product obtained after purification was measured, and the content was found to be 99%.

Example 192

A reaction product containing an episulfide compound was purified by the same method as that used in Example 168, except that the reaction product obtained after the separation operation of Example 135 was used. The episulfide compound content in the reaction product obtained after purification was measured, and the content was found to be 99%.

Example 193

A reaction product containing an episulfide compound was purified by the same method as that used in Example 168, except that the reaction product obtained after the separation operation of Example 136 was used. The episulfide compound content in the reaction product obtained after purification was measured, and the content was found to be 99%.

Example 194

A reaction product containing an episulfide compound was purified by the same method as that used in Example 168, except that the reaction product obtained after the separation operation of Example 137 was used. The episulfide compound content in the reaction product obtained after purification was measured, and the content was found to be 99%.

Example 195

A reaction product containing an episulfide compound was purified by the same method as that used in Example 168, except that the reaction product obtained after the separation operation of Example 138 was used. The episulfide compound content in the reaction product obtained after purification was measured, and the content was found to be 99%.

Example 196

A reaction product containing an episulfide compound was purified by the same method as that used in Example 168, except that the reaction product obtained after the separation operation of Example 139 was used. The episulfide compound content in the reaction product obtained after purification was measured, and the content was found to be 99%.

Example 197

An episulfide compound was produced by the same method as that used in Example 4, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 198

An episulfide compound was produced by the same method as that used in Example 39, except that the reaction time was changed to 2 hours. Thereafter, a reaction product was separated by the same method as that used in Example 87, and the reaction product thus obtained was separated into an epoxy compound and the episulfide compound by the same method as that used in Example 148.

Example 199

An episulfide compound was produced by the same method as that used in Example 40, except that the reaction time was changed to 2 hours. Thereafter, a reaction product was separated by the same method as that used in Example 87, and the reaction product thus obtained was separated into an epoxy compound and the episulfide compound by the same method as that used in Example 148.

Example 200

An episulfide compound was produced by the same method as that used in Example 41, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 201

An episulfide compound was produced by the same method as that used in Example 42, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 202

An episulfide compound was produced by the same method as that used in Example 43, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 203

An episulfide compound was produced by the same method as that used in Example 44, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 204

An episulfide compound was produced by the same method as that used in Example 45, except that the reaction time was changed to 0.5 hours. Thereafter, a reaction product was separated by the same method as that used in Example 87, and the reaction product thus obtained was separated into an epoxy compound and the episulfide compound by the same method as that used in Example 148.

Example 205

An episulfide compound was produced by the same method as that used in Example 46, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 206

An episulfide compound was produced by the same method as that used in Example 47, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 207

An episulfide compound was produced by the same method as that used in Example 48, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 208

An episulfide compound was produced by the same method as that used in Example 49, except that the reaction time was changed to 2 hours. Thereafter, a reaction product was separated by the same method as that used in Example 87, and the reaction product thus obtained was separated into an epoxy compound and the episulfide compound by the same method as that used in Example 168.

Example 209

An episulfide compound was produced by the same method as that used in Example 50, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 210

An episulfide compound was produced by the same method as that used in Example 51, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 211

An episulfide compound was produced by the same method as that used in Example 52, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 212

An episulfide compound was produced by the same method as that used in Example 53, except that the reaction time was changed to 2 hours. Thereafter, a reaction product was separated by the same method as that used in Example 87, and the reaction product thus obtained was separated into an epoxy compound and the episulfide compound by the same method as that used in Example 168.

Example 213

An episulfide compound was produced by the same method as that used in Example 54, except that the reaction time was changed to 2 hours. Thereafter, a reaction product was separated by the same method as that used in Example 87, and the reaction product thus obtained was separated into an epoxy compound and the episulfide compound by the same method as that used in Example 168.

Example 214

An episulfide compound was produced by the same method as that used in Example 55, except that the reaction time was changed to 2 hours. Thereafter, a reaction product was separated by the same method as that used in Example 87, and the reaction product thus obtained was separated into an epoxy compound and the episulfide compound by the same method as that used in Example 168.

Example 215

An episulfide compound was produced by the same method as that used in Example 56, except that the reaction time was changed to 2 hours. Thereafter, a reaction product was separated by the same method as that used in Example 87, and the reaction product thus obtained was separated into an epoxy compound and the episulfide compound by the same method as that used in Example 168.

Example 216

An episulfide compound was produced by the same method as that used in Example 65, except that the reaction time was changed to 4 hours. Thereafter, a reaction product was separated by the same method as that used in Example 87, and the reaction product thus obtained was separated into an epoxy compound and the episulfide compound by the same method as that used in Example 148.

Example 217

An episulfide compound was produced by the same method as that used in Example 66, except that the reaction time was changed to 3 hours. Thereafter, a reaction product was separated by the same method as that used in Example 87, and the reaction product thus obtained was separated into an epoxy compound and the episulfide compound by the same method as that used in Example 148.

Example 218

An episulfide compound was produced by the same method as that used in Example 67, except that the reaction

Example 219

An episulfide compound was produced by the same method as that used in Example 68, except that the reaction time was changed to 7 hours. Thereafter, a reaction product was separated by the same method as that used in Example 87, and the reaction product thus obtained was separated into an epoxy compound and the episulfide compound by the same method as that used in Example 148.

Example 220

An episulfide compound was produced by the same method as that used in Example 69, except that the reaction time was changed to 5 hours. Thereafter, a reaction product was separated by the same method as that used in Example 87, and the reaction product thus obtained was separated into an epoxy compound and the episulfide compound by the same method as that used in Example 168.

Example 221

An episulfide compound was produced by the same method as that used in Example 70, except that the reaction time was changed to one hour. Thereafter, a reaction product was separated by the same method as that used in Example 87, and the reaction product thus obtained was separated into an epoxy compound and the episulfide compound by the same method as that used in Example 168.

Example 222

An episulfide compound was produced by the same method as that used in Example 71, except that the reaction time was changed to 0.5 hours. Thereafter, a reaction product was separated by the same method as that used in Example 87, and the reaction product thus obtained was separated into an epoxy compound and the episulfide compound by the same method as that used in Example 168.

Example 223

An episulfide compound was produced by the same method as that used in Example 72, except that the reaction time was changed to 5 hours. Thereafter, a reaction product was separated by the same method as that used in Example 87, and the reaction product thus obtained was separated into an epoxy compound and the episulfide compound by the same method as that used in Example 168.

Example 224

An episulfide compound was produced by the same method as that used in Example 73, except that the reaction time was changed to 0.5 hours. Thereafter, a reaction product was separated by the same method as that used in Example 87, and the reaction product thus obtained was separated into an epoxy compound and the episulfide compound by the same method as that used in Example 168.

Example 225

An episulfide compound was produced by the same method as that used in Example 74, except that the reaction time was changed to 6 hours. Thereafter, a reaction product was separated by the same method as that used in Example 87, and the reaction product thus obtained was separated into an epoxy compound and the episulfide compound by the same method as that used in Example 168.

Example 226

An episulfide compound was produced by the same method as that used in Example 75, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 227

An episulfide compound was produced by the same method as that used in Example 76, except that the reaction time was changed to one hour. Thereafter, a reaction product was separated by the same method as that used in Example 87, and the reaction product thus obtained was separated into an epoxy compound and the episulfide compound by the same method as that used in Example 148.

Example 228

An episulfide compound was produced by the same method as that used in Example 77, except that the reaction time was changed to 0.5 hours. Thereafter, a reaction product was separated by the same method as that used in Example 87, and the reaction product thus obtained was separated into an epoxy compound and the episulfide compound by the same method as that used in Example 148.

Example 229

An episulfide compound was produced by the same method as that used in Example 78, except that the reaction time was changed to 7 hours. Thereafter, a reaction product was separated by the same method as that used in Example 87, and the reaction product thus obtained was separated into an epoxy compound and the episulfide compound by the same method as that used in Example 148.

Example 230

An episulfide compound was produced by the same method as that used in Example 79, except that the reaction time was changed to one hour. Thereafter, a reaction product was separated by the same method as that used in Example 87, and the reaction product thus obtained was separated into an epoxy compound and the episulfide compound by the same method as that used in Example 148.

The production results in Examples 197 to 230, the epoxy compound content of the epoxy compound thus separated, and the episulfide compound content of the episulfide compound thus separated are presented in Table 9.

TABLE 9

| | Epoxy group reaction rate (%) | Episulfide group yield (%) | Reaction time HR | Epoxy compound content (%) | Episulfide compound content (%) |
|---|---|---|---|---|---|
| Example 197 | 72 | 71 | 1 | 99 | 99 |
| Example 198 | 53 | 50 | 2 | 99 | 99 |
| Example 199 | 56 | 54 | 2 | 99 | 99 |
| Example 200 | 71 | 68 | 1 | 99 | 99 |
| Example 201 | 58 | 55 | 1 | 99 | 99 |
| Example 202 | 74 | 72 | 1 | 99 | 99 |
| Example 203 | 82 | 80 | 1 | 99 | 99 |
| Example 204 | 71 | 70 | 0.5 | 99 | 99 |
| Example 205 | 70 | 68 | 1 | 99 | 99 |
| Example 206 | 80 | 79 | 1 | 99 | 99 |
| Example 207 | 79 | 77 | 1 | 99 | 99 |
| Example 208 | 74 | 73 | 2 | 99 | 99 |
| Example 209 | 80 | 78 | 1 | 99 | 99 |
| Example 210 | 68 | 66 | 1 | 99 | 99 |
| Example 211 | 75 | 74 | 1 | 99 | 99 |
| Example 212 | 72 | 70 | 2 | 99 | 99 |
| Example 213 | 63 | 61 | 2 | 99 | 99 |
| Example 214 | 66 | 63 | 2 | 99 | 99 |
| Example 215 | 61 | 58 | 2 | 99 | 99 |
| Example 216 | 54 | 51 | 4 | 99 | 99 |
| Example 217 | 70 | 68 | 3 | 99 | 99 |
| Example 218 | 57 | 53 | 6 | 99 | 99 |
| Example 219 | 58 | 55 | 7 | 99 | 99 |
| Example 220 | 68 | 66 | 5 | 99 | 99 |
| Example 221 | 72 | 71 | 1 | 99 | 99 |
| Example 222 | 79 | 78 | 0.5 | 99 | 99 |
| Example 223 | 65 | 63 | 5 | 99 | 99 |
| Example 224 | 80 | 79 | 0.5 | 99 | 99 |
| Example 225 | 70 | 68 | 6 | 99 | 99 |
| Example 226 | 53 | 50 | 1 | 99 | 99 |
| Example 227 | 74 | 72 | 1 | 99 | 99 |
| Example 228 | 80 | 78 | 0.5 | 99 | 99 |
| Example 229 | 65 | 63 | 7 | 99 | 99 |
| Example 230 | 72 | 70 | 1 | 99 | 99 |

Example 231

An episulfide compound was produced by the same method as that used in Example 4, except that an epoxy compound separated from the reaction product obtained in Example 197 was used. As shown in Table 10, since the reaction time taken until the epoxy group reaction rate reached 100% was 2 hours, the reaction time was considered particularly satisfactory. Furthermore, since the episulfide group yield was 95%, the yield was considered particularly satisfactory. From these results, an overall decision was made that the process was acceptable.

Example 232

An episulfide compound was produced by the same method as that used in Example 39, except that an epoxy compound separated from the reaction product obtained in Example 198 was used. As shown in Table 10, since the reaction time taken until the epoxy group reaction rate reached 100% was 6 hours, the reaction time was considered particularly satisfactory. Furthermore, since the episulfide group yield was 84%, the yield was considered satisfactory. From these results, an overall decision was made that the process was acceptable.

Example 233

An episulfide compound was produced by the same method as that used in Example 40, except that an epoxy compound separated from the reaction product obtained in Example 199 was used. As shown in Table 10, since the reaction time taken until the epoxy group reaction rate reached 100% was 6 hours, the reaction time was considered particularly satisfactory. Furthermore, since the episulfide group yield was 88%, the yield was considered satisfactory. From these results, an overall decision was made that the process was acceptable.

Example 234

An episulfide compound was produced by the same method as that used in Example 41, except that an epoxy compound separated from the reaction product obtained in Example 200 was used. As shown in Table 10, since the reaction time taken until the epoxy group reaction rate reached 100% was 2 hours, the reaction time was considered particularly satisfactory. Furthermore, since the episulfide group yield was 87%, the yield was considered satisfactory. From these results, an overall decision was made that the process was acceptable.

Example 235

An episulfide compound was produced by the same method as that used in Example 42, except that an epoxy compound separated from the reaction product obtained in Example 201 was used. As shown in Table 10, since the reaction time taken until the epoxy group reaction rate reached 100% was 3 hours, the reaction time was considered particularly satisfactory. Furthermore, since the episulfide group yield was 88%, the yield was considered satisfactory. From these results, an overall decision was made that the process was acceptable.

Example 236

An episulfide compound was produced by the same method as that used in Example 43, except that an epoxy compound separated from the reaction product obtained in Example 202 was used. As shown in Table 10, since the reaction time taken until the epoxy group reaction rate reached 100% was 3 hours, the reaction time was considered particularly satisfactory. Furthermore, since the episulfide group yield was 93%, the yield was considered particularly satisfactory. From these results, an overall decision was made that the process was acceptable.

Example 237

An episulfide compound was produced by the same method as that used in Example 44, except that an epoxy compound separated from the reaction product obtained in Example 203 was used. As shown in Table 10, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Example 238

An episulfide compound was produced by the same method as that used in Example 45, except that an epoxy compound separated from the reaction product obtained in Example 204 was used. As shown in Table 10, since the reaction time taken until the epoxy group reaction rate reached 100% was one hour, the reaction time was considered particularly satisfactory. Furthermore, since the episulfide group yield was 95%, the yield was considered particularly satisfactory. From these results, an overall decision was made that the process was acceptable.

Example 239

An episulfide compound was produced by the same method as that used in Example 46, except that an epoxy compound separated from the reaction product obtained in Example 205 was used. As shown in Table 10, since the reaction time taken until the epoxy group reaction rate reached 100% was 3 hours, the reaction time was considered particularly satisfactory. Furthermore, since the episulfide group yield was 93%, the yield was considered particularly satisfactory. From these results, an overall decision was made that the process was acceptable.

Example 240

An episulfide compound was produced by the same method as that used in Example 47, except that an epoxy compound separated from the reaction product obtained in Example 206 was used. As shown in Table 10, since the reaction time taken until the epoxy group reaction rate reached 100% was 2 hours, the reaction time was considered particularly satisfactory. Furthermore, since the episulfide group yield was 95%, the yield was considered particularly satisfactory. From these results, an overall decision was made that the process was acceptable.

Example 241

An episulfide compound was produced by the same method as that used in Example 48, except that an epoxy compound separated from the reaction product obtained in Example 207 was used. As shown in Table 10, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Example 242

An episulfide compound was produced by the same method as that used in Example 49, except that an epoxy compound separated from the reaction product obtained in Example 208 was used. As shown in Table 10, since the reaction time taken until the epoxy group reaction rate reached 100% was 4 hours, the reaction time was considered particularly satisfactory. Furthermore, since the episulfide group yield was 95%, the yield was considered particularly satisfactory. From these results, an overall decision was made that the process was acceptable.

Example 243

An episulfide compound was produced by the same method as that used in Example 50, except that an epoxy compound separated from the reaction product obtained in Example 209 was used. As shown in Table 10, since the reaction time taken until the epoxy group reaction rate reached 100% was 2 hours, the reaction time was considered particularly satisfactory. Furthermore, since the episulfide group yield was 94%, the yield was considered particularly satisfactory. From these results, an overall decision was made that the process was acceptable.

Example 244

An episulfide compound was produced by the same method as that used in Example 51, except that an epoxy compound separated from the reaction product obtained in Example 210 was used. As shown in Table 10, since the reaction time taken until the epoxy group reaction rate reached 100% was 3 hours, the reaction time was considered particularly satisfactory. Furthermore, since the episulfide group yield was 95%, the yield was considered particularly satisfactory. From these results, an overall decision was made that the process was acceptable.

Example 245

An episulfide compound was produced by the same method as that used in Example 52, except that an epoxy compound separated from the reaction product obtained in Example 211 was used. As shown in Table 10, since the reaction time taken until the epoxy group reaction rate reached 100% was 2 hours, the reaction time was considered particularly satisfactory. Furthermore, since the episulfide group yield was 96%, the yield was considered particularly satisfactory. From these results, an overall decision was made that the process was acceptable.

Example 246

An episulfide compound was produced by the same method as that used in Example 53, except that an epoxy compound separated from the reaction product obtained in Example 212 was used. As shown in Table 10, since the reaction time taken until the epoxy group reaction rate reached 100% was 4 hours, the reaction time was considered particularly satisfactory. Furthermore, since the episulfide group yield was 94%, the yield was considered particularly satisfactory. From these results, an overall decision was made that the process was acceptable.

Example 247

An episulfide compound was produced by the same method as that used in Example 54, except that an epoxy compound separated from the reaction product obtained in Example 213 was used. As shown in Table 10, since the reaction time taken until the epoxy group reaction rate reached 100% was 6 hours, the reaction time was considered particularly satisfactory. Furthermore, since the episulfide group yield was 92%, the yield was considered particularly satisfactory. From these results, an overall decision was made that the process was acceptable.

Example 248

An episulfide compound was produced by the same method as that used in Example 55, except that an epoxy compound separated from the reaction product obtained in Example 214 was used. As shown in Table 10, since the reaction time taken until the epoxy group reaction rate reached 100% was 5 hours, the reaction time was considered particularly satisfactory. Furthermore, since the episulfide group yield was 88%, the yield was considered satisfactory. From these results, an overall decision was made that the process was acceptable.

Example 249

An episulfide compound was produced by the same method as that used in Example 56, except that an epoxy compound separated from the reaction product obtained in Example 215 was used. As shown in Table 10, since the reaction time taken until the epoxy group reaction rate reached 100% was 6 hours, the reaction time was considered particularly satisfactory. Furthermore, since the episulfide group yield was 84%, the yield was considered satisfactory. From these results, an overall decision was made that the process was acceptable.

Example 250

An episulfide compound was produced by the same method as that used in Example 65, except that an epoxy compound separated from the reaction product obtained in Example 216 was used. As shown in Table 10, since the reaction time taken until the epoxy group reaction rate reached 100% was 12 hours, the reaction time was considered satisfactory. Furthermore, since the episulfide group yield was 84%, the yield was considered satisfactory. From these results, an overall decision was made that the process was acceptable.

Example 251

An episulfide compound was produced by the same method as that used in Example 66, except that an epoxy compound separated from the reaction product obtained in Example 217 was used. As shown in Table 10, since the reaction time taken until the epoxy group reaction rate reached 100% was 8 hours, the reaction time was considered satisfactory. Furthermore, since the episulfide group yield was 92%, the yield was considered particularly satisfactory. From these results, an overall decision was made that the process was acceptable.

Example 252

An episulfide compound was produced by the same method as that used in Example 67, except that an epoxy compound separated from the reaction product obtained in Example 218 was used. As shown in Table 10, since the reaction time taken until the epoxy group reaction rate reached 100% was 18 hours, the reaction time was considered satisfactory. Furthermore, since the episulfide group yield was 82%, the yield was considered satisfactory. From these results, an overall decision was made that the process was acceptable.

Example 253

An episulfide compound was produced by the same method as that used in Example 68, except that an epoxy compound separated from the reaction product obtained in Example 219 was used. As shown in Table 10, since the reaction time taken until the epoxy group reaction rate reached 100% was 22 hours, the reaction time was considered satisfactory. Furthermore, since the episulfide group yield was 85%, the yield was considered satisfactory. From these results, an overall decision was made that the process was acceptable.

Example 254

An episulfide compound was produced by the same method as that used in Example 69, except that an epoxy compound separated from the reaction product obtained in Example 220 was used. As shown in Table 10, since the reaction time taken until the epoxy group reaction rate reached 100% was 15 hours, the reaction time was considered satisfactory. Furthermore, since the episulfide group yield was 94%, the yield was considered particularly satisfactory. From these results, an overall decision was made that the process was acceptable.

Example 255

An episulfide compound was produced by the same method as that used in Example 70, except that an epoxy compound separated from the reaction product obtained in Example 221 was used. As shown in Table 10, since the reaction time taken until the epoxy group reaction rate reached 100% was 2 hours, the reaction time was considered particularly satisfactory. Furthermore, since the episulfide group yield was 95%, the yield was considered particularly satisfactory. From these results, an overall decision was made that the process was acceptable.

Example 256

An episulfide compound was produced by the same method as that used in Example 71, except that an epoxy compound separated from the reaction product obtained in Example 222 was used. As shown in Table 10, since the reaction time taken until the epoxy group reaction rate reached 100% was one hour, the reaction time was considered particularly satisfactory. Furthermore, since the episulfide group yield was 96%, the yield was considered particularly satisfactory. From these results, an overall decision was made that the process was acceptable.

Example 257

An episulfide compound was produced by the same method as that used in Example 72, except that an epoxy compound separated from the reaction product obtained in Example 223 was used. As shown in Table 10, since the reaction time taken until the epoxy group reaction rate reached 100% was 15 hours, the reaction time was considered satisfactory. Furthermore, since the episulfide group yield was 92%, the yield was considered particularly satisfactory. From these results, an overall decision was made that the process was acceptable.

Example 258

An episulfide compound was produced by the same method as that used in Example 73, except that an epoxy compound separated from the reaction product obtained in Example 224 was used. As shown in Table 10, since the reaction time taken until the epoxy group reaction rate reached 100% was one hour, the reaction time was considered particularly satisfactory. Furthermore, since the episulfide group yield was 96%, the yield was considered particularly satisfactory. From these results, an overall decision was made that the process was acceptable.

Example 259

An episulfide compound was produced by the same method as that used in Example 74, except that an epoxy compound separated from the reaction product obtained in Example 225 was used. As shown in Table 10, since the reaction time taken until the epoxy group reaction rate reached 100% was 18 hours, the reaction time was considered satisfactory. Furthermore, since the episulfide group yield was 91%, the yield was considered particularly satisfactory. From these results, an overall decision was made that the process was acceptable.

Example 260

An episulfide compound was produced by the same method as that used in Example 75, except that an epoxy compound separated from the reaction product obtained in Example 226 was used. As shown in Table 10, since the reaction time taken until the epoxy group reaction rate reached 100% was 4 hours, the reaction time was considered particularly satisfactory. Furthermore, since the episulfide group yield was 84%, the yield was considered satisfactory. From these results, an overall decision was made that the process was acceptable.

Example 261

An episulfide compound was produced by the same method as that used in Example 76, except that an epoxy compound separated from the reaction product obtained in Example 227 was used. As shown in Table 10, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Example 262

An episulfide compound was produced by the same method as that used in Example 77, except that an epoxy compound separated from the reaction product obtained in Example 228 was used. As shown in Table 10, since the reaction time taken until the epoxy group reaction rate reached 100% was one hour, the reaction time was considered particularly satisfactory. Furthermore, since the episulfide group yield was 95%, the yield was considered particularly satisfactory. From these results, an overall decision was made that the process was acceptable.

Example 263

An episulfide compound was produced by the same method as that used in Example 78, except that an epoxy compound separated from the reaction product obtained in Example 229 was used. As shown in Table 10, since the reaction time taken until the epoxy group reaction rate reached 100% was 20 hours, the reaction time was considered satisfactory. Furthermore, since the episulfide group yield was 92%, the yield was considered particularly satisfactory. From these results, an overall decision was made that the process was acceptable.

Example 264

An episulfide compound was produced by the same method as that used in Example 79, except that an epoxy compound separated from the reaction product obtained in Example 230 was used. As shown in Table 10, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Examples 265 to 279

A polyhydric hydroxyl compound was separated from each of the ultrapure water layers obtained in Examples 87 to 102, by the same method as that used in Example 148.

Example 280

A polyhydric hydroxyl compound was separated by the following procedure from the ultrapure water layer obtained in Example 102.

(1) Low boiling point compounds (including water) that were contained in the ultrapure water layer were distilled off using a rotary evaporator, and thus a polyhydric hydroxyl compound-containing crude product was obtained.

(2) A polyhydric hydroxyl compound was separated from the polyhydric hydroxyl compound-containing crude product obtained in step (1), by the same method as that used in Example 168.

Examples 281 to 287

A polyhydric hydroxyl compound was separated by the same method as that used in Example 280, except that the ultrapure water obtained in each of Examples 103 and 140 to 145 was used.

Example 288

An episulfide compound was produced by the same method as that used in Example 1, except that the polyhydric hydroxyl compound obtained in Example 265 was used. As shown in Table 11, since the reaction time taken until the epoxy group reaction rate reached 100% was 4 hours, the reaction time was considered particularly satisfactory. Furthermore, since the episulfide group yield was 87%, the yield was considered satisfactory. From these results, an overall decision was made that the process was acceptable.

Example 289

An episulfide compound was produced by the same method as that used in Example 2, except that the polyhydric hydroxyl compound obtained in Example 266 was used. As shown in Table 11, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Example 290

An episulfide compound was produced by the same method as that used in Example 3, except that the polyhydric hydroxyl compound obtained in Example 267 was used. As shown in Table 11, since the reaction time taken until the epoxy group reaction rate reached 100% was 4 hours, the reaction time was considered particularly satisfactory. Furthermore, since the episulfide group yield was 92%, the yield was considered particularly satisfactory. From these results, an overall decision was made that the process was acceptable.

Example 291

An episulfide compound was produced by the same method as that used in Example 4, except that the polyhydric hydroxyl compound obtained in Example 268 was used. As shown in Table 11, since the reaction time taken until the epoxy group reaction rate reached 100% was 2 hours, the reaction time was considered particularly satisfactory. Furthermore, since the episulfide group yield was 96%, the yield was considered particularly satisfactory. From these results, an overall decision was made that the process was acceptable.

Example 292

An episulfide compound was produced by the same method as that used in Example 5, except that the polyhydric hydroxyl compound obtained in Example 269 was used. As shown in Table 11, since the reaction time taken until the epoxy group reaction rate reached 100% was 4 hours, the reaction time was considered particularly satisfactory. Furthermore, since the episulfide group yield was 93%, the yield was considered particularly satisfactory. From these results, since the properties were simultaneously particularly satisfactory, an overall decision was made that the process was acceptable.

Example 293

An episulfide compound was produced by the same method as that used in Example 6, except that the polyhydric hydroxyl compound obtained in Example 270 was used. As shown in Table 11, since the reaction time taken until the epoxy group reaction rate reached 100% was 2 hours, the reaction time was considered particularly satisfactory. Furthermore, since the episulfide group yield was 95%, the yield was considered particularly satisfactory. From these results, an overall decision was made that the process was acceptable.

Example 294

An episulfide compound was produced by the same method as that used in Example 7, except that the polyhydric hydroxyl compound obtained in Example 271 was used. As shown in Table 11, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Example 295

An episulfide compound was produced by the same method as that used in Example 8, except that the polyhydric hydroxyl compound obtained in Example 272 was used. As shown in Table 11, since the reaction time taken until the epoxy group reaction rate reached 100% was 2 hours, the reaction time was considered particularly satisfactory. Furthermore, since the episulfide group yield was 93%, the yield was considered particularly satisfactory. From these results, an overall decision was made that the process was acceptable.

Example 296

An episulfide compound was produced by the same method as that used in Example 9, except that the polyhydric hydroxyl compound obtained in Example 273 was used. As shown in Table 11, since the reaction time taken until the epoxy group reaction rate reached 100% was 3 hours, the reaction time was considered particularly satisfactory. Furthermore, since the episulfide group yield was 92%, the yield was considered particularly satisfactory. From these results, an overall decision was made that the process was acceptable.

Example 297

An episulfide compound was produced by the same method as that used in Example 10, except that the polyhydric hydroxyl compound obtained in Example 274 was used. As shown in Table 11, since the reaction time taken until the epoxy group reaction rate reached 100% was 20 hours, the reaction time was considered satisfactory. Furthermore, since the episulfide group yield was 81%, the yield was considered satisfactory. From these results, since the properties were simultaneously satisfactory, an overall decision was made that the process was acceptable.

Example 298

An episulfide compound was produced by the same method as that used in Example 11, except that the polyhydric hydroxyl compound obtained in Example 275 was used. As shown in Table 11, since the reaction time taken until the epoxy group reaction rate reached 100% was 7 hours, the reaction time was considered satisfactory. Furthermore, since the episulfide group yield was 89%, the yield was considered satisfactory. From these results, an overall decision was made that the process was acceptable.

Example 299

An episulfide compound was produced by the same method as that used in Example 12, except that the polyhydric hydroxyl compound obtained in Example 276 was used. As shown in Table 11, since the reaction time taken until the epoxy group reaction rate reached 100% was 12 hours, the reaction time was considered satisfactory. Furthermore, since the episulfide group yield was 86%, the yield was considered satisfactory. From these results, an overall decision was made that the process was acceptable.

Example 300

An episulfide compound was produced by the same method as that used in Example 13, except that the polyhydric hydroxyl compound obtained in Example 277 was used. As shown in Table 11, since the reaction time taken until the epoxy group reaction rate reached 100% was 12 hours, the reaction time was considered satisfactory. Furthermore, since the episulfide group yield was 84%, the yield was considered satisfactory. From these results, an overall decision was made that the process was acceptable.

Example 301

An episulfide compound was produced by the same method as that used in Example 14, except that the polyhydric hydroxyl compound obtained in Example 278 was used. As shown in Table 11, since the reaction time taken until the epoxy group reaction rate reached 100% was 15 hours, the reaction time was considered satisfactory. Furthermore, since the episulfide group yield was 85%, the yield was considered satisfactory. From these results, an overall decision was made that the process was acceptable.

Example 302

An episulfide compound was produced by the same method as that used in Example 15, except that the polyhydric hydroxyl compound obtained in Example 279 was used. As shown in Table 11, since the reaction time taken until the epoxy group reaction rate reached 100% was 19 hours, the reaction time was considered satisfactory. Furthermore, since the episulfide group yield was 83%, the yield was considered satisfactory. From these results, an overall decision was made that the process was acceptable.

Example 303

An episulfide compound was produced by the same method as that used in Example 16, except that the polyhydric hydroxyl compound obtained in Example 280 was used. As shown in Table 11, since the reaction time taken until the epoxy group reaction rate reached 100% was 20 hours, the reaction time was considered satisfactory. Furthermore, since the episulfide group yield was 82%, the yield was considered satisfactory. From these results, an overall decision was made that the process was acceptable.

Example 304

An episulfide compound was produced by the same method as that used in Example 17, except that the polyhydric hydroxyl compound obtained in Example 281 was used. As shown in Table 11, since the reaction time taken until the epoxy group reaction rate reached 100% was 23 hours, the reaction time was considered satisfactory. Furthermore, since the episulfide group yield was 81%, the yield was considered satisfactory. From these results, an overall decision was made that the process was acceptable.

Example 305

An episulfide compound was produced by the same method as that used in Example 80, except that the polyhydric hydroxyl compound obtained in Example 282 was used. As shown in Table 11, since the reaction time taken until the epoxy group reaction rate reached 100% was 9 hours, the reaction time was considered satisfactory. Furthermore, since the episulfide group yield was 89%, the yield was considered satisfactory. From these results, an overall decision was made that the process was acceptable.

Example 306

An episulfide compound was produced by the same method as that used in Example 81, except that the polyhydric hydroxyl compound obtained in Example 283 was used. As shown in Table 11, since the reaction time taken until the epoxy group reaction ratio reached 100% was 12 hours, the reaction time was considered satisfactory. Furthermore, since the episulfide group yield was 87%, the yield was considered satisfactory. From these results, an overall decision was made that the process was acceptable.

Example 307

An episulfide compound was produced by the same method as that used in Example 82, except that the polyhydric hydroxyl compound obtained in Example 284 was used. As shown in Table 11, since the reaction time taken until the epoxy group reaction rate reached 100% was 12 hours, the reaction time was considered satisfactory. Furthermore, since the episulfide group yield was 85%, the yield was considered satisfactory. From these results, an overall decision was made that the process was acceptable.

Example 308

An episulfide compound was produced by the same method as that used in Example 83, except that the polyhydric hydroxyl compound obtained in Example 285 was used. As shown in Table 11, since the reaction time taken until the epoxy group reaction rate reached 100% was 16 hours, the reaction time was considered satisfactory. Furthermore, since the episulfide group yield was 83%, the yield was considered satisfactory. From these results, an overall decision was made that the process was acceptable.

Example 309

An episulfide compound was produced by the same method as that used in Example 84, except that the polyhydric hydroxyl compound obtained in Example 286 was used. As shown in Table 11, since the reaction time taken until the epoxy group reaction rate reached 100% was 20 hours, the reaction time was considered satisfactory. Furthermore, since the episulfide group yield was 82%, the yield was considered satisfactory. From these results, an overall decision was made that the process was acceptable.

Example 310

An episulfide compound was produced by the same method as that used in Example 85, except that the polyhydric hydroxyl compound obtained in Example 287 was used. As shown in Table 11, since the reaction time taken until the epoxy group reaction rate reached 100% was 23 hours, the reaction time was considered satisfactory. Furthermore, since the episulfide group yield was 81%, the yield was considered satisfactory. From these results, an overall decision was made that the process was acceptable.

Examples 311 to 313

A distillation residue was obtained by the same method as that used in Example 148, except that each of the reaction liquids obtained in Examples 57 to 59 was used.

Example 314

A thiating agent was regenerated by the following procedure, using the distillation residue obtained when the polyhydric hydroxyl compound was separated in Example 265.

(1) Boiled ultrapure water (manufactured by Wako Pure Chemical Industries, Ltd.) was added to the distillation residue to obtain a saturated solution.

(2) The saturated solution of step (1) was cooled to room temperature, and a mixture of a thiating agent and a compound produced as a result of the substitution of a sulfur atom of the thiating agent with an oxygen atom was precipitated and collected by filtration.

(3) A regenerated thiating agent was obtained according to the method described in "Faming Zhuanli Shenqing Gongkai Shuomingshu (2009), CN 101602702", using the mixture of step (2) of the thiating agent and a compound produced as a result of the substitution of a sulfur atom of the thiating agent with an oxygen atom.

(4) The purity of the regenerated thiating agent thus obtained was measured according to the method described above, and the purity was found to be 99%.

Examples 315 to 330

A regenerated thiating agent was obtained by the same technique as that used in Example 314, except that the distillation residue obtained when each of the polyhydric hydroxyl compounds of Examples 266 to 281 was separated. In all cases, the purity of the regenerated thiating agents thus obtained was 99%.

Example 331

A thiating agent was regenerated by the following procedure, using the distillation residue obtained in Example 311.

(1) Boiled ultrapure water (manufactured by Wako Pure Chemical Industries, Ltd.) was added to the distillation residue to obtain a saturated solution.

(2) The saturated solution of step (1) was cooled to room temperature, and a mixture of a thiating agent and a compound produced as a result of the substitution of a sulfur atom of the thiating agent with an oxygen atom was precipitated and collected by filtration.

(3) 2,4-Bis(methylthio)-1,3,2,4-dithiadiphosphetane-2,4-disulfide was produced according to the method described in "Encyclopedia of Reagent for Organic Synthesis (published by John Wiley and Sons, Inc.)".

(4) The mixture of step (2) and the compound of step (3) were dissolved in a mixed solvent of 1,4-dioxane (manufactured by Wako Pure Chemical Industries, Ltd.) and ultrapure water (manufactured by Wako Pure Chemical Industries, Ltd.).

(5) An oil bath including oil and a stirrer was mounted on a magnetic stirrer, and the temperature of the oil was set to 80° C.

(6) The solution of step (4) and a stirring bar were introduced into a flask, and the solution was mixed and stirred. The stirred solution was immersed in the oil bath.

(7) After 30 hours passed, the flask of step (6) was taken out from the oil bath and was cooled to room temperature.

(8) Ethyl acetate (manufactured by Wako Pure Chemical Industries, Ltd.) and ultrapure water (manufactured by Wako Pure Chemical Industries, Ltd.) were added to the flask of step (7), and then the mixture was mixed and stirred. Subsequently, the mixture was left to stand still until layer separation of an ethyl acetate layer and an ultrapure water layer occurred.

(9) The ultrapure water layer was separated, and then low boiling point compounds (including water) that were contained in the ultrapure water layer were distilled off using a rotary evaporator. Thus, a crude regenerated thiating agent was obtained.

(10) Boiled ultrapure water (manufactured by Wako Pure Chemical Industries, Ltd.) was added to the crude regenerated thiating agent to obtain a saturated solution.

(11) The saturated solution of step (10) was cooled to room temperature, and the regenerated thiating agent was precipitated and collected by filtration.

(12) The purity of the regenerated thiating agent thus obtained was measured according to the method described above, and the purity was found to be 99%.

Examples 332 and 333

A regenerated thiating agent was obtained by the same technique as that used in Example 331, except that each of the distillation residues obtained in Examples 312 and 313 was used. In all cases, the purity of the regenerated thiating agents thus obtained was 99%.

Example 334

An episulfide compound was produced by the same method as that used in Example 1, except that the regenerated thiating agent obtained in Example 314 was used. As shown in Table 12, since the reaction time taken until the epoxy group reaction rate reached 100% was 4 hours, the reaction time was considered particularly satisfactory. Furthermore, since the episulfide group yield was 87%, the yield was considered satisfactory. From these results, an overall decision was made that the process was acceptable.

Example 335

An episulfide compound was produced by the same method as that used in Example 2, except that the regenerated thiating agent obtained in Example 315 was used. As shown in Table 12, since the reaction time taken until the epoxy group reaction rate reached 100% was 2 hours, the reaction time was considered particularly satisfactory. Furthermore, since the episulfide group yield was 94%, the yield was considered particularly satisfactory. From these results, an overall decision was made that the process was acceptable.

Example 336

An episulfide compound was produced by the same method as that used in Example 3, except that the regenerated thiating agent obtained in Example 316 was used. As shown in Table 12, since the reaction time taken until the epoxy group reaction rate reached 100% was 4 hours, the reaction time was considered particularly satisfactory. Furthermore, since the episulfide group yield was 92%, the yield was considered particularly satisfactory. From these results, an overall decision was made that the process was acceptable.

Example 337

An episulfide compound was produced by the same method as that used in Example 4, except that the regenerated thiating agent obtained in Example 317 was used. As shown in Table 12, since the reaction time taken until the epoxy group reaction rate reached 100% was 2 hours, the reaction time was considered particularly satisfactory. Furthermore, since the episulfide group yield was 95%, the yield was considered particularly satisfactory. From these results, an overall decision was made that the process was acceptable.

Example 338

An episulfide compound was produced by the same method as that used in Example 5, except that the regenerated

Example 339

An episulfide compound was produced by the same method as that used in Example 6, except that the regenerated thiating agent obtained in Example 319 was used. As shown in Table 12, since the reaction time taken until the epoxy group reaction rate reached 100% was 2 hours, the reaction time was considered particularly satisfactory. Furthermore, since the episulfide group yield was 96%, the yield was considered particularly satisfactory. From these results, an overall decision was made that the process was acceptable.

Example 340

An episulfide compound was produced by the same method as that used in Example 7, except that the regenerated thiating agent obtained in Example 320 was used. As shown in Table 12, since the reaction time taken until the epoxy group reaction rate reached 100% was 2 hours, the reaction time was considered particularly satisfactory. Furthermore, since the episulfide group yield was 92%, the yield was considered particularly satisfactory. From these results, an overall decision was made that the process was acceptable.

Example 341

An episulfide compound was produced by the same method as that used in Example 8, except that the regenerated thiating agent obtained in Example 321 was used. As shown in Table 12, since the reaction time taken until the epoxy group reaction rate reached 100% was 2 hours, the reaction time was considered particularly satisfactory. Furthermore, since the episulfide group yield was 94%, the yield was considered particularly satisfactory. From these results, an overall decision was made that the process was acceptable.

Example 342

An episulfide compound was produced by the same method as that used in Example 9, except that the regenerated thiating agent obtained in Example 322 was used. As shown in Table 12, since the reaction time taken until the epoxy group reaction rate reached 100% was 3 hours, the reaction time was considered particularly satisfactory. Furthermore, since the episulfide group yield was 92%, the yield was considered particularly satisfactory. From these results, an overall decision was made that the process was acceptable.

Example 343

An episulfide compound was produced by the same method as that used in Example 10, except that the regenerated thiating agent obtained in Example 323 was used. As shown in Table 12, since the reaction time taken until the epoxy group reaction rate reached 100% was 20 hours, the reaction time was considered satisfactory. Furthermore, since the episulfide group yield was 81%, the yield was considered satisfactory. From these results, an overall decision was made that the process was acceptable.

Example 344

An episulfide compound was produced by the same method as that used in Example 11, except that the regenerated thiating agent obtained in Example 324 was used. As shown in Table 12, since the reaction time taken until the epoxy group reaction rate reached 100% was 7 hours, the reaction time was considered satisfactory. Furthermore, since the episulfide group yield was 89%, the yield was considered satisfactory. From these results, an overall decision was made that the process was acceptable.

Example 345

An episulfide compound was produced by the same method as that used in Example 12, except that the regenerated thiating agent obtained in Example 325 was used. As shown in Table 12, since the reaction time taken until the epoxy group reaction rate reached 100% was 12 hours, the reaction time was considered satisfactory. Furthermore, since the episulfide group yield was 86%, the yield was considered satisfactory. From these results, an overall decision was made that the process was acceptable.

Example 346

An episulfide compound was produced by the same method as that used in Example 13, except that the regenerated thiating agent obtained in Example 326 was used. As shown in Table 12, since the reaction time taken until the epoxy group reaction rate reached 100% was 12 hours, the reaction time was considered satisfactory. Furthermore, since the episulfide group yield was 83%, the yield was considered satisfactory. From these results, an overall decision was made that the process was acceptable.

Example 347

An episulfide compound was produced by the same method as that used in Example 14, except that the regenerated thiating agent obtained in Example 327 was used. As shown in Table 12, since the reaction time taken until the epoxy group reaction rate reached 100% was 15 hours, the reaction time was considered satisfactory. Furthermore, since the episulfide group yield was 85%, the yield was considered satisfactory. From these results, an overall decision was made that the process was acceptable.

Example 348

An episulfide compound was produced by the same method as that used in Example 15, except that the regenerated thiating agent obtained in Example 328 was used. As shown in Table 12, since the reaction time taken until the epoxy group reaction rate reached 100% was 19 hours, the reaction time was considered satisfactory. Furthermore, since the episulfide group yield was 82%, the yield was considered satisfactory. From these results, an overall decision was made that the process was acceptable.

Example 349

An episulfide compound was produced by the same method as that used in Example 57, except that the regenerated thiating agent obtained in Example 331 was used. As shown in Table 12, since the reaction time taken until the epoxy group reaction rate reached 100% was 4 hours, the reaction time was considered particularly satisfactory. Furthermore, since the episulfide group yield was 88%, the yield was considered satisfactory. From these results, an overall decision was made that the process was acceptable.

Example 350

An episulfide compound was produced by the same method as that used in Example 58, except that the regenerated thiating agent obtained in Example 332 was used. As shown in Table 12, since the reaction time taken until the epoxy group reaction rate reached 100% was 4 hours, the reaction time was considered particularly satisfactory. Furthermore, since the episulfide group yield was 88%, the yield was considered satisfactory. From these results, an overall decision was made that the process was acceptable.

Example 351

An episulfide compound was produced by the same method as that used in Example 59, except that the regenerated thiating agent obtained in Example 333 was used. As shown in Table 12, since the reaction time taken until the epoxy group reaction rate reached 100% was 4 hours, the reaction time was considered particularly satisfactory. Furthermore, since the episulfide group yield was 88%, the yield was considered satisfactory. From these results, an overall decision was made that the process was acceptable.

Example 352

A thiating agent was separated by the following procedure, using the distillation residue obtained when the polyhydric hydroxyl compound was separated in Example 265.

(1) Boiled ultrapure water (manufactured by Wako Pure Chemical Industries, Ltd.) was added to the distillation residue to obtain a saturated solution.

(2) The saturated solution of step (1) was cooled to room temperature, and a mixture of a thiating agent and a compound produced as a result of the substitution of a sulfur atom of the thiating agent with an oxygen atom was precipitated and collected by filtration.

(3) The operations of the steps (1) and (2) were repeated using the mixture of the thiating agent and a compound produced as a result of the substitution of a sulfur atom of the thiating agent with an oxygen atom of (2), and thus the thiating agent was separated.

(4) The purity of the thiating agent thus obtained was measured according to the method described above, and the purity was found to be 99%.

Examples 353 to 355

A thiating agent was separated by the same method as that used in Example 352, except that each of the distillation residues obtained when the polyhydric hydroxyl compound was separated in Examples 311 to 313 was used. In all cases, the purity of the thiating agent thus obtained was 99%.

Example 356

An episulfide compound was produced by the same method as that used in Example 4, except that the thiating agent obtained in Example 352 was used. As a result, since the reaction time taken until the epoxy group reaction rate reached 100% was 2 hours, the reaction time was considered particularly satisfactory. Furthermore, since the episulfide group yield was 95%, the yield was considered particularly satisfactory. From these results, an overall decision was made that the process was acceptable.

Example 357

An episulfide compound was produced by the same method as that used in Example 57, except that the thiating agent obtained in Example 353 was used. As a result, since the reaction time taken until the epoxy group reaction rate reached 100% was 4 hours, the reaction time was considered particularly satisfactory. Furthermore, since the episulfide group yield was 87%, the yield was considered satisfactory. From these results, an overall decision was made that the process was acceptable.

Example 358

An episulfide compound was produced by the same method as that used in Example 58, except that the thiating agent obtained in Example 354 was used. As a result, since the reaction time taken until the epoxy group reaction rate reached 100% was 4 hours, the reaction time was considered particularly satisfactory. Furthermore, since the episulfide group yield was 88%, the yield was considered satisfactory. From these results, an overall decision was made that the process was acceptable.

Example 359

An episulfide compound was produced by the same method as that used in Example 59, except that the thiating agent obtained in Example 355 was used. As a result, since the reaction time taken until the epoxy group reaction rate reached 100% was 2 hours, the reaction time was considered particularly satisfactory. Furthermore, since the episulfide group yield was 87%, the yield was considered satisfactory. From these results, an overall decision was made that the process was acceptable.

TABLE 10

<Decision> AA: particularly satisfactory, A: satisfactory, C: poor,
<Overall decision> AA, A: acceptable, C: unacceptable

| | HV (mg/g) | WPE (g/eq) | α | β | ε | Reaction temperature (° C.) | Epoxy group reaction rate (%) | Episulfide group yield (%) | Decision | Reaction time HR | Decision | Overall decision |
|---|---|---|---|---|---|---|---|---|---|---|---|---|
| Example 231 | 1245 | 150 | 2 | 0.28 | — | 20 | 100 | 95 | AA | 2 | AA | AA |
| Example 232 | 1078 | 44 | 2 | 0.10 | — | 0 | 100 | 84 | A | 6 | AA | A |

TABLE 10-continued

<Decision> AA: particularly satisfactory, A: satisfactory, C: poor,
<Overall decision> AA, A: acceptable, C: unacceptable

| | HV (mg/g) | WPE (g/eq) | α | β | ε | Reaction temperature (° C.) | Epoxy group reaction rate (%) | Episulfide group yield (%) | Decision | Reaction time HR | Decision | Overall decision |
|---|---|---|---|---|---|---|---|---|---|---|---|---|
| Example 233 | 1245 | 58 | 2 | 0.28 | — | 20 | 100 | 88 | A | 6 | AA | A |
| Example 234 | 1475 | 72 | 2 | 0.25 | — | 20 | 100 | 87 | A | 2 | AA | A |
| Example 235 | 1245 | 86 | 2 | 0.28 | — | 20 | 100 | 88 | A | 3 | AA | A |
| Example 236 | 1475 | 100 | 2 | 0.29 | — | 20 | 100 | 93 | AA | 3 | AA | AA |
| Example 237 | 1245 | 114 | 2 | 0.28 | — | 20 | 100 | 93 | AA | 2 | AA | AA |
| Example 238 | 1245 | 128 | 2 | 0.3 | — | 20 | 100 | 95 | AA | 1 | AA | AA |
| Example 239 | 1245 | 156 | 2 | 0.28 | — | 20 | 100 | 93 | AA | 3 | AA | AA |
| Example 240 | 1245 | 184 | 2 | 0.28 | — | 20 | 100 | 95 | AA | 2 | AA | AA |
| Example 241 | 1245 | 212 | 2 | 0.28 | — | 20 | 100 | 93 | AA | 2 | AA | AA |
| Example 242 | 1245 | 240 | 2 | 0.28 | — | 20 | 100 | 95 | AA | 4 | AA | AA |
| Example 243 | 1245 | 268 | 2 | 0.28 | — | 20 | 100 | 94 | AA | 2 | AA | AA |
| Example 244 | 1245 | 297 | 2 | 0.3 | — | 20 | 100 | 95 | AA | 3 | AA | AA |
| Example 245 | 1245 | 189 | 2 | 0.21 | — | 20 | 100 | 96 | AA | 2 | AA | AA |
| Example 246 | 1245 | 205 | 2 | 0.21 | — | 20 | 100 | 94 | AA | 4 | AA | AA |
| Example 247 | 1245 | 480 | 2 | 0.08 | — | 60 | 100 | 92 | AA | 6 | AA | AA |
| Example 248 | 1245 | 560 | 2 | 0.05 | — | 80 | 100 | 88 | A | 5 | AA | A |
| Example 249 | 1245 | 650 | 2 | 0.04 | — | 80 | 100 | 84 | A | 6 | AA | A |
| Example 250 | 1245 | 84 | 2 | 0.28 | — | 20 | 100 | 84 | A | 12 | A | A |
| Example 251 | 1245 | 98 | 2 | 0.28 | — | 20 | 100 | 92 | AA | 8 | A | A |
| Example 252 | 1245 | 112 | 2 | 0.28 | — | 20 | 100 | 82 | A | 18 | A | A |
| Example 253 | 1245 | 126 | 2 | 0.28 | — | 20 | 100 | 85 | A | 22 | A | A |
| Example 254 | 1245 | 131 | 2 | 0.28 | — | 20 | 100 | 94 | AA | 15 | A | A |
| Example 255 | 1245 | 91 | 2 | 0.28 | — | 20 | 100 | 95 | AA | 2 | AA | AA |
| Example 256 | 1245 | 181 | 2 | 0.28 | — | 20 | 100 | 96 | AA | 1 | AA | AA |
| Example 257 | 1245 | 191 | 2 | 0.3 | — | 20 | 100 | 92 | AA | 15 | A | A |
| Example 258 | 1245 | 174 | 2 | 0.28 | — | 20 | 100 | 96 | AA | 1 | AA | AA |
| Example 259 | 1245 | 184 | 2 | 0.28 | — | 20 | 100 | 91 | AA | 18 | A | A |
| Example 260 | 1245 | 70 | 2 | 0.28 | — | 20 | 100 | 84 | A | 4 | AA | A |
| Example 261 | 1245 | 98 | 2 | 0.28 | — | 20 | 100 | 93 | AA | 2 | AA | AA |
| Example 262 | 1245 | 114 | 2 | 0.28 | — | 20 | 100 | 95 | AA | 1 | AA | AA |
| Example 263 | 1245 | 124 | 2 | 0.28 | — | 20 | 100 | 92 | AA | 20 | A | A |
| Example 264 | 1245 | 142 | 2 | 0.28 | — | 20 | 100 | 93 | AA | 2 | AA | AA |

TABLE 11

<Decision> AA: particularly satisfactory, A: satisfactory, C: poor,
<Overall decision> AA, A: acceptable, C: unacceptable

| | HV (mg/g) | WPE (g/eq) | α | β | ε | Reaction temperature (° C.) | Epoxy group Reaction rate (%) | Episulfide group yield (%) | Decision | Reaction time HR | Decision | Overall Decision |
|---|---|---|---|---|---|---|---|---|---|---|---|---|
| Example 288 | 1808 | 150 | 2 | 0.29 | — | 20 | 100 | 87 | A | 4 | AA | A |
| Example 289 | 1475 | 150 | 2 | 0.29 | — | 20 | 100 | 93 | AA | 2 | AA | AA |
| Example 290 | 1475 | 150 | 2 | 0.29 | — | 20 | 100 | 92 | AA | 4 | AA | AA |
| Example 291 | 1245 | 150 | 2 | 0.28 | — | 20 | 100 | 96 | AA | 2 | AA | AA |
| Example 292 | 1245 | 150 | 2 | 0.24 | — | 20 | 100 | 93 | AA | 4 | AA | AA |
| Example 293 | 1245 | 150 | 2 | 0.26 | — | 20 | 100 | 95 | AA | 2 | AA | AA |
| Example 294 | 1078 | 150 | 2 | 0.20 | — | 20 | 100 | 93 | AA | 2 | AA | AA |
| Example 295 | 950 | 150 | 2 | 0.12 | — | 20 | 100 | 93 | AA | 2 | AA | AA |
| Example 296 | 767 | 150 | 2 | 0.08 | — | 20 | 100 | 92 | AA | 3 | AA | AA |
| Example 297 | 1828 | 150 | 2 | 0.12 | — | 20 | 100 | 81 | A | 20 | A | A |
| Example 298 | 1057 | 150 | 2 | 0.2 | — | 20 | 100 | 89 | A | 7 | A | A |
| Example 299 | 747 | 150 | 2 | 0.17 | — | 20 | 100 | 86 | A | 12 | A | A |
| Example 300 | 578 | 150 | 2 | 0.17 | — | 20 | 100 | 84 | A | 12 | A | A |
| Example 301 | 471 | 150 | 2 | 0.15 | — | 20 | 100 | 85 | A | 15 | A | A |
| Example 302 | 397 | 150 | 2 | 0.13 | — | 20 | 100 | 83 | A | 19 | A | A |
| Example 303 | 303 | 150 | 2 | 0.11 | — | 20 | 100 | 82 | A | 20 | A | A |
| Example 304 | 205 | 150 | 2 | 0.1 | — | 20 | 100 | 81 | A | 23 | A | A |
| Example 305 | 1838 | 150 | 2 | 0.38 | 0.08 | 20 | 100 | 89 | A | 9 | A | A |
| Example 306 | 1844 | 150 | 2 | 0.40 | 0.08 | 20 | 100 | 87 | A | 12 | A | A |
| Example 307 | 1848 | 150 | 2 | 0.38 | 0.08 | 20 | 100 | 85 | A | 12 | A | A |
| Example 308 | 1851 | 150 | 2 | 0.42 | 0.06 | 20 | 100 | 83 | A | 16 | A | A |
| Example 309 | 1557 | 150 | 2 | 0.40 | 0.07 | 20 | 100 | 82 | A | 20 | A | A |
| Example 310 | 1311 | 150 | 2 | 0.42 | 0.07 | 20 | 100 | 81 | A | 23 | A | A |

TABLE 12

<Decision> AA: particularly satisfactory, A: satisfactory, C: poor,
<Overall decision> AA, A: acceptable, C: unacceptable

| | HV (mg/g) | WPE (g/eq) | α | β | ε | Reaction temperature (°C.) | Epoxy group reaction rate (%) | Episulfide group yield (%) | Decision | Reaction time HR | Decision | Overall decision |
|---|---|---|---|---|---|---|---|---|---|---|---|---|
| Example 334 | 1808 | 150 | 2 | 0.29 | — | 20 | 100 | 87 | A | 4 | AA | A |
| Example 335 | 1475 | 150 | 2 | 0.29 | — | 20 | 100 | 94 | AA | 2 | AA | AA |
| Example 336 | 1475 | 150 | 2 | 0.29 | — | 20 | 100 | 92 | AA | 4 | AA | AA |
| Example 337 | 1245 | 150 | 2 | 0.28 | — | 20 | 100 | 95 | AA | 2 | AA | AA |
| Example 338 | 1245 | 150 | 2 | 0.24 | — | 20 | 100 | 92 | AA | 4 | AA | AA |
| Example 339 | 1245 | 150 | 2 | 0.26 | — | 20 | 100 | 96 | AA | 2 | AA | AA |
| Example 340 | 1078 | 150 | 2 | 0.20 | — | 20 | 100 | 92 | AA | 2 | AA | AA |
| Example 341 | 950 | 150 | 2 | 0.12 | — | 20 | 100 | 94 | AA | 2 | AA | AA |
| Example 342 | 767 | 150 | 2 | 0.08 | — | 20 | 100 | 92 | AA | 3 | AA | AA |
| Example 343 | 1828 | 150 | 2 | 0.12 | — | 20 | 100 | 81 | A | 20 | A | A |
| Example 344 | 1057 | 150 | 2 | 0.2 | — | 20 | 100 | 89 | A | 7 | A | A |
| Example 345 | 747 | 150 | 2 | 0.17 | — | 20 | 100 | 86 | A | 12 | A | A |
| Example 346 | 578 | 150 | 2 | 0.17 | — | 20 | 100 | 83 | A | 12 | A | A |
| Example 347 | 471 | 150 | 2 | 0.15 | — | 20 | 100 | 85 | A | 15 | A | A |
| Example 348 | 397 | 150 | 2 | 0.13 | — | 20 | 100 | 82 | A | 19 | A | A |
| Example 349 | 1245 | 150 | 2 | 0.28 | — | 20 | 100 | 88 | A | 4 | AA | A |
| Example 350 | 1245 | 150 | 2 | 0.3 | — | 20 | 100 | 88 | A | 4 | AA | A |
| Example 351 | 1245 | 150 | 2 | 0.41 | — | 20 | 100 | 87 | A | 2 | AA | A |

The invention claimed is:

1. A method for producing an episulfide compound, the method comprising thiating epoxy groups of (B) an epoxy compound by a reaction with (C) a thiating agent in the presence of (A) a polyhydric hydroxyl compound having two or more hydroxyl groups,
wherein the mixing index β of the (A) polyhydric hydroxyl compound and the (C) thiating agent, which is represented by the following formula (2), is 0.010 to 0.500:

$$\text{Mixing index } \beta = \beta t/\beta o \quad (2)$$

wherein βt: mass (g) of the thiating agent; and
βo: mass (g) of the polyhydric hydroxyl compound.

2. The method according to claim 1, wherein a hydroxyl value of the (A) polyhydric hydroxyl compound is 500 mg/g or more.

3. The method according to claim 1, wherein the (A) polyhydric hydroxyl compound has 3 to 20 carbon atoms.

4. The method according to claim 1, wherein the (A) polyhydric hydroxyl compound is a compound having a chain-like, branched or cyclic aliphatic hydrocarbon group, and the two or more hydroxyl groups contained in the (A) polyhydric hydroxyl compound are each respectively bonded to different carbon atoms in the aliphatic hydrocarbon group.

5. The method according to claim 1, wherein the (C) thiating agent comprises at least one compound selected from the group consisting of thiocyanates and thioureas.

6. The method according to claim 1, wherein the (B) epoxy compound has an epoxy equivalent of 55 g/eq. to 700 g/eq.

7. The method according to claim 1 wherein the (B) epoxy compound is at least one compound selected from the group consisting of a monofunctional epoxy compound, a polyfunctional epoxy compound which is a glycidyl etherification product of a polyphenol compound, an alicyclic epoxy compound, a polyfunctional epoxy compound which is a glycidyl etherification product of novolac compounds, a nuclear-hydrogenated product of an aromatic epoxy compound, a heterocyclic epoxy compound, a glycidyl ester-based epoxy compound, a glycidylamine-based epoxy compound, an epoxy compound obtained by glycidylating a halogenated phenol, a sulfur-containing polyfunctional aliphatic epoxy compound, a silicone compound having an epoxy group in the molecule, and a heteropolymerizable substituent-containing epoxy compound.

8. The method according to claim 1, wherein the mixing index α of the (B) epoxy compound and the (C) thiating agent, which is represented by the following formula (1), is 1 to 10:

$$\text{Mixing index } \alpha = \alpha t/\alpha e \quad (1)$$

wherein αt: amount of substance (mol) of sulfur atoms contained in the thiating agent, which atoms can be used in the production of episulfide groups; and
αe: amount of substance (mol) of epoxy groups contained in the epoxy compound.

* * * * *